United States Patent
Ojima et al.

(10) Patent No.: US 10,213,406 B2
(45) Date of Patent: Feb. 26, 2019

(54) α- AND γ-TRUXILLIC ACID DERIVATIVES AND PHARMACEUTICAL COMPOSITIONS THEREOF

(71) Applicants: Iwao Ojima, Port Jefferson, NY (US); Dale Deutsch, Stony Brook, NY (US); Martin Kaczocha, Dix Hills, NY (US); William T. Berger, Mastic, NY (US); Robert Rizzo, Huntington, NY (US); Trent E. Balius, Stony Brook, NY (US)

(72) Inventors: Iwao Ojima, Port Jefferson, NY (US); Dale Deutsch, Stony Brook, NY (US); Martin Kaczocha, Dix Hills, NY (US); William T. Berger, Mastic, NY (US); Robert Rizzo, Huntington, NY (US); Trent E. Balius, Stony Brook, NY (US)

(73) Assignee: THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 0 days.

(21) Appl. No.: 15/429,656

(22) Filed: Feb. 10, 2017

(65) Prior Publication Data
US 2017/0216241 A1 Aug. 3, 2017

Related U.S. Application Data

(62) Division of application No. 14/413,621, filed as application No. PCT/US2013/051337 on Jul. 19, 2013, now Pat. No. 9,604,904.

(60) Provisional application No. 61/674,108, filed on Jul. 20, 2012.

(51) Int. Cl.
| | | |
|---|---|---|
| A61K 31/216 | (2006.01) |
| C07C 67/08 | (2006.01) |
| C07C 211/58 | (2006.01) |
| C07C 233/11 | (2006.01) |
| C07C 233/58 | (2006.01) |
| C07C 235/38 | (2006.01) |
| C07C 235/40 | (2006.01) |
| C07C 69/753 | (2006.01) |
| C07C 69/76 | (2006.01) |
| C07C 67/48 | (2006.01) |
| C07C 69/757 | (2006.01) |
| G01N 33/566 | (2006.01) |
| A61K 31/194 | (2006.01) |
| G01N 33/68 | (2006.01) |

(52) U.S. Cl.
CPC .......... *A61K 31/216* (2013.01); *A61K 31/194* (2013.01); *C07C 67/08* (2013.01); *C07C 67/48* (2013.01); *C07C 69/753* (2013.01); *C07C 69/757* (2013.01); *C07C 69/76* (2013.01); *C07C 211/58* (2013.01); *C07C 233/11* (2013.01); *C07C 233/58* (2013.01); *C07C 235/38* (2013.01); *C07C 235/40* (2013.01); *G01N 33/566* (2013.01); *G01N 33/68* (2013.01); *C07B 2200/07* (2013.01); *C07C 2601/04* (2017.05); *G01N 2333/47* (2013.01); *G01N 2500/04* (2013.01); *G01N 2500/20* (2013.01)

(58) Field of Classification Search
CPC .......................... A61K 31/216; A61K 31/194
See application file for complete search history.

(56) References Cited

U.S. PATENT DOCUMENTS

2009/0163545 A1   6/2009   Goldfarb

FOREIGN PATENT DOCUMENTS

| CN | 101838239 A | 9/2010 |
| EP | 1118324 A1 | 7/2001 |
| ES | 2 189 602 A1 | 7/2003 |
| WO | WO 2003/043624 A1 | 5/2003 |
| WO | WO 2014/015276 | 1/2014 |
| WO | WO 2017/156354 | 9/2017 |

OTHER PUBLICATIONS

Steri (Bioorganic and Medicinal Chemistry Letters; 2010, 20, 2920-2923).*
International Search Report dated Jun. 29, 2017 in connection with International Application No. PCT/US2017/021711.

(Continued)

*Primary Examiner* — Pancham Bakshi
(74) *Attorney, Agent, or Firm* — Gary J. Gershik; Cooper & Dunham LLP

(57) ABSTRACT

The present invention provides a compound, and method of inhibiting the activity of a Fatty Acid Binding Protein (FABP) comprising contacting the FABP with a compound, having the structure:

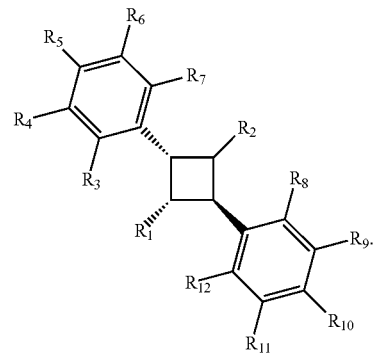

14 Claims, 22 Drawing Sheets

(56) References Cited

OTHER PUBLICATIONS

Written Opinion of the International Search Authority dated Jun. 29, 2017 in connection with International Application No. PCT/US2017/021711.
Communication Pursuant to Art. 94(3) EPC dated Mar. 23, 2017 by the European Patent Office in connection with European Application No. EP 13820647.9.
Jul. 21, 2017 Amendment filed with the European Patent Office in connection with European Application No. EP 13820647.9.
Communication Pursuant to Art. 94(3) EPC dated Nov. 13, 2017 by the European Patent Office in connection with European Application No. EP 13820647.9.
Mar. 13, 2018 Amendment filed with the European Patent Office in connection with European Application No. EP 13820647.9.
Steri, R. et al. (2010). Truxillic acid derivatives act as peroxisome proliferator-activated receptor γ activators. *Bioorganic & Medicinal Chemistry Letters*, 20(9), 2920-2923.
Takeda, R. et al. (1990). Phenolic compounds from Anthocerotae. *Proceedings of the Phytochemical Society of Europe*, 29, 201-207 (CAS Registry No. 130396-77-9 only).
Ford, C. W. and Hartley, R. D. (1990). Cyclodimers of p-coumaric and ferulic acids in the cell walls of tropical grasses. *Journal of the Science of Food and Agriculture*, 50(1), 29-43.
Pera, N. H. et al. (1972). Truxillic acid amides. *Chimica Therapeutica*, 7(1), 42-44 (CAS Registry No. 37518-16-4, 37518-17-5 only).
Arendaruk, A. P. and Skoldinov, A. P. (1960). Cyclobutanedicarboxylic acids. III. Basic esters of α-truxillic acid. *Zhurnal Obshchei Khimii*, 30, 2743-2745 (CAS Registry No. 857215-35-1, 860416-41-7 only).
Schenck, F. (1930). Resolution of some ester acids of the γ-truxillic acids into the optical components. *Berichte der Deutschen Chemischen Gesellschaft [Abteilung] B: Abhandlungen*, 63B, 2706-2712 (CAS Registry No. 321863-32-5 only).
Notification of Transmittal of the International Search Report and the Written Opinion of the International Searching Authority, or the Declaration, including an International Search Report and Written Opinion of the International Searching Authority, dated Dec. 26, 2013 in connection with PCT International Application No. PCT/US2013/051337, filed Jul. 19, 2013.
Arendaruk, A. P. et al. (1967). Studies on cyclobutanedicarboxylic acids v. synthesis of bisquaternary salts of alkylamine esters and amides of the stereoisomeric truxillic acids. Institute of Pharmacology and Chemotherapy, Academy of Medical Sciences of the USSR, Moscow, 8, 445-448.
Berger, W. T. et al. (2012). Targeting fatty acid binding protein (FABP) anandamide transporters—A novel strategy for development of anti-inflammatory and anti-nociceptive drugs. *PLOS ONE*, 7(2), 1-12.
Chi, Y. et al. (2005). Anti-inflammatory activities of α-truxillic acid derivatives and their monomer components. *Biological and Pharmaceutical Bulletin*, 28(9), 1776-1778.
Chi, Y. et al. (2006). Antinociceptive activities of α-truxillic acid and β-truxinic acid derivatives. *Biological and Pharmaceutical Bulletin*, 29(3), 580-584.
Ichikawa, M. et al. (2004). Total synthesis of (−)-Incarvilline, (+)-Incarvine C, and (−)-Incarvillateine. *Journal of the American Chemical Society*, 126, 16553-16558.
Krauze-Baranowska, M. (2002). Truxillic and truxinic acids —Occurrence in plant kingdom. *Acta Poloniae Pharmaceutica—Drug Research*, 59(5), 403-410.
Nakamura, M. et al. (1999). Strong antinociceptive effect of incarvillateine, a novel monoterpene alkaloid from *Incarvillea sinensis*. *Journal of Natural Products*, 62, 1293-1294.

Rupp, M. et al. (2010). From machine learning to natural product derivatives that selectively activate transcription factor PPARγ. *ChemMedChem*, 5, 191-194.
Yang, H. et al. (2011). Novel photolabile diblock copolymers bearing truxillic acid derivative junctions. *Macromolecules*, 44, 159-165.
Notification Concerning Transmittal of International Preliminary Report on Patentability (Chapter I of the Patent Cooperation Treaty), including an International Preliminary Report on Patentability and Written Opinion of the International Searching Authority, dated Jan. 29, 2015 by the International Bureau of WIPO in connection with PCT International Application No. PCT/US2013/051337, filed Jul. 19, 2013.
Gutekunst, W. et al. (2011) Total Synthesis and Structural Revision of the Poperaborenines via Sequential Cyclobutane C—H Arylation, Journal of the American Chemical Society, vol. 133, No. 47, pp. 19076-19079.
Huong, D. et al. (2008) Two New Bis-styryl Compounds from Miliusa Balansae. Z. Naturforsch, vol. 63b, pp. 335-338.
Arendaruk, A. P. et al. (1986) Chemical Abstract Service, CAPLUS No. 1986:625826.
Feb. 17, 2016 European Search Report issued in connection with the European Patent Application No. 13820647.9.
Sep. 14, 2016 Amendment filed with the European patent office in connection with European counterpart patent application No. 13820647.9.
Thieme T. M. et al. (2010) Rational design of a pirinixic acid derivative that acts as subtype-selective PPARγ modulator, Bioorganic & Medicinal Chemistry Letters, vol. 20, pp. 2920-2923.
Non-Final Office Action issued by the U.S. Patent and Trademark Office dated Aug. 28, 2015 in connection with U.S. Appl. No. 14/413,621.
Response to Aug. 28, 2015 Office Action, filed with the U.S. Patent and Trademark Office dated Oct. 28, 2015 in connection with U.S. Appl. No. 14/413,621.
Non-Final Office Action issued by the U.S. Patent and Trademark Office dated Nov. 6, 2015 in connection with U.S. Appl. No. 14/413,621.
Response to Nov. 6, 2015 Office Action, filed with the U.S. Patent and Trademark Office dated Feb. 5, 2016 in connection with U.S. Appl. No. 14/413,621.
Final Office Action issued by the U.S. Patent and Trademark Office dated Apr. 12, 2016 in connection with U.S. Appl. No. 14/413,621.
Response to Apr. 12, 2016 Final Office Action, filed with the U.S. Patent and Trademark Office dated Jun. 13, 2016 in connection with U.S. Appl. No. 14/413,621.
Advisory Action issued by the U.S. Patent and Trademark Office dated Jun. 22, 2016 in connection with U.S. Appl. No. 14/413,621.
Response to Apr. 12, 2016 Final Office Action and Jun. 22, 2016 Advisory Action, filed with the U.S. Patent and Trademark Office dated Jun. 30, 2016 in connection with U.S. Appl. No. 14/413,621.
Non-Final Office Action issued by the U.S. Patent and Trademark Office dated Jul. 15, 2016 in connection with U.S. Appl. No. 14/413,621.
Response to Jul. 15, 2016 Office Action, filed with the U.S. Patent and Trademark Office dated Oct. 7, 2016 in connection with U.S. Appl. No. 14/413,621.
Notice of Allowance issued by the U.S. Patent and Trademark Office dated Nov. 10, 2016 in connection with U.S. Appl. No. 14/413,621.
Communication Pursuant to Art. 94(3) EPC dated Jun. 28, 2018 by the European Patent Office in connection with European Application No. EP 13820647.9.

\* cited by examiner

AEA (Anandamide) FAAH (fatty acid amide hydrolase)
FABP (fatty acid binding protein), CB (cannabinoid receptor)

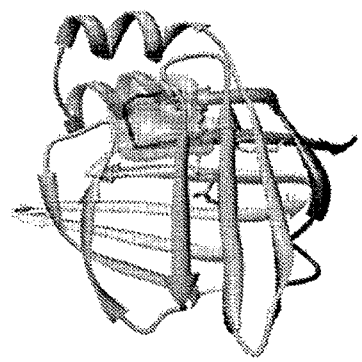
Figure 5A
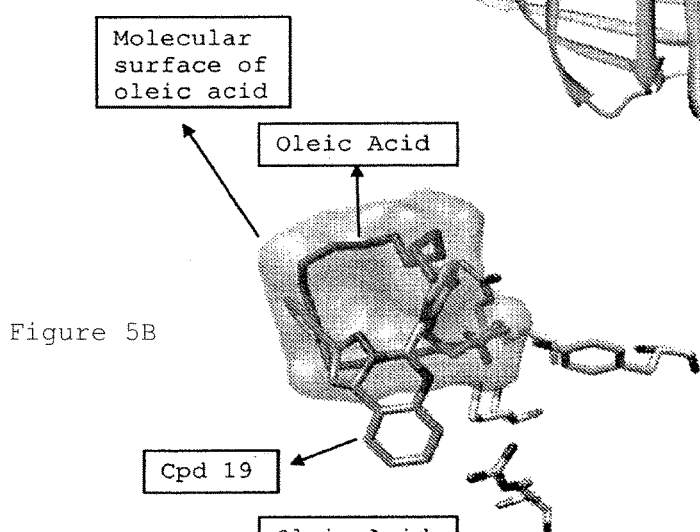
Figure 5B
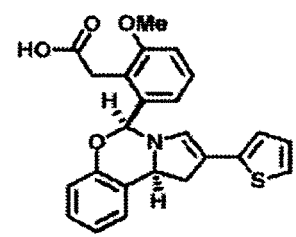
Compound 19
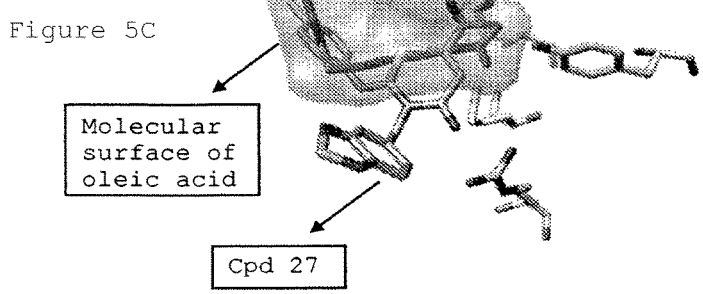
Figure 5C
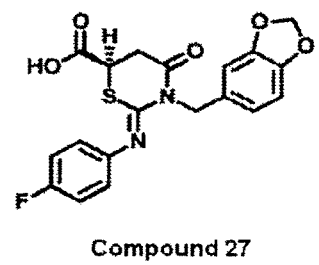
Compound 27

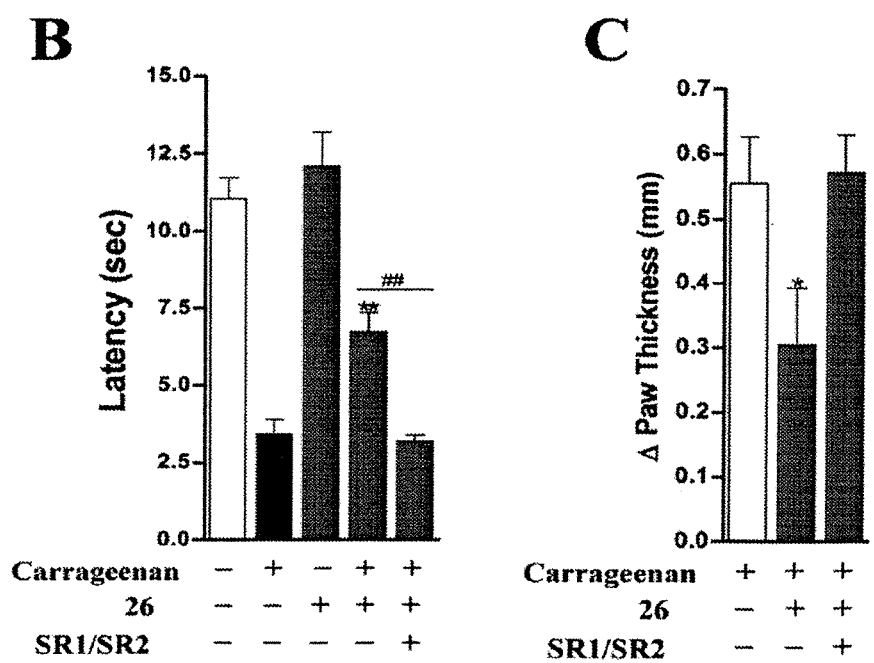
Figure 10B                    Figure 10C

α- AND γ-TRUXILLIC ACID DERIVATIVES AND PHARMACEUTICAL COMPOSITIONS THEREOF

CROSS-REFERENCE TO RELATED APPLICATIONS

This application is a divisional of U.S. Ser. No. 14/413,621, filed Jan. 8, 2015, now allowed, which is a § 371 national stage of PCT International Application No. PCT/US2013/051337, filed Jul. 19, 2013, claiming the benefit of U.S. Provisional Application No. 61/674,108, filed Jul. 20, 2012, the entire contents of each of which are hereby incorporated by reference into the subject application.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

The invention was made with government support under Grant number DA032232, DA026953, and DA016419 awarded by the National Institutes of Health. The government has certain rights in the invention.

BACKGROUND OF THE INVENTION

Lipids, owing to their water insolubility, require a variety of fatty acid binding protein (FABP) chaperones or transporters to carry them throughout cells (Furuhashi, M et al. 2008). The FABPs are part of the pathway of anandamide inactivation by the fatty acid amide hydrolase (FAAH), an enzyme localized inside the cell on the endoplasmic reticulum. The endocannabinoid anandamide (arachidonoyl ethanolamide or AEA) is an uncharged neuromodulatory lipid that is inactivated through its cellular uptake by FABPs and subsequent hydrolysis by FAAH into ethanolamine and arachidonic acid.

Cannabinoids such as anandamide have broad effects on the central nervous system (CNS) and influence, for example, movement, memory, nociception, endocrine regulation, thermoregulation, sensory perception, cognitive functions, and mood. Similarly, genetic and pharmacological studies have revealed a broad role for endocannabinoid signaling in a variety of physiological processes, including neuromodulator release, motor learning, synaptic plasticity, appetite, and pain sensation. Anandamide produces most of its pharmacological effects by binding and activating the cannabinoid receptor (CB-1 and CB-2) within the CNS. The increase in extracellular anandamide caused by the inhibition of FABPs triggers activation of the cannabinoid receptor type 1 (CB-1) pathway leading to the relief of neurogenic and inflammatory pain.

Recently, it was shown that anandamide (an endocannabinoid) uses FABPs such as FABP5 (E-FABP) and FABP7 (B-FABP) as intracellular transporters (Kaczocha, M. et al. 2009). FABPs are drug targets similar to FAAH since inhibitors of each decrease hydrolysis of anandamide and its uptake into cells, raising the levels of extracellular anandamide (FIG. 1) (Howlett, A. C. et al. 2011; Kaczocha, M. et al. 2012; Ahn, K. et al. 2009). Few specific FABP inhibitors have been described. There are those that were specifically designed for FABP4, such as BMS309403, which are important for the protective effects that they exert in metabolic syndrome and atherosclerosis (Barf, T. et al. 2009; Sulsky, R. et al. 2007). BMS309403 also binds other FABPs, such as FABP5 and FABP7, that carry anandamide, as do other inhibitors originally designed to inhibit a putative anandamide transmembrane transporter (Kaczocha, M. et al. 2012).

SUMMARY OF THE INVENTION

The present invention provides a compound having the structure:

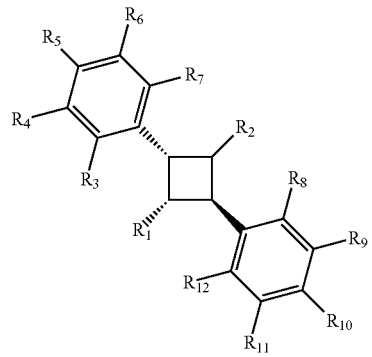

wherein $R_1$ and $R_2$ are different and are each —C(=O)$R_{13}$, —C(=O)O$R_{13}$, —C(=O)N$R_{13}R_{14}$, -alkyl-C(=O)$R_{13}$, -alkyl-C(=O)O$R_{13}$, -alkyl-C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)$R_{13}$, -alkyl-NHC(=O)N$R_{13}R_{14}$, -alkyl-NHC(=S)N$R_{13}R_{14}$, -alkyl-NHC(=N$R_{13}$)N$R_{13}R_{14}$, —C(—OH)C(=O)O$R_{13}$, —C(=O)C(=O)O$R_{13}$ or —C≡C—$R_{13}$, wherein $R_{13}$ and $R_{14}$ are each, independently, H, CF$_3$, C$_{1-10}$ alkyl, C$_{2-10}$ alkenyl, C$_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —NO$_2$, —CN, —NHR$_{15}$, —NR$_{15}R_{16}$, —SR$_{15}$, —SO$_2R_{15}$, —OR$_{15}$, —CO$_2R_{15}$, CF$_3$, -alkyl-NR$_{15}R_{16}$, -alkyl-OR$_{15}$, C$_{1-10}$ alkyl, C$_{2-10}$ alkenyl, C$_{2-10}$ alkynyl, aryl, heteroaryl, or heterocyclyl;

wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl;

when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is —CH$_3$, —CH$_2$CH$_3$, tolyl or propyl 1-bromo-1-methylpropanoyloxybutyl ester, or —C(=O)NR$_{13}R_{14}$ where one of $R_{13}$ or $R_{14}$ is phenyl and the other is —H, or both of $R_{13}$ and $R_{14}$ are —H; and when one of $R_1$ or $R_2$ is —C(=O)OCH$_3$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)NR$_{13}R_{14}$ where one of $R_{13}$ and $R_{14}$ is —H and the other is (2-methylmercapto)phenyl;

or an enantiomer or pharmaceutically acceptable salt thereof.

The present invention provides a method of inhibiting the activity of a Fatty Acid Binding Protein (FABP) comprising contacting the FABP with a compound having the structure:

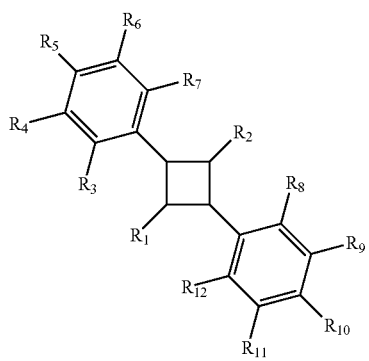

wherein
$R_1$ and $R_2$ are different and are each —C(=O)$R_{13}$, —C(=O)O$R_{13}$, —C(=O)N$R_{13}R_{14}$, -alkyl-C(=O)$R_{13}$, -alkyl-C(=O)O$R_{13}$, -alkyl-C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)$R_{13}$, -alkyl-NHC(=O)N$R_{13}R_{14}$, -alkyl-NHC(=S)N$R_{13}R_{14}$, -alkyl-NHC(=N$R_{13}$)N$R_{13}R_{14}$, —C(—OH)C(=O)O$R_{13}$, —C(=O)C(=O)O$R_{13}$ or —C=C—$R_{13}$, wherein $R_{13}$ and $R_{14}$ are each, independently, H, $CF_3$, $C_{1-10}$ alkyl, $C_{2-10}$ alkenyl, $C_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —$NO_2$, —CN, —NH$R_{15}$, —N$R_{15}R_{16}$, —S$R_{15}$, —$SO_2R_{15}$, —O$R_{15}$, —$CO_2R_{15}$, $CF_3$, -alkyl-NH$R_{15}$, -alkyl-N$R_{15}R_{16}$, -alkyl-O$R_{15}$, $C_{1-10}$ alkyl, $C_{2-10}$ alkenyl, $C_{2-10}$ alkynyl, aryl, heteroaryl, or heterocyclyl;

wherein $R_{15}$ and $R_{16}$ are each, independently, H, $CF_3$, $C_{1-10}$ alkyl, $C_{2-10}$ alkenyl, $C_{2-10}$ alkynyl, heteroalkyl, aryl, heteroaryl, or heterocyclyl;

when one of $R_1$ or $R_2$ is —C(=O)OH or —C(=O)O$CH_3$, then the other of $R_1$ or $R_2$ is other than —C(=O)O$R_{13}$ where $R_{13}$ is alkyl, heteroalkyl, substituted phenyl or benzyl, —C(=O)NH$R_{13}R_{14}$ where one of $R_{13}$ or $R_{14}$ is —H, phenyl or substituted phenyl and the other is —H, or —C(=O)N$R_{13}R_{14}$ where $R_{13}$ and $R_{14}$ combine to form a piperidine or morpholine;

or a pharmaceutically acceptable salt thereof.

The present invention provides a method of identifying an agent that inhibits the activity of a Fatty Acid Binding Protein (FABP) comprising contacting a Fatty Acid Binding Protein (FABP) expressed in the CNS with the agent and separately with a compound having the structure

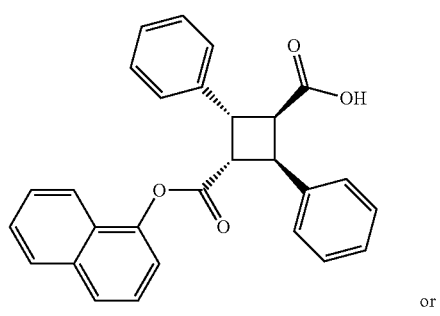

or

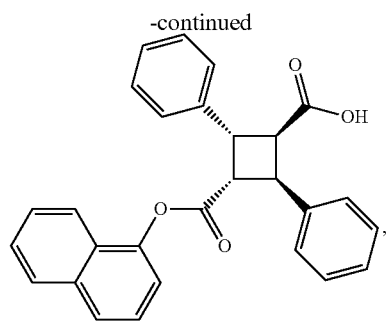

and comparing the FABP inhibitory activity of the agent with the FABP inhibitory activity of the compound to identify an agent where FABP inhibitory activity is greater than that of the compound.

BRIEF DESCRIPTION OF THE FIGURES

FIGS. 5A-5E. FIG. 5A is FABP7 with oleic acid bound and the molecular surface of oleic acid rendered in grey. FIGS. 5B-5E show lead compounds identified through the high throughput fluorescence displacement assay with NBD-stearate. Each of the leads is represented in 3D (left) and 2D space (right). Shown in the 3D structures, each of the leads determined by biological assay contained a carboxylate that bound to ARG106, ARG126, TYR128 a similar binding motif of the reference oleic acid. Additionally, each lead is shown to occupy the same chemical space as the reference oleic acid.

(FIG. 8A) Assay in triplicate shows that Compound 26 attains a $K_i$ within nanoMolar ranges. (FIG. 8B) Compound 49 is as potent as BMS309403. (FIG. 8C) BMS309403 was found to be slightly more potent in this study (Ki, 0.75 µM) than published (Ki, 0.89 µM), but still within range of this value.

(FIG. 9A) AEA uptake in wild-type HeLa (unshaded) or FABP5 shRNA-expressing HeLa (shaded) cells in the presence or absence of Compound 26. (FIG. 9B) AEA hydrolysis in FAAH-transfected HeLa cells in the presence or absence of Compound 26 or the FAAH inhibitor URB597. , $p<0.01$; *, $p<0.001$ (n=3).

FIGS. 10A-10C. Antinociceptive effects of Compound 26. (FIG. 10A) Compound 26 (20 mg/kg, i.p.) reduces pain associated with the first phase (left panel) but not the second phase (right panel) of the formalin test. *, $p<0.05$ (n=6). (FIG. 10B) Compound 26 (20 mg/kg, i.p.) alleviates carrageenan-induced thermal hyperalgesia in mice. Concurrent administration of rimonabant and SR144528 (SR1/SR2) blocked the antinociceptive effects of Compound 26. **, $p<0.01$ versus carrageenan-injected animals; ##, $p<0.01$ versus SR1/SR2-treated animals (n=6-9). (FIG. 10C) Compound 26 (20 mg/kg, i.p.) reduces carrageenan-induced paw edema. *, $p<0.05$ (n=6-9).

(FIG. 11A) PPARα activation by Compound 26 and the PPARα agonist GW7647. (FIG. 11B) Activation of PPARγ receptors by Compound 26 compared to the PPARγ agonist rosiglitazone (n=3).

(FIG. 13A) Replicate testing of the lead compounds shows that Compound 26 exhibits the best inhibition of FABP5. (FIG. 13B) Controls show that all of the lead compounds exhibited no detectable fluorescence in the assay nor did they add significantly to the fluorescence of the NBD-stearate probe. *, $p<0.05$; , $p<0.01$; *, $p<0.001$ (n=3).

(FIG. 16A) Compounds 26 and 54 (20 mg/kg, i.p.) reduced carrageenan-induced thermal hyperalgesia (left panel) and paw edema (right panel) in mice. Measurements were performed 24 hrs after inhibitor administration. *, $p<0.05$; **, $p<0.01$. (FIG. 16B) Compounds 26 and 54 reduce the first (left panel) and second phases (right panel) of formalin-induced nociception in mice. *, $p<0.05$; , $p<0.01$. (FIG. 16C) Compound 26 reduces acetic acid-induced writhing in mice. , $p<0.01$. (FIG. 16D) Dose-response of Compound 26-mediated inhibition of acetic acid writhing in mice. **, $p<0.01$. (FIG. 16E) The antinociceptive effects of Compound 26 are reversed by the cannabinoid receptor 1 antagonist SR141716 (SR1, 3 mg/kg) and the peroxisome proliferator-activated receptor alpha antagonist GW6471 (4 mg/kg). *, $p<0.05$; **, $p<0.01$ versus control. ##, $p<0.01$; ###, $p<0.001$ versus Compound 26 treated mice.

DETAILED DESCRIPTION OF THE INVENTION

Figure 1:
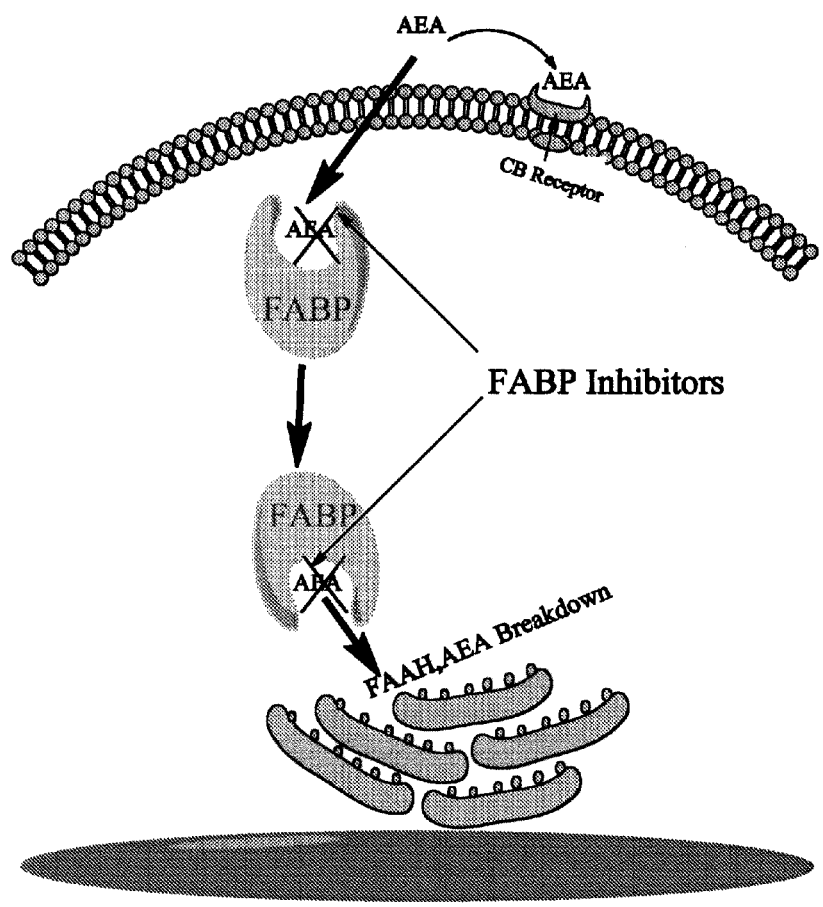
FIG. 1. Scheme demonstrating anandamide inactivation and FABP drug target. Anandamide crosses the membrane by diffusion but requires FABPs for transport through the cytoplasm to the endoplasmic reticulum for breakdown by FAAH. FABP inhibitors prevent AEA from being delivered to FAAH for breakdown resulting in increased AEA levels at the receptor.

The present invention provides a compound having the structure:

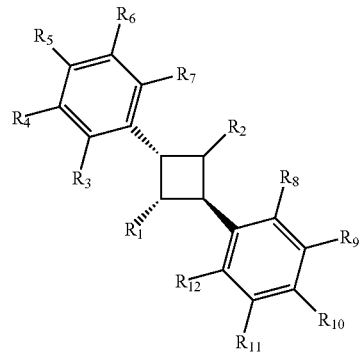

wherein
$R_1$ and $R_2$ are different and are each —C(=O)$R_{13}$, —C(=O)O$R_{13}$, —C(=O)N$R_{13}R_{14}$, -alkyl-C(=O)$R_{13}$, -alkyl-C(=O)O$R_{13}$, -alkyl-C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)$R_{13}$, -alkyl-NHC(=O)N$R_{13}R_{14}$, -alkyl-NHC(=S)N$R_{13}R_{14}$, -alkyl-NHC(=N$R_{13}$)N$R_{13}R_{14}$, —C(—OH)C(=O)O$R_{13}$, —C(=O)C(=O)O$R_{13}$ or —C=C—$R_{13}$, wherein $R_{13}$ and $R_{14}$ are each, independently, H, CF$_3$, C$_{1-10}$ alkyl, C$_{2-10}$ alkenyl, C$_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —NO$_2$, —CN, —NH$R_{15}$, —N$R_{15}R_{16}$, —S$R_{15}$, —SO$_2R_{15}$, —O$R_{15}$, —CO$_2R_{15}$, CF$_3$, -alkyl-N$R_{15}R_{16}$, -alkyl-O$R_{15}$, C$_{1-10}$ alkyl, C$_{2-10}$ alkenyl, C$_{2-10}$ alkynyl, aryl, heteroaryl, or heterocyclyl;

wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl;

when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is —CH$_3$, —CH$_2$CH$_3$, tolyl or propyl 1-bromo-1-methylpropanoyloxybutyl ester, or —C(=O)N$R_{13}R_{14}$ where one of $R_{13}$ or $R_{14}$ is phenyl and the other is —H, or both of $R_{13}$ and $R_{14}$ are —H; and when one of $R_1$ or $R_2$ is —C(=O)OCH$_3$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)N$R_{13}R_{14}$ where one of $R_{13}$ and $R_{14}$ is —H and the other is (2-methylmercapto)phenyl;

or an enantiomer or pharmaceutically acceptable salt thereof.

In some embodiments, a compound having the structure:

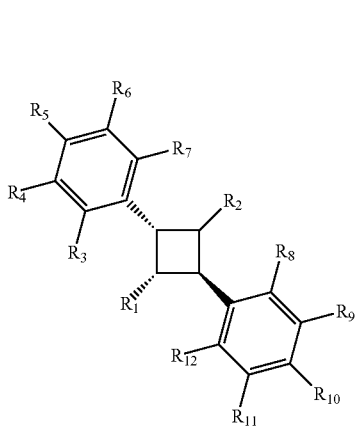

wherein $R_1$ and $R_2$ are different and are each —C(=O)$R_{13}$, —C(=O)O$R_{13}$, —C(=O)N$R_{13}R_{14}$, -alkyl-C(=O)$R_{13}$, -alkyl-C(=O)O$R_{13}$, -alkyl-C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)$R_{13}$, -alkyl-NHC(=O)N$R_{13}R_{14}$, -alkyl-NHC(=S)N$R_{13}R_{14}$, -alkyl-NHC(=N$R_{13}$)N$R_{13}R_{14}$, —C(—OH)C(=O)O$R_{13}$, —C(=O)C(=O)O$R_{13}$ or —C≡C—$R_{13}$, wherein $R_{13}$ and $R_{14}$ are each, independently, H, CF$_3$, C$_{1-10}$ alkyl, C$_{2-10}$ alkenyl, C$_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —NO$_2$, —CN, —NHR$_{15}$, —NR$_{15}R_{16}$, —SR$_{15}$, —SO$_2$R$_{15}$, —OR$_{15}$, —CO$_2$R$_{15}$, CF$_3$, -alkyl-NR$_{15}R_{16}$, -alkyl-OR$_{15}$, C$_{1-10}$ alkyl, C$_{2-10}$ alkenyl, C$_{2-10}$ alkynyl, aryl, heteroaryl, or heterocyclyl;

wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl;

when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)OR$_{13}$ where $R_{13}$ is —CH$_3$, —CH$_2$CH$_3$, —(CH$_2$)$_4$CH$_3$, —(CH$_2$)$_7$CH$_3$, —CH$_2$(CH$_3$)$_2$, —CH$_2$C(O)CH$_3$, tolyl, 1-Naphthol or propyl 1-bromo-1-methylpropanoyloxybutyl ester, or —C(=O)NR$_{13}R_{14}$ where one of $R_{13}$ or $R_{14}$ is phenyl and the other is —H, or both of $R_{13}$ and $R_{14}$ are —H; and when one of $R_1$ or $R_2$ is —C(=O)OCH$_3$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)NR$_{13}R_{14}$ where one of $R_{13}$ and $R_{14}$ is —H and the other is (2-methylmercapto) phenyl;

or an enantiomer or pharmaceutically acceptable salt thereof.

In some embodiments, a compound having the structure:

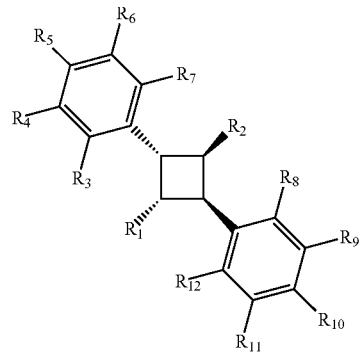

wherein $R_1$ and $R_2$ are different and are each —C(=O)$R_{13}$, —C(=O)OR$_{13}$, —C(=O)NR$_{13}R_{14}$, -alkyl-C(=O)$R_{13}$, -alkyl-C(=O)OR$_{13}$, -alkyl-C(=O)NR$_{13}R_{14}$, -alkyl-OC(=O)OR$_{13}$, -alkyl-OC(=O)$R_{13}$, -alkyl-OR$_{13}$, -alkyl-NR$_{13}R_{14}$, -alkyl-NHC(=O)$R_{13}$, -alkyl-NHC(=O)OR$_{13}$, -alkyl-NHC(=O)R$_{13}$, -alkyl-NHC(=O)NR$_{13}R_{14}$, -alkyl-NHC(=S)NR$_{13}R_{14}$, -alkyl-NHC(=NR$_{13}$)NR$_{13}R_{14}$, —C(—OH)C(=O)OR$_{13}$, —C(=O)C(=O)OR$_{13}$ or —C≡C—R$_{13}$, wherein $R_{13}$ and $R_{14}$ are each, independently, H, CF$_3$, C$_{1-10}$ alkyl, C$_{2-10}$ alkenyl, C$_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —NO$_2$, —CN, —NR$_{15}R_{16}$, —SR$_{15}$, —SO$_2$R$_{15}$, —OR$_{15}$, —CO$_2$R$_{15}$, CF$_3$, -alkyl-NHR$_{15}$, -alkyl-NHR$_{15}R_{16}$, -alkyl-OR$_{15}$, C$_{1-10}$ alkyl, C$_{2-10}$ alkenyl, C$_{2-10}$ alkynyl, aryl, heteroaryl, or heterocyclyl;

wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl;

when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)OR$_{13}$ where $R_{13}$ is —CH$_2$CH$_3$ or propyl 1-bromo-1-methylpropanoyloxybutyl ester;

when one of $R_1$ or $R_2$ is —C(=O)OCH$_3$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)NR$_{13}R_{14}$ where one of $R_{13}$ and $R_{14}$ is —H and the other is (2-methylmercapto)phenyl;

or an enantiomer or pharmaceutically acceptable salt thereof.

In some embodiments, a compound having the structure:

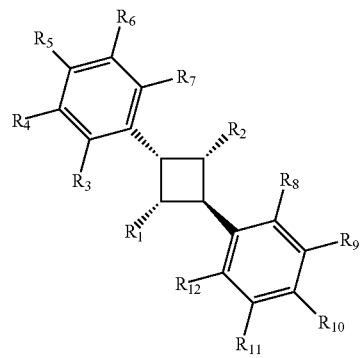

wherein

R₁ and R₂ are different and are each —C(=O)R₁₃, —C(=O)OR₁₃, —C(=O)NR₁₃R₁₄, -alkyl-C(=O)R₁₃, -alkyl-C(=O)OR₁₃, -alkyl-C(=O)NR₁₃R₁₄, -alkyl-OC(=O)OR₁₃, -alkyl-OC(=O)R₁₃, -alkyl-OR₁₃, -alkyl-NR₁₃R₁₄, -alkyl-NHC(=O)R₁₃, -alkyl-NHC(=O)OR₁₃, -alkyl-NHC(=O)R₁₃, -alkyl-NHC(=O)NR₁₃R₁₄, -alkyl-NHC(=S)NR₁₃R₁₄, -alkyl-NHC(=NR₁₃)NR₁₃R₁₄, —C(—OH)C(=O)OR₁₃, —C(=O)C(=O)OR₁₃ or —C≡C—R₁₃, wherein R₁₃ and R₁₄ are each, independently, H, CF₃, C₁₋₁₀ alkyl, C₂₋₁₀ alkenyl, C₂₋₁₀ alkynyl, heteroalkyl, cycloalkyl, aryl, heteroaryl, heterocyclyl or combine to form a cycloalkyl or heterocyclyl;

R₃, R₄, R₅, R₆, R₇, R₈, R₉, R₁₀, R₁₁ and R₁₂ are each independently, H, halogen, —NO₂, —CN, —NHR₁₅, —NR₁₅R₁₆, —SR₁₅, —SO₂R₁₅, —OR₁₅, —CO₂R₁₅, CF₃, -alkyl-NHR₁₅, -alkyl-NHR₁₅R₁₆, -alkyl-OR₁₅, C₁₋₁₀ alkyl, C₂₋₁₀ alkenyl, C₂₋₁₀ alkynyl, aryl, heteroaryl, or heterocyclyl;

wherein R₁₅ and R₁₆ are each, independently, H, CF₃, C₁₋₁₀ alkyl, C₂₋₁₀ alkenyl, C₂₋₁₀ alkynyl, heteroalkyl, cycloheteroalkyl, aryl, heteroaryl, or heterocyclyl;

when one of R₁ or R₂ is —C(=O)OH and R₃, R₄, R₅, R₆, R₇, R₈, R₉, R₁₀, R₁₁ and R₁₂ are each H, then the other of R₁ or R₂ is other than —C(=O)OR₁₃ where R₁₃ is —CH₃ or tolyl or —C(=O)NR₁₃R₁₄ where both of R₁₃ and R₁₄ are —H;

or an enantiomer or pharmaceutically acceptable salt thereof.

In some embodiments, the compound wherein one of R₁ or R₂ is —C(=O)R₁₃, —C(=O)OR₁₃, or —C(=O)NHR₁₃, wherein R₁₃ is aryl or heteroaryl; and the other of R₁ or R₂ is —C(=O)OR₁₃, wherein R₁₃ is H.

In some embodiments, the compound wherein
one of R₁ or R₂ is

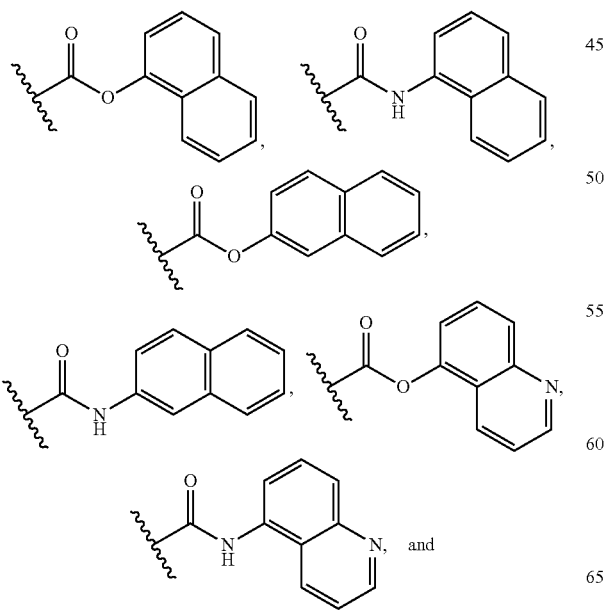

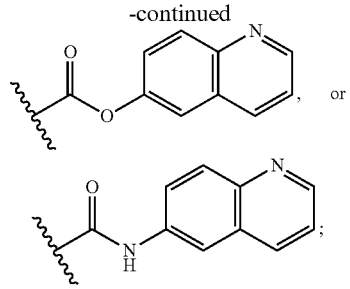

the other of R₁ or R₂ is —C(=O)OH.

In some embodiments, the compound wherein one of R₁ or R₂ is -alkyl-C(=O)R₁₃, -alkyl-C(=O)OR₁₃, -alkyl-C(=O)NHR₁₃, -alkyl-OC(=O)OR₁₃, -alkyl-OC(=O)R₁₃, -alkyl-OR₁₃, -alkyl-NHR₁₃, wherein R₁₃ is H, aryl or heteroaryl; and the other of R₁ or R₂ is —C(=O)OR₁₃, wherein R₁₃ is H.

In some embodiments, the compound wherein
one of R₁ or R₂ is

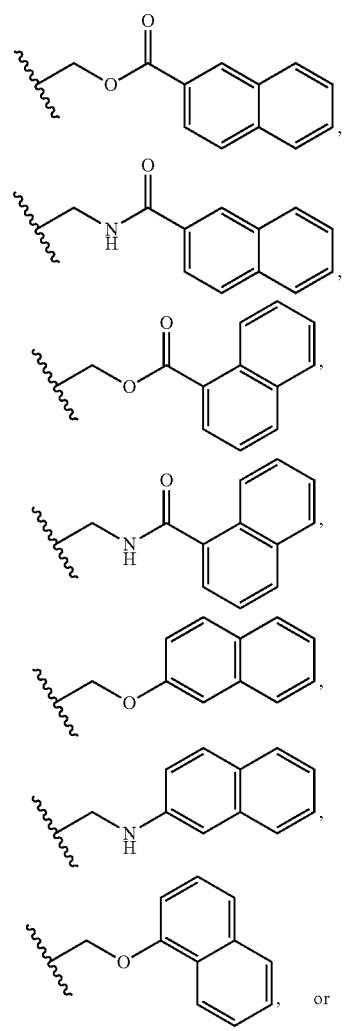

11
-continued

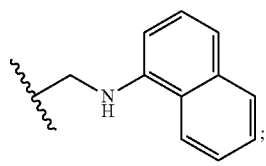

and the other of $R_1$ or $R_2$ is —C(═O)OH.

In some embodiments, the compound wherein one of $R_1$ or $R_2$ is -alkyl-C(═O)$R_{13}$, -alkyl-C(═O)O$R_{13}$, -alkyl-C(═O)NH$R_{13}$, -alkyl-OC(═O)O$R_{13}$, -alkyl-OC(═O)$R_{13}$, -alkyl-O$R_{13}$, -alkyl-NH$R_{13}$, wherein $R_{13}$ is H, aryl or heteroaryl; and the other of $R_1$ or $R_2$ is —C(—OH)C(═O)O$R_{13}$, or —C(═O)C(═O)O$R_{13}$, wherein $R_{13}$ is H or alkyl.

In some embodiments, the compound wherein one of $R_1$ or $R_2$ is

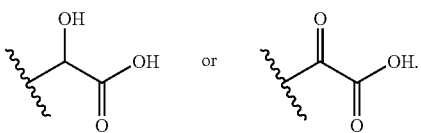 [SMILES: *C(O)C(=O)O ; "or" ; *C(=O)C(=O)O]

12
-continued

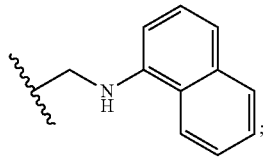

and the other of $R_1$ or $R_2$ is

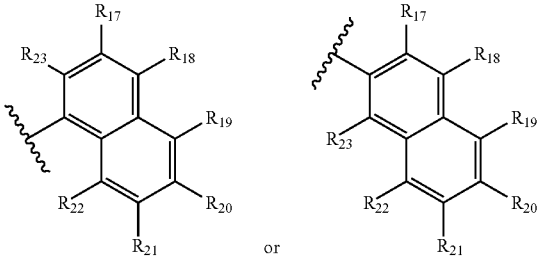

In some embodiments, the compound wherein $R_{13}$ is wherein each of X, Y, X are independently, H, halogen, —NO$_2$, —CN, —NH$R_{15}$, —N$R_{15}R_{16}$, —S$R_{15}$, —SO$_2R_{15}$, —O$R_{15}$, —CO$_2R_{15}$, CF$_3$, -alkyl-N$R_{15}R_{16}$, -alkyl-O$R_{15}$, C$_{1-10}$ alkyl, C$_{2-10}$ alkenyl, C$_{2-10}$ alkynyl, aryl, heteroaryl, or heterocyclyl;

wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl;

In some embodiments, the compound having the structure:

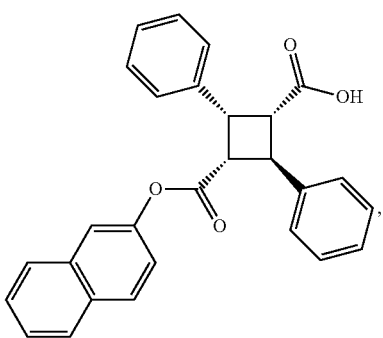

-continued
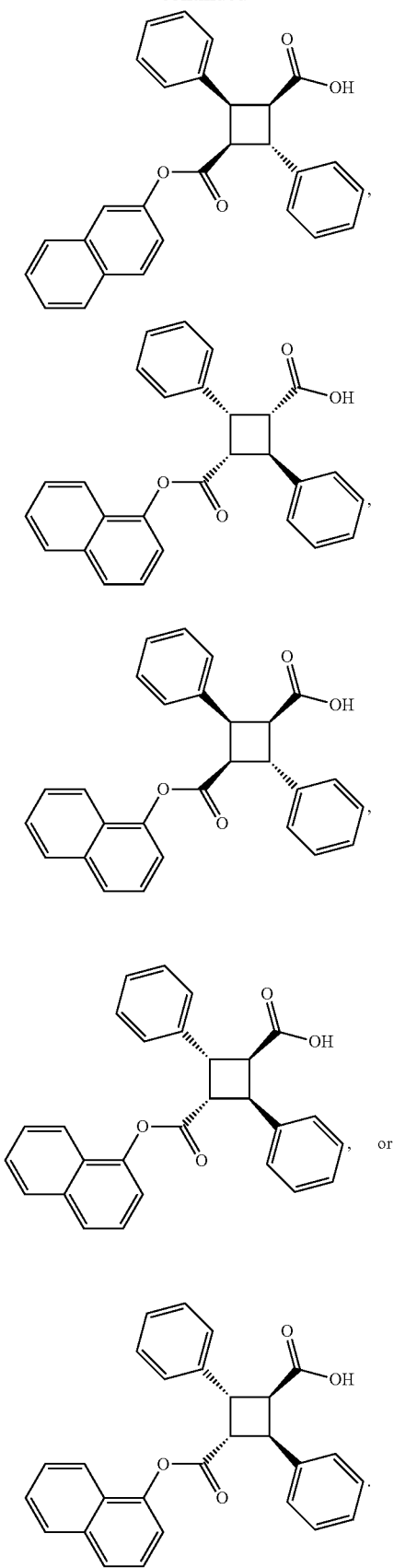
or
In some embodiments, the compound having the structure:
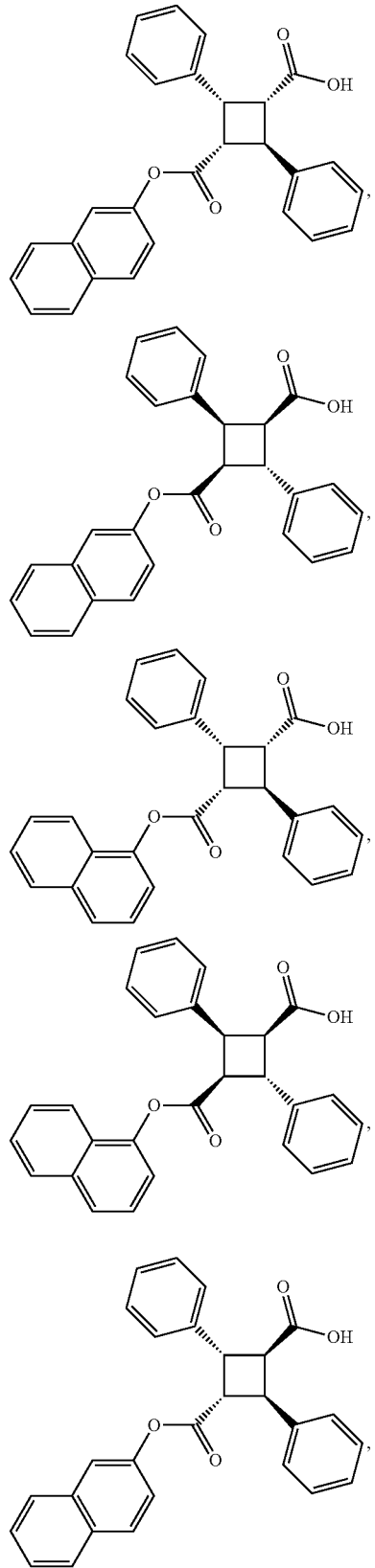

-continued
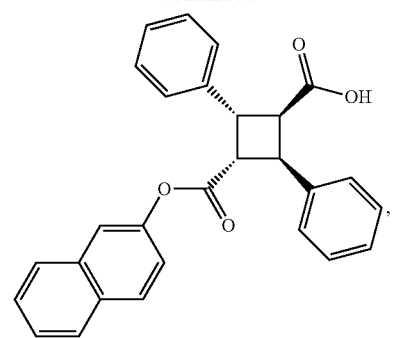
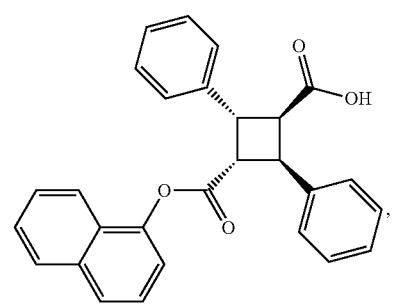
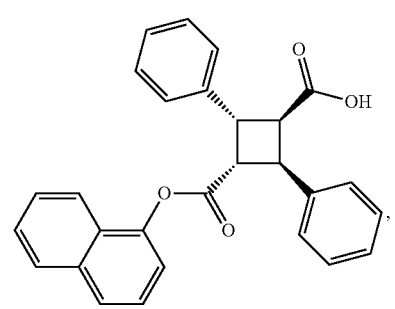
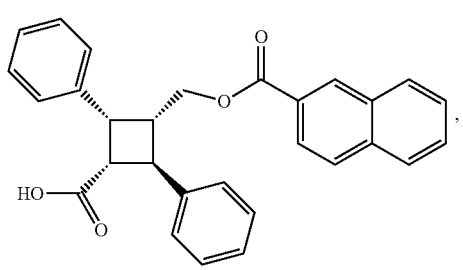
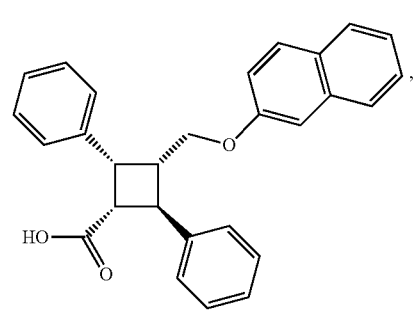
-continued
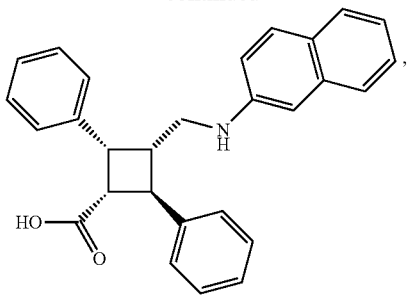
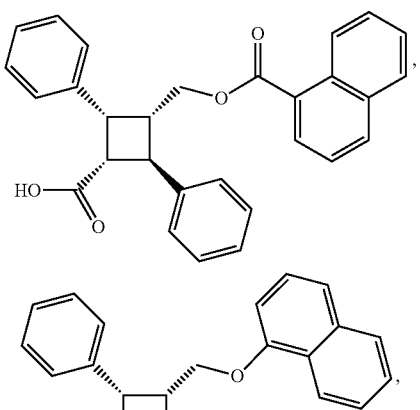
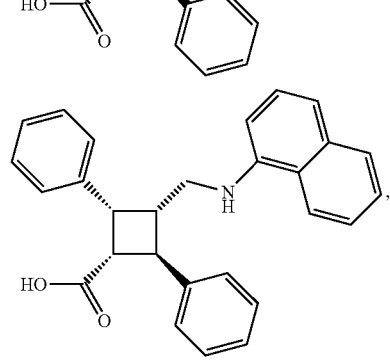
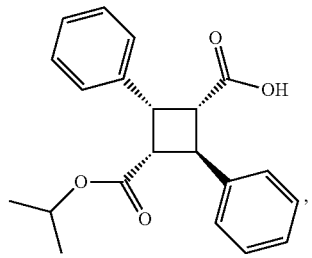
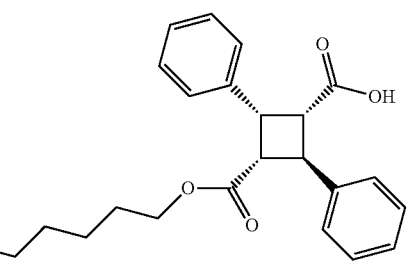
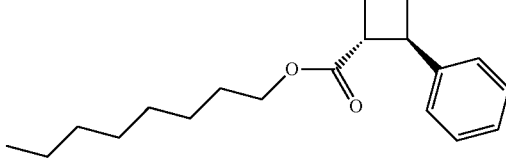

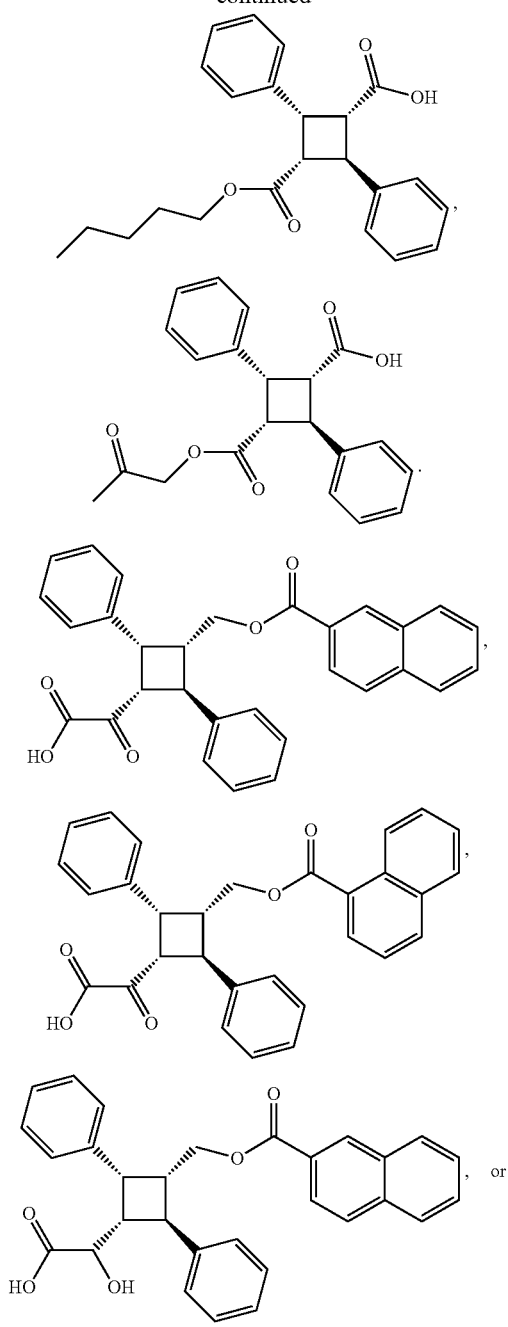
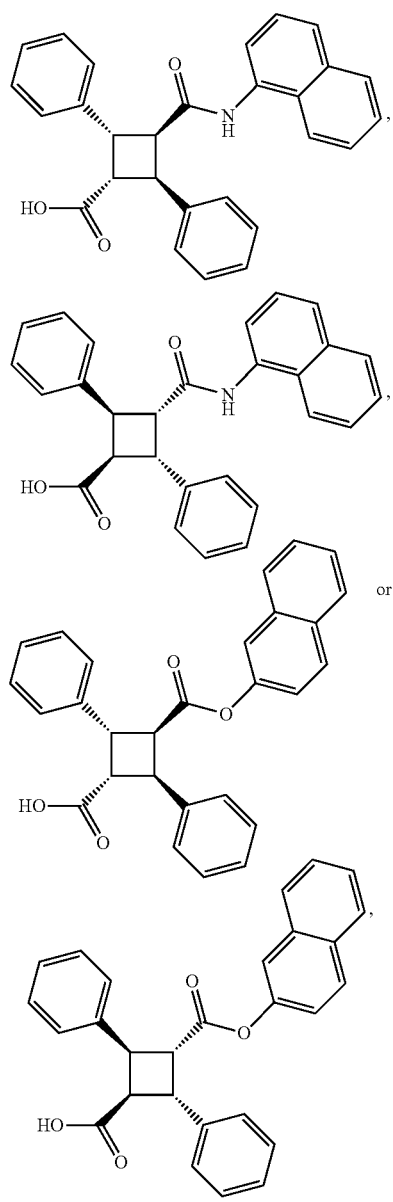
or an enantiomer or pharmaceutically acceptable salt thereof.
The present invention provides a process for producing the compound of the present invention comprising:
(a) contacting a compound having the structure:
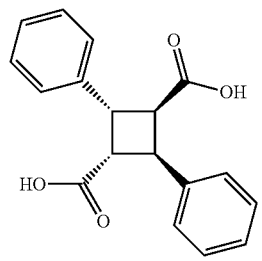 [SMILES: O=C(O)[C@H]1[C@H](c2ccccc2)[C@H](C(=O)O)[C@H]1c1ccccc1]
In some embodiments, the invention provides a compound having the structure:
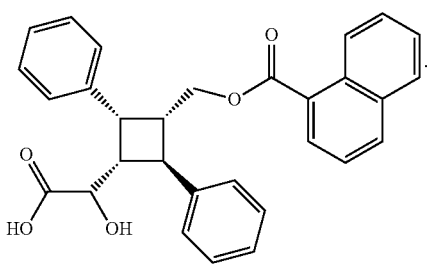

with acetic anhydride in the presence of sodium acetate so as to produce a compound having the structure:

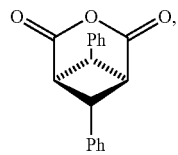

(b) reacting the product of step (a) with a nucleophile (Nuc) in a first suitable solvent in the presence of an amine base so as to produce a mixture of enantiomers having the structures:

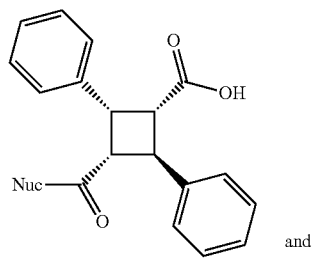

and

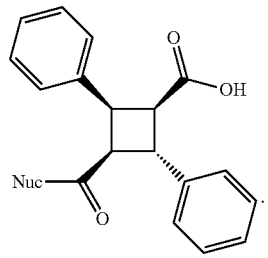

In some embodiments, the method wherein the nucleophile used in step (b) is

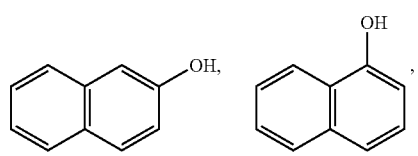

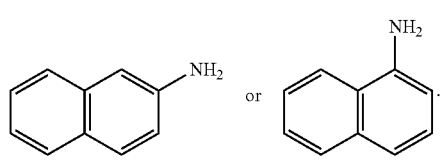

or

In some embodiments, the method wherein the nucleophile used in step (b) is a chiral nucleophile.

In some embodiments, the method wherein the nucleophile used in step (b) is (S)-(−)-1-phenylethanol.

In some embodiments, the method further comprising separating the diastereomeric products of step (b).

In some embodiments, the method wherein the products of step (b) are

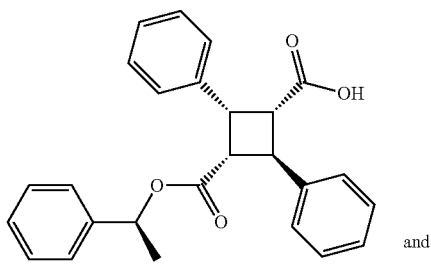

and

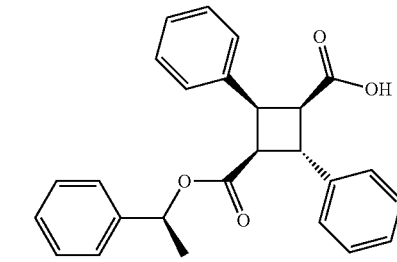

In some embodiments, the method further comprising (c) separating the diastereomeric products of step (b) to produce enantiopure compounds having the structure:

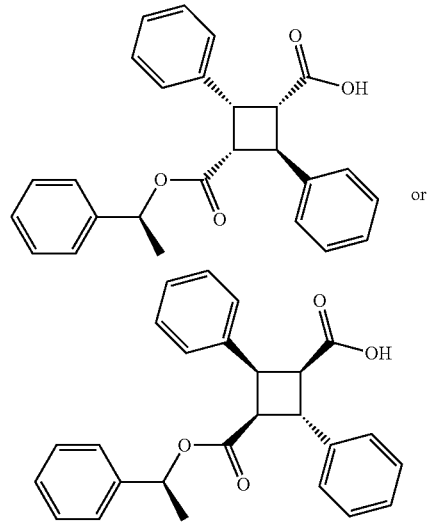

(d) reacting a product of step (c) with a coupling reagent in the presence of a nucleophile in a second suitable solvent so as to produce enantiopure compounds having the structure:

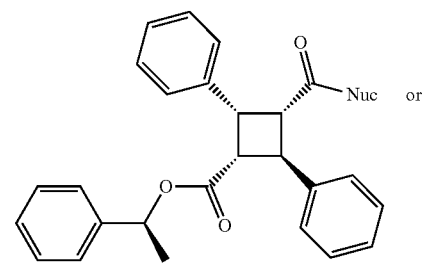

or

-continued

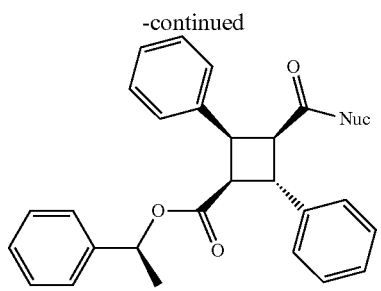

(e) reacting the product of step (d) with hydrogen in the presence of palladium on carbon to produce an enantiopure compound having the structure:

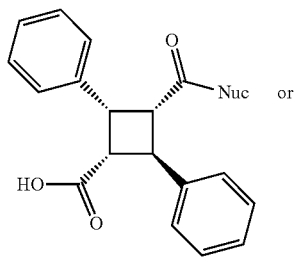

or

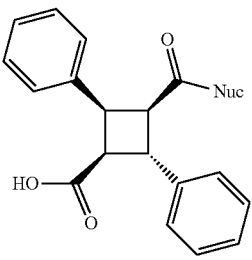

In some embodiments, the method wherein the nucleophile used in step (d) is

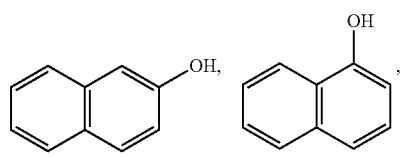

or

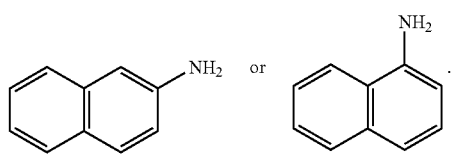

In some embodiments of the above process, the compound produced has the structure:

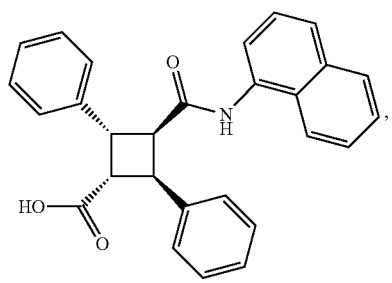

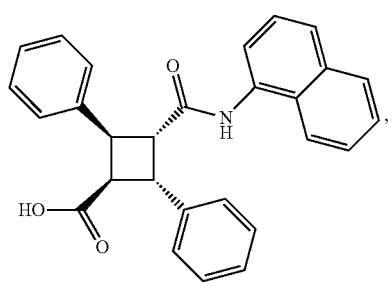

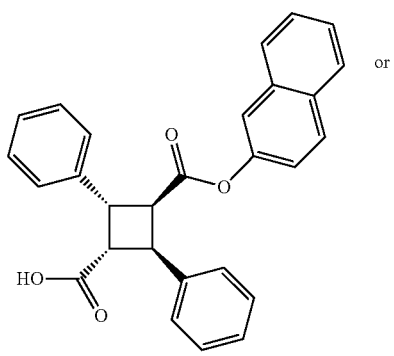

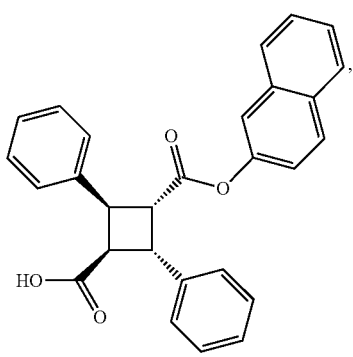

or an enantiomer thereof.

The present invention provides a method of inhibiting the activity of a Fatty Acid Binding Protein (FABP) comprising contacting the FABP with a compound having the structure:

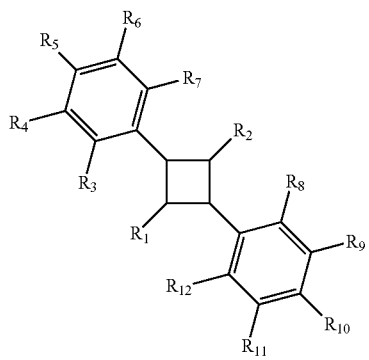

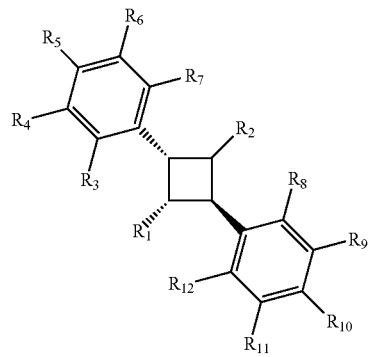

wherein $R_1$ and $R_2$ are different and are each —C(=O)$R_3$, —C(=O)O$R_{13}$, —C(=O)N$R_{13}R_{14}$, -alkyl-C(=O)$R_{13}$, -alkyl-C(=O)O$R_{13}$, -alkyl-C(=O)N$R_{13}R_{14}$, -alkyl-OC(=O)O$R_{13}$, -alkyl-OC(=O)O$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)$R_{13}$, -alkyl-NHC(=O)N$R_{13}R_{14}$, -alkyl-NHC(=S)N$R_{13}R_{14}$, -alkyl-NHC(=N$R_{13}$)N$R_{13}R_{14}$, —C(—OH)C(=O)O$R_{13}$, —C(=O)C(=O)O$R_{13}$ or —C≡C—$R_{13}$, wherein $R_{13}$ and $R_{14}$ are each, independently, H, $CF_3$, $C_{1-10}$ alkyl, $C_{2-10}$ alkenyl, $C_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —$NO_2$, —CN, —NH$R_{15}$, —N$R_{15}R_{16}$, —S$R_{15}$, —$SO_2R_{15}$, —O$R_{15}$, —$CO_2R_{15}$, $CF_3$, -alkyl-NH$R_{15}$, -alkyl-N$R_{15}R_{16}$, -alkyl-O$R_{15}$, $C_{1-10}$ alkyl, $C_{2-10}$ alkenyl, $C_{2-10}$ alkynyl, aryl, heteroaryl, or heterocyclyl;

wherein $R_{15}$ and $R_{16}$ are each, independently, H, $CF_3$, $C_{1-10}$ alkyl, $C_{2-10}$ alkenyl, $C_{2-10}$ alkynyl, heteroalkyl, aryl, heteroaryl, or heterocyclyl;

when one of $R_1$ or $R_2$ is —C(=O)OH or —C(=O)O$CH_3$, then the other of $R_1$ or $R_2$ is other than —C(=O)O$R_{13}$ where $R_{13}$ is alkyl, heteroalkyl, substituted phenyl or benzyl, —C(=O)NH$R_{13}R_{14}$ where one of $R_{13}$ or $R_{14}$ is —H, phenyl or substituted phenyl and the other is —H, or —C(=O)N$R_{13}R_{14}$ where $R_{13}$ and $R_{14}$ combine to form a piperidine or morpholine;

or a pharmaceutically acceptable salt thereof.

In some embodiments of the method of inhibiting the activity of a Fatty Acid Binding Protein (FABP), wherein when one of $R_1$ or $R_2$ is —C(=O)OH or —C(=O)O$CH_3$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is alkyl, heteroalkyl, substituted phenyl or benzyl, —C(=O)NH$R_{13}R_{14}$ where one of $R_{13}$ or $R_{14}$ is —H, phenyl or substituted phenyl and the other is —H, or —C(=O)N$R_{13}R_{14}$ where $R_{13}$ and $R_{14}$ combine to form a piperidine or morpholine.

In some embodiments of the method of inhibiting the activity of a Fatty Acid Binding Protein (FABP), wherein the compound has the structure:

wherein $R_1$ and $R_2$ are different and are each —C(=O)$R_{13}$, —C(=O)O$R_{13}$, —C(=O)N$R_{13}R_{14}$, -alkyl-C(=O)$R_{13}$, -alkyl-C(=O)O$R_{13}$, -alkyl-C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)$R_{13}$, -alkyl-NHC(=O)N$R_{13}R_{14}$, -alkyl-NHC(=S)N$R_{13}R_{14}$, -alkyl-NHC(=N$R_{13}$)N$R_{13}R_{14}$, —C(—OH)C(=O)O$R_{13}$, —C(=O)C(=O)O$R_{13}$ or —C≡C—$R_{13}$, wherein $R_{13}$ and $R_{14}$ are each, independently, H, $CF_3$, $C_{1-10}$ alkyl, $C_{2-10}$ alkenyl, $C_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —$NO_2$, —CN, —NH$R_{15}$, —N$R_{15}R_{16}$, —S$R_{15}$, —$SO_2R_{15}$, —O$R_{15}$, —$CO_2R_{15}$, $CF_3$, -alkyl-N$R_{15}R_{16}$, -alkyl-O$R_{15}$, $C_{1-10}$ alkyl, $C_{2-10}$ alkenyl, $C_{2-10}$ alkynyl, aryl, heteroaryl, or heterocyclyl;

wherein $R_{15}$ and $R_{16}$ are each, independently, H, $CF_3$, $C_{1-10}$ alkyl, $C_{2-10}$ alkenyl, $C_{2-10}$ alkynyl, heteroalkyl, cycloheteroalkyl, aryl, heteroaryl, or heterocyclyl;

when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is —$CH_3$, —$CH_2CH_3$, —$(CH_2)_4CH_3$, —$(CH_2)_7CH_3$, —$CH(CH_3)_2$, —$CH_2C(O)CH_3$, tolyl, 1-Naphthol or propyl 1-bromo-1-methylpropanoyloxybutyl ester, or —C(=O)N$R_{13}R_{14}$ where one of $R_{13}$ or $R_{14}$ is phenyl and the other is —H, or both of $R_{13}$ and $R_{14}$ are —H; and when one of $R_1$ or $R_2$ is —C(=O)O$CH_3$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)N$R_{13}R_{14}$ where one of $R_{13}$ and $R_{14}$ is —H and the other is (2-methylmercapto)phenyl;

or an enantiomer or pharmaceutically acceptable salt thereof.

In some embodiments of the method of inhibiting the activity of a Fatty Acid Binding Protein (FABP), wherein the compound has the structure:

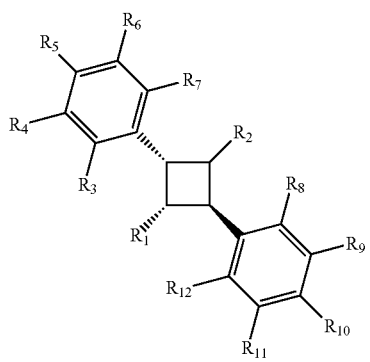

wherein
$R_1$ and $R_2$ are different and are each —C(=O)$R_{13}$, —C(=O)O$R_{13}$, —C(=O)N$R_{13}R_{14}$, -alkyl-C(=O)$R_{13}$, -alkyl-C(=O)O$R_{13}$, -alkyl-C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)$R_{13}$, -alkyl-NHC(=O)N$R_{13}R_{14}$, -alkyl-NHC(=S)N$R_{13}R_{14}$, -alkyl-NHC(=N$R_{13}$)N$R_{13}R_{14}$, —C(—OH)C(=O)O$R_{13}$, —C(=O)C(=O)O$R_{13}$ or —C≡C—$R_{13}$, wherein $R_{13}$ and $R_{14}$ are each, independently, H, CF$_3$, C$_{1-10}$ alkyl, C$_{2-10}$ alkenyl, C$_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —NO$_2$, —CN, —NH$R_{15}$, —N$R_{15}R_{16}$, —S$R_{15}$, —SO$_2R_{15}$, —O$R_{15}$, —CO$_2R_{15}$, CF$_3$, -alkyl-NH$R_{15}$, -alkyl-N$R_{15}R_{16}$, -alkyl-O$R_{15}$, C$_{1-10}$ alkyl, C$_{2-10}$ alkenyl, C$_{2-10}$ alkynyl, aryl, heteroaryl, or heterocyclyl;

wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl;

when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is —CH$_3$, —CH$_2$CH$_3$, tolyl or propyl 1-bromo-1-methylpropanoyloxybutyl ester, or —C(=O)N$R_{13}R_{14}$ where one of $R_{13}$ or $R_{14}$ is phenyl and the other is —H, or both of $R_{13}$ and $R_{14}$ are —H; and when one of $R_1$ or $R_2$ is —C(=O)OCH$_3$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)N$R_{13}R_{14}$ where one of $R_{13}$ and $R_{14}$ is —H and the other is (2-methylmercapto)phenyl;

or an enantiomer or pharmaceutically acceptable salt thereof.

In some embodiments of any of the above methods, the compound having the structure:

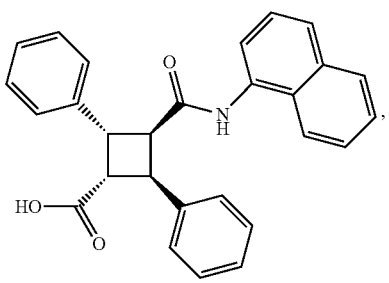

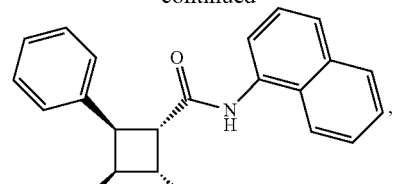

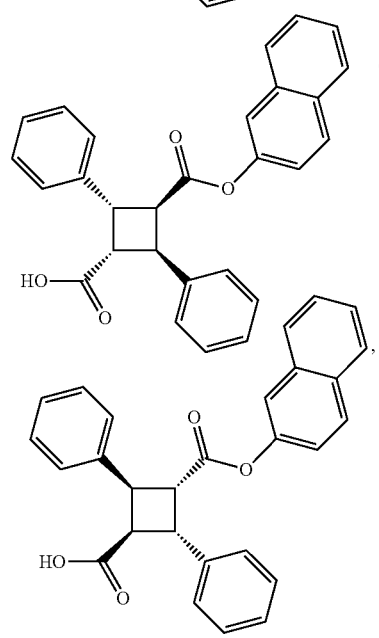

or an enantiomer or pharmaceutically acceptable salt thereof.

In some embodiments of the method of inhibiting the activity of a Fatty Acid Binding Protein (FABP), wherein the compound inhibits binding of an FABP ligand to the FABP.

In some embodiments of the method of inhibiting the activity of a Fatty Acid Binding Protein (FABP), wherein the FABP ligand is an endocannabinoid ligand.

In some embodiments of the method of inhibiting the activity of a Fatty Acid Binding Protein (FABP), wherein the FABP ligand is anandamide (AEA) or 2-arachidonoylglycerol (2-AG).

The present invention provides a method of identifying an agent that inhibits the activity of a Fatty Acid Binding Protein (FABP) comprising contacting a Fatty Acid Binding Protein (FABP) expressed in the CNS with the agent and separately with a compound having the structure

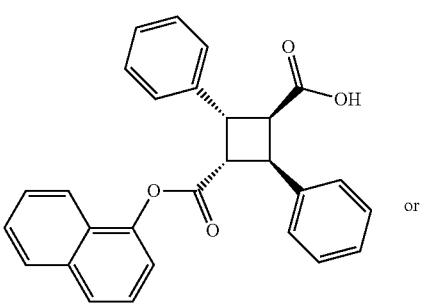

-continued

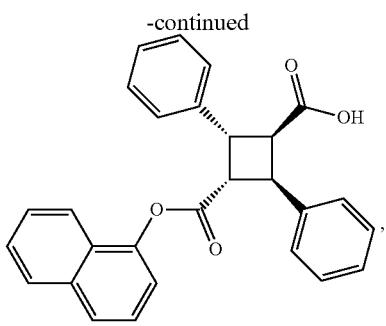

and comparing the FABP inhibitory activity of the agent with the FABP inhibitory activity of the compound to identify an agent where FABP inhibitory activity is greater than that of the compound.

In some embodiments, a method of inhibiting the activity of a Fatty Acid Binding Protein (FABP) comprising contacting the FABP with a compound having the structure:

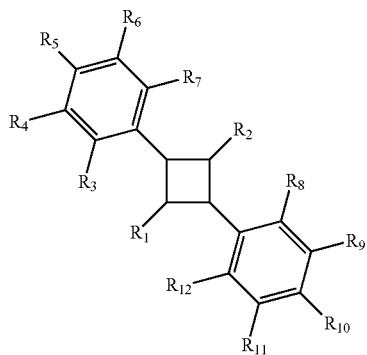

wherein $R_1$ and $R_2$ are each independently —C(=O)$R_{13}$, —C(=O)O$R_{13}$, —C(=O)N$R_{13}R_{14}$, -alkyl-C(=O)$R_{13}$, -alkyl-C(=O)O$R_{13}$, -alkyl-C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)$R_{13}$, -alkyl-NHC(=O)N$R_{13}R_{14}$, -alkyl-NHC(=S)N$R_{13}R_{14}$, -alkyl-NHC(=N$R_{13}$)N$R_{13}R_{14}$, —C(—OH)C(=O)O$R_{13}$, —C(=O)C(=O)O$R_{13}$ or —C≡C—$R_{13}$, wherein $R_{13}$ and $R_{14}$ are each, independently, H, $CF_3$, $C_{1-10}$ alkyl, $C_{2-10}$ alkenyl, $C_{2-10}$ alkynyl, heteroalkyl, cycloalkyl, aryl, heteroaryl, heterocyclyl or combine to form a cycloalkyl or heterocyclyl;

$R_3$, $R_4$, $R_5$, $R_6$, $R_7$, $R_8$, $R_9$, $R_{10}$, $R_{11}$ and $R_{12}$ are each independently, H, halogen, —$NO_2$, —CN, —$NHR_{15}$, —$NR_{15}R_{16}$, —$SR_{15}$, —$SO_2R_{15}$, —$OR_{15}$, —$CO_2R_{15}$, $CF_3$, -alkyl-$NHR_{15}$, -alkyl-$NHR_{15}R_{16}$, -alkyl-$OR_{15}$, $C_{1-10}$ alkyl, $C_{2-10}$ alkenyl, $C_{2-10}$ alkynyl, aryl, heteroaryl, or heterocyclyl;

wherein $R_{15}$ and $R_{16}$ are each, independently, H, $CF_3$, $C_{1-10}$ alkyl, $C_{2-10}$ alkenyl, $C_{2-10}$ alkynyl, heteroalkyl, aryl, heteroaryl, or heterocyclyl;

or a pharmaceutically acceptable salt thereof.

The following compounds are available from ChemDiv (San Diego, Calif., USA):

| Structure | ChemDiv ID Number |
|---|---|
| 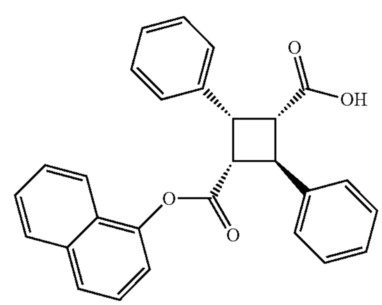 [SMILES: O=C(O)[C@H]1[C@@H](c2ccccc2)[C@@H](C(=O)Oc2cccc3ccccc23)[C@@H]1c1ccccc1] | 8009-2334 |
| 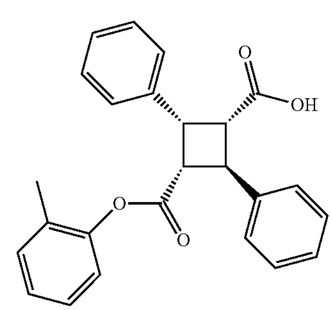 [SMILES: Cc1ccccc1OC(=O)[C@H]1[C@H](c2ccccc2)[C@@H](C(=O)O)[C@H]1c1ccccc1] | 8009-3434 |

-continued

| Structure | ChemDiv ID Number |
|---|---|
| 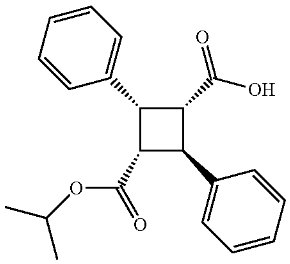 [SMILES: CC(C)OC(=O)[C@H]1[C@H](c2ccccc2)[C@@H](C(=O)O)[C@H]1c1ccccc1] | 8010-1995 |
| 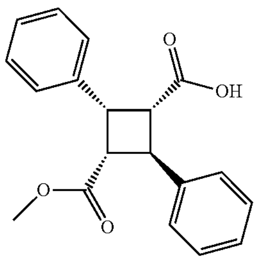 [SMILES: COC(=O)[C@H]1[C@H](c2ccccc2)[C@@H](C(=O)O)[C@H]1c1ccccc1] | 8010-1996 |
| 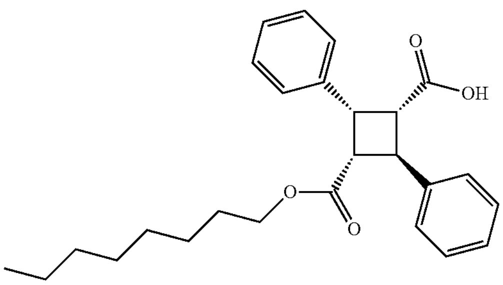 [SMILES: CCCCCCCCOC(=O)[C@H]1[C@H](c2ccccc2)[C@@H](C(=O)O)[C@H]1c1ccccc1] | 8010-1997 |
| 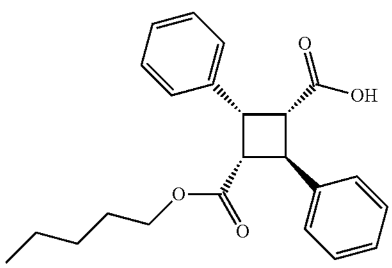 [SMILES: CCCCCOC(=O)[C@H]1[C@H](c2ccccc2)[C@@H](C(=O)O)[C@H]1c1ccccc1] | 8008-6749 |
| 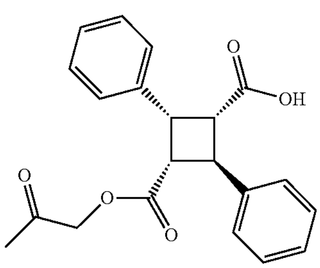 [SMILES: CC(=O)COC(=O)[C@H]1[C@H](c2ccccc2)[C@@H](C(=O)O)[C@H]1c1ccccc1] | 8008-8584 |

In some embodiments, a method of treating a neurological disorder affects at least one of movement, memory, mood, appetite, nociception, endocrine regulation, thermoregulation, sensory perception, or cognitive functions.

In some embodiments, a method of treating a neurological disorder associated with drug addiction, depression, compulsive behavior, neuropathic pain, or a movement disorder.

In some embodiments, a method of treating drug addiction, depression, compulsive behavior, neuropathic pain, inflammatory pain, or a movement disorder.

In some embodiments, a method of treating pain, neuropathic pain, or inflammatory pain.

As used herein, the term "endocannabinoid" includes any molecule that activates cannabinoid receptors. Examples of such receptors are CB1 and CB2. Examples of endocannabinoids are arachidonoyl ethanolamide (AEA) and 2-arachidonoyl glycerol (2-AG).

As used herein, the term "fatty acid binding protein" or "FABP" refers to fatty acid binding proteins (FABPs) that function as intracellular carriers that shuttle cannabinoids (and by extension fatty acid amides (FAAs)) to FAAH where cannabinoids are hydrolyzed and degraded. Further, uptake of endocannabinoids (and by extension FAAs) by the cell and the subsequent hydrolysis of endocannabinoids (and by extension FAAs) are enhanced by FABPs, and inhibiting the interaction of endocannabinoids (and by extension FAAs) with FABPs reduces endocannabinoid (and by extension FAA) uptake and hydrolysis. FABPS include, for example, fatty acid binding protein 1 (FABP 1), fatty acid binding protein 2 (FABP 2), fatty acid binding protein 3 (FABP 3), fatty acid binding protein 4 (FABP 4), fatty acid binding protein 5 (FABP 5), fatty acid binding protein 6 (FABP 6), fatty acid binding protein 7 (FABP 7), fatty acid binding protein 8 (FABP 8), fatty acid binding protein 9 (FABP 9), fatty acid binding protein 10 (FABP 10), fatty acid binding protein 11 (FABP 11), fatty acid binding protein 5-like (FABP 5-like 1), fatty acid binding protein 5-like 2 (FABP 5-like 2), fatty acid binding protein 5-like 3 (FABP 5-like 3), fatty acid binding protein 5-like 4 (FABP 5-like 4), fatty acid binding protein 5-like 5 (FABP 5-like 5), fatty acid binding protein 5-like 6 (FABP 5-like 6), and fatty acid binding protein 5-like 7 (FABP 5-like 7) (see Chmurzynska et al. 2006 and PCT International Application Publication No. WO 2010/083532 A1, the contents of each of which are hereby incorporated by reference).

As used herein, the term "therapeutic agent" refers to any agent used to treat a disease or that provides a beneficial therapeutic effect to a subject.

As used herein, the phrase "inhibits the interaction" is employed herein to refer to any disruption, partial or total, of the natural effect of FABPs on the metabolism of endocannabinoids.

As used herein, the term "activity" refers to the activation, production, expression, synthesis, intercellular effect, and/or pathological or aberrant effect of the referenced molecule, either inside and/or outside of a cell. Such molecules include, but are not limited to, cytokines, enzymes, growth factors, pro-growth factors, active growth factors, and pro-enzymes. Molecules such as cytokines, enzymes, growth factors, pro-growth factors, active growth factors, and pro-enzymes may be produced, expressed, or synthesized within a cell where they may exert an effect. Such molecules may also be transported outside of the cell to the extracellular matrix where they may induce an effect on the extracellular matrix or on a neighboring cell. It is understood that activation of inactive cytokines, enzymes and pro-enzymes may occur inside and/or outside of a cell and that both inactive and active forms may be present at any point inside and/or outside of a cell. It is also understood that cells may possess basal levels of such molecules for normal function and that abnormally high or low levels of such active molecules may lead to pathological or aberrant effects that may be corrected by pharmacological intervention.

As used herein, "treating" means reducing, slowing, stopping, preventing, reversing, or in any way improving the progression of a disease or disorder or a symptom of the disease or disorder.

In some embodiments, the compounds of the present invention include all hydrates, solvates, and complexes of the compounds used by this invention.

In some embodiments, if a chiral center or another form of an isomeric center is present in a compound of the present invention, all forms of such isomer or isomers, including enantiomers and diastereomers, are intended to be covered herein.

In some embodiments, if a chiral center or another form of an isomeric center is present in a compound of the present invention, only enantiomeric forms are intended to be covered herein.

Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers.

As used herein, "enantiomers" are non-identical, non-superimposible mirror images of each other. For any given chiral compound, only one pair of enantiomers exists. The enantiomers can be separated using known techniques, including those described in Pure and Applied Chemistry 69, 1469-1474, (1997) IUPAC.

In cases in which compounds have unsaturated carbon-carbon double bonds, both the cis (Z) and trans (E) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2$H and/or wherein the isotopic atom $^{13}$C. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include individual groups each having 1, 2, . . . , n–1 or n carbons in a linear or branched arrangement. For example, $C_1$-$C_6$, as in "$C_1$-$C_6$ alkyl" is defined to include individual groups each having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "alkylryl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as a substituent on the alkyl group. Examples of alkylheteroaryl moieties include, but are not limited to, —CH$_2$—(C$_5$H$_4$N), —CH$_2$—CH$_2$—(C$_5$H$_4$N) and the like.

The term "heterocycle" or "heterocyclyl" refers to a mono- or polycyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different.

The term "tolyl" refers to one of the three CH$_3$C$_6$H$_4$— isomeric groups derived from toluene.

The term "piperidine" refers to a heterocyclic amine consists of a six-membered ring containing five methylene units and one nitrogen atom.

The term "morpholine" refers to a heterocyclic amine consists of a six-membered ring containing four methylene units, one nitrogen atom and one oxygen atom, wherein there are two pairs of methylene units linking the nitrogen atom and oxygen atom.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity. The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, asuitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Materials and Methods

Those having ordinary skill in the art of organic synthesis will appreciate that modifications to general procedures and synthetic routes contained in this application can be used to yield additional derivatives and structurally diverse compounds. Suitable organic transformations are described in March's Advanced Organic Chemistry: Reactions, Mechanisms, and Structure (Wiley-Interscience; 6th edition, 2007), the content of which is hereby incorporated by reference.

Chemicals

12-NBD-stearate [12-N-methyl-(7-nitrobenz-2-oxa-1,3-diazo) aminostearic acid] was from Avanti Polar Lipids (Alabaster, Ala.). BMS309403 was from EMD Chemicals (San Diego, Calif.). Arachidonic acid was from Cayman Chemical (Ann Arbor, Mich.). 48 virtually screened test compounds from ChemDiv, Inc. (Moscow, Russia). α-Truxillic acid 1-naphthyl ester (Compound 26) and γ-truxillic acid 1-naphthyl ester (Compound 49) were synthesized at the Institute of Chemical Biology and Drug Discovery, Stony Brook University.

High Throughput Fluorescence Displacement Assay with NBD-Stearate

FABP5 was purified and delipidated as described previously (Kaczocha, M. et al. 2012). FABP5 (30 µg), NBD-stearate (1 µM), and a competitor test compound were incubated in 30 mM Tris-HCl, 100 mM NaCl buffer (pH 7.6). Competitors included arachidonic acid, BMS309403, 48 test compounds from ChemDiv library, Compound 26 and Compound 49. The initial assay was run with buffer (30 mM Tris-HCl buffer), negative controls (buffer and NBD-stearate), positive controls (buffer, NBD-stearate, FABP5), and experimental wells with a variable test compound added (arachidonic acid or one of the 48 test compounds) at 10 µM. Test compounds that produced high inhibition and proved statistically significant were then added to the fluorescent assay at 10 µM and tested in triplicate to verify their success. The most effective test compound and BMS309403 were measured in increasing concentrations (0.01-50 µM), as were the Compound 26 and γ-truxillic acid 1-naphthyl ester, which were discovered following the test. The fluorescent assays were tested in the wells of Microtest 96-well Assay Plates, Optilux (BD Biosciences, Franklin Lakes, N.J.) and loss of fluorescence intensity was measured with a FLUOstar OPTIMA spectrofluorometer set to excitation and emission wavelengths of 460 nm and 544 nm, respectively. For the most effective test compounds, $IC_{50}$ values were calculated with GraphPad Prism. GraphPad Prism was also used to determine the $K_i$ of these select competitors from the equation $K_i=IC_{50}/(1+([NBD\text{-stearate}]/K_d))$. The $K_d$ of NBD-stearate for FABP5 had been determined previously through incubating FABP5 with increasing concentrations of NBD-stearate. One site binding analysis in GraphPad Prism indicated that the $K_d$ of NBD-stearate for FABP5 was 0.16 μM (Kaczocha, M. et al. 2012).

Patch-Clamp Electrophysiology in Brain Slices

Whole-cell-voltage clamp recordings of dorsal raphe (DR) serotonin (5-HT) neurons were performed as previously described [33]. Briefly, DR neurons were visualized using an upright microscope (BX 51 WI, Olympus, Tokyo, Japan) equipped with a differential interference contrast and infrared imaging system. Somatic recordings from DR neurons were obtained with path electrodes (3-5 mΩ) backfilled with potassium gluconate based internal solution of the following composition: 120 mM potassium gluconate, 10 mM KCl, 10 mM $Na_2$-phosphocreatine, 10 mM HEPES, 1 mM $MgCl_2$, 1 mM EGTA, 2 mM $Na_2$-ATP, 0.25 mM Na-GTP, pH 7.3 (Adjusted with KOH; Osmolarity, 280 to 290 mOsmol/l). All the recordings were conducted in the presence of $GABA_A$ receptor antagonist picrotoxin (100 μM). Excitatory postsynaptic currents (EPSCs) were evoked with a single square stimulus (intensity, 1 to 10 V, duration, 100 to 200 μs) delivered via a glass stimulating electrode. EPSCs were amplified with a Multiclamp 700B (Molecular Devices, Union City, Calif., USA) and acquired using pClamp 10 software (Molecular Devices).

Data Analysis

The amplitude of EPSCs was determined by measuring the average current during a 2-ms period at the peak of each EPSC and subtracted from the baseline current determined during a 5-ms time window before the stimulus. All EPSC amplitudes were normalized to the mean baseline amplitude recorded for at least 10 min before drug application. Results in the text and figures are presented as mean±SEM. Statistical analysis was conducted using the Student's paired t-test.

AEA Uptake

AEA uptake assays in wild-type and FABP5 knockdown HeLa cells were performed exactly as described (Kaczocha, M. et al. 2012).

FAAH Enzyme Assay

Enzyme assays measuring the hydrolysis of [$^{14}$C]AEA in the presence of Compound 26 or the FAAH inhibitor URB597 were carried out in HeLa homogenates expressing rat FAAH as described (Kaczocha, M. et al. 2009).

PPAR Transactivation

PPARα and PPARγ transactivation assays were performed in HeLa cells exactly as described (Kaczocha, M. et al. 2012). Briefly, cells were transfected with the PPAR reporter system, incubated with GW7647, rosiglitazone, or Compound 26 for 6 hrs, followed by measurement of luciferase and β-galactosidase activity using a luminometer as described (Kaczocha, M. et al. 2012).

Animals

We used male C57B16 mice (22-30 g, Taconic Farms) for all experiments. The animals were group housed at room temperature and kept on a 12:12 hour light:dark cycle with ad libitum access to water and food. The animals were habituated to the experimental room for one week before testing. All experiments were approved by the Stony Brook University Institutional Animal Care and Use Committee. The experimenter was blinded to the treatment conditions of each animal.

Carrageenan-Induced Paw Edema and Thermal Hyperalgesia

Paw edema was induced by injecting 1% λ-carrageenan (20 μl, in sterile saline) into the plantar surface of the left hind paw and a control solution of saline into the right hind paw using a 27 gauge needle. Paw diameters were measured before carrageenan injection and 4 hours after injection using digital electronic calipers (Fisher) and expressed to the nearest ±0.01 mm. Compound 26 (20 mg/kg, i.p.) was dissolved in ethanol:emulphor:saline (1:1:18), requiring sonication and gentle heating for solubilization, and administered 45 min prior to injection of carrageenan. The cannabinoid receptor antagonists, rimonabant and SR144528 (3 mg/kg, i.p.), in ethanol:emulphor:saline (1:1:18), were injected 15 min before the FABP inhibitor. Edema is reported as the change in paw diameter at 4 hr over the baseline. Changes in paw diameter of saline-injected contralateral paws were negligible. Thermal hyperalgesia measured the latency to withdraw the paw from a focused beam of radiant heat applied to the plantar surface of the hind paw using a Hargreaves plantar apparatus (Ugo Basile) set at an intensity of 3.0. For each mouse, the average latencies consisted of three trials spaced at least 5 minutes apart. The mice were habituated to the test chamber for 30 min. The cutoff time was set at 30 sec.

Formalin Test

Mice were habituated to the observation chamber (Plexiglas box, 25 cm×25 cm×25 cm) for 30 min prior to formalin injection. The mice subsequently received an injection of formalin (2.5% in saline, 20 μl) into the plantar surface of the right hind paw using a 27 gauge needle. The animals were immediately placed back into the observation chamber and nocifensive behavior (time spent licking or biting the paw) was recorded for 60 min. The formalin test consists of two phases with the first phase (0-5 min) reflecting nociceptor activation and the second phase (15-45 min) reflecting an inflammatory pain response.

Statistical Analyses

Behavioral data are presented as means±S.E.M. for the vehicle and inhibitor-treated groups, each consisting of at least 6 animals. Statistical significance between vehicle and inhibitor groups was determined using unpaired t-tests or one-way ANOVA followed by Dunnett's post hoc analysis. In all cases, differences of p<0.05 were considered significant.

High-Throughput Virtual Screening

A high-throughput virtual screening of over one million molecules from the ChemDiv subset of the ZINC database (http://zinc.docking.org) was conducted on New York Blue, an 18 rack IBM Blue Gene/L massively parallel supercomputer located at Brookhaven National Laboratory using DOCK version 6.5. Prior to docking, the most updated ChemDiv database was downloaded and presorted by rotatable bonds and split into 10 subsets of ~100,000 molecules using the DOCK database filter. Subsequently, an energy grid for FABP7 (PDB:1FE3) was generated using the grid program. Then, each molecule was flexibly docked to the FABP7 grid (DOCK FLX protocol) and the single lowest-energy pose was retained.

Footprint-Based Rescoring

Following the high-throughput virtual screening, footprint-based rescoring methodology developed by Rizzo and colleagues was implemented to enrich the library of docked molecules. First, the co-crystallized ligand oleic acid (reference) was minimized on the receptor Cartesian coordinates within the binding pocket. This was implemented using both a hydrogen optimization followed by a weak restrained minimization (restraint of 10 kcal/mol). Following reference minimization, each molecule of the docked library was subsequently minimized in Cartesian space using the restrained minimization protocol. Last, electrostatic, van der Waals, and hydrogen bond footprint similarity scores were computed using normalized Euclidian distance for each molecule docked versus the reference using DOCK 6.5.

Database Clustering and Compound Selection

First, subsets 1 through 5 and subset 6 through 10 containing ~500,000 molecules were rank-ordered by the DOCK Cartesian energy (DCE) score. The top 45,000 of each combined subset of 500,000 molecules (~10% total 90,000 molecules) were then clustered using MACCS fingerprints, as implemented in the program MOE with the tanimoto coefficient of 0.75. The resulting cluster heads obtained were then further rank-ordered by: (i) standard DOCK score ($DCE_{VDW+ES}$), (ii) van der Waals footprint similarity score ($FPS_{VDW}$), (iii) electrostatic footprint similarity score ($FPS_{ES}$), (iv) H-bond footprint similarity score ($FPS_{HB}$), (v) the sum of van der Waals and electrostatic footprint similarity score ($FPS_{VDW+ES}$). The top 250 molecules rank-ordered by each criteria were then plotted in MathPlotLib and examined by visual inspection and consistency to the reference footprint. This method of analysis allowed us to both visually see key interactions within the binding pocket while simultaneously observing the magnitudes of those key interactions within the footprints for each molecule. Based on this approach, 48 compounds were selected a purchased for biological testing against FABP5. Biological screening of these compounds for activity against FABP7 is underway.

Redocking of FABP7 Hit Compounds into FABP5

The 48 molecules selected from the previous FABP7 virtual screening were redocked using DOCK version 6.5 on a Quad Core Xeon Linux Server. An energy grid for FABP5 (PDB: 1B56, 2.05 Å) was generated using the grid program. Then, each molecule was flexibly docked to the FABP5 grid (DOCK FLX protocol) and the single lowest-energy pose was retained.

Example 1. In-Silico Lead Identification

The virtual screening (Irwin, J. J. et al. 2005) was conducted to elucidate new potential lead structures that could inhibit the transport of anandamide by FABP5 and FABP7. Utilizing a newly developed footprint similarity scoring (FPS) algorithm in DOCK 6.5 (Balius, T. E. et al. 2011), a library of ligands was enriched based on their ability to match key interactions seen between the natural substrate oleic acid and FABP7. Recently, similar methodology has been employed for the discovery of HIVgp41 inhibitors (Holden, P. M. et al. 2012).

Figure 2:
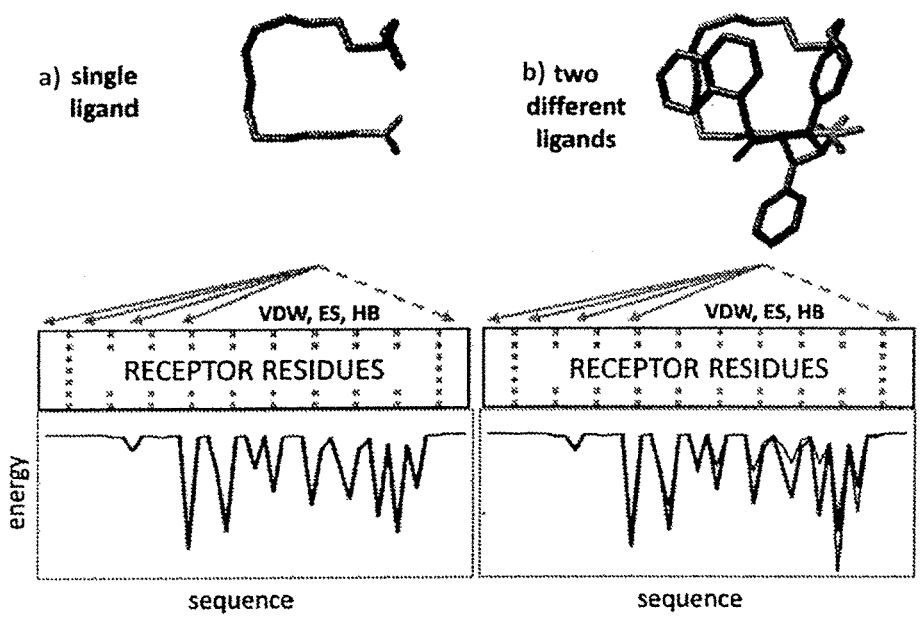
FIG. 2. Illustration of Footprint Similarity Score (a) reference ligand (b) comparing docked molecule with reference.

High-throughput virtual screening in drug discovery has increasingly become a powerful and practical approach for pre-screening ligand libraries for biologically relevant molecules (Kuntz, I. D. 1992; Jorgensen, W. L. 2004; Shoichet, B. K. 2004). Traditionally, docking programs attempt to approximate the intermolecular binding energy between a ligand and a receptor. To save computational time, often grid-based approaches provide the best compromise between accuracy and sampling time (Meng, E. C. et al. 1992). Despite having moderate success rates, traditional docking typically favors larger molecules due to direct correlation between increasing van deer Walls energy and the number of atoms in a molecule (Balius, T. E. et al. 2011; Kuntz, I. D. et al. 1999). Often, small consideration of specific binding orientation is accounted for; mostly translated through favorable electrostatic interactions. Molecular footprints consist of two-dimensional representations of the ligand-receptor as a per-residue decomposition of the standard DOCK energy score (FIG. 2). Thus, we carried out our virtual screening based on the hypothesis that molecular footprint matching between a docked library and a reference molecule would translate into a greater DOCK success rate, specifically the unique ability to enrich for active compounds (positives) that are energetically similar to a reference (Balius, T. E. et al. 2011).

Figure 3:
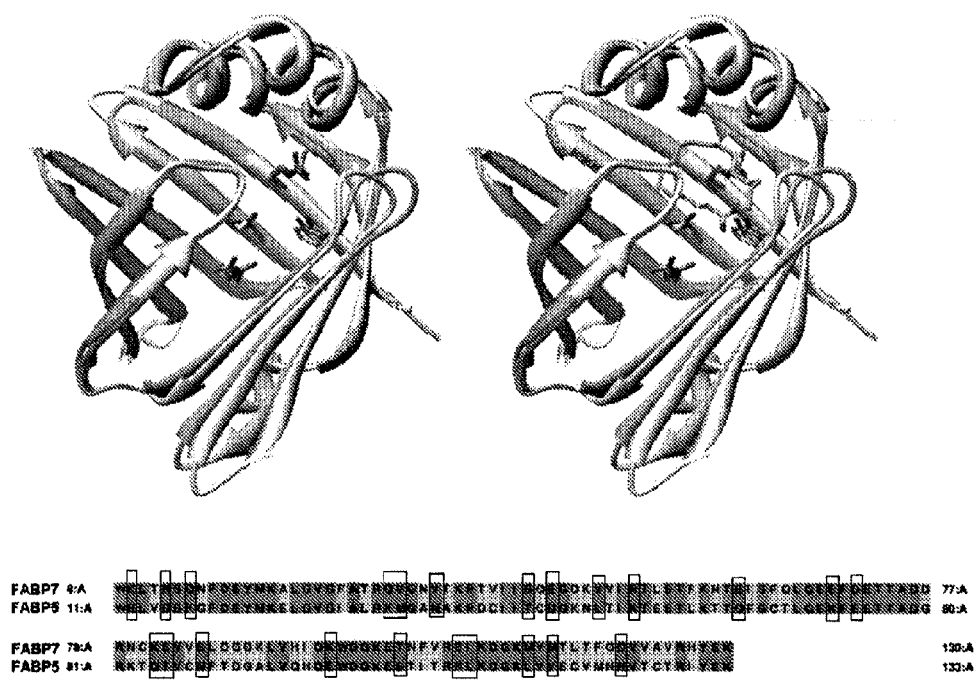
FIG. 3. Sequence alignment of FABP7 (light grey) and FABP5 (dark gray). Binding motif ARG106, ARG126, TYR128 is identical between FABP7 and FABP5 (dark gray). MET115 in FABP7 is similar but not identical to VAL115 in FABP5 (boxed). Oleic acid is encapsulated by the FABP.

The CB-1 receptor is predominately expressed in the brain and thus both FABP5 and FABP7 were considered relevant targets for our virtual screening. FABP5 or epidermal fatty acid binding protein (E-FABP) is typical dispersed throughout the body (tongue, adipose tissue, dendritic cell, mammary gland, brain neurons, kidney, liver, lung and testis) and found abundantly in the epidermal cells of the skin. FABP7 or brain fatty acid binding protein (B-FABP) is typically expressed in high levels during mid-term embryonic development but not present in neurons. Structural alignment (0.93 RMSD) of FABP7 (PDB: 1FE3, 2.8 Å) and FABP5 (PDB: 1B56, 2.05 Å) revealed a 47% sequence identity and 66% similarity (FIG. 3). Furthermore, both FABP7 and FABP5 bind fatty acid substrates with high affinity; although FABP7 typically shows higher binding affinity in-vitro. Thus, FABP7 was selected as our target for virtual screening. Additional docking analysis has shown that DOCK scores obtained from our FABP7 screening hits (48 compounds), tended to be more favorable when re-docked into FABP5.

Footprint-Based Rescoring

Figure 4:
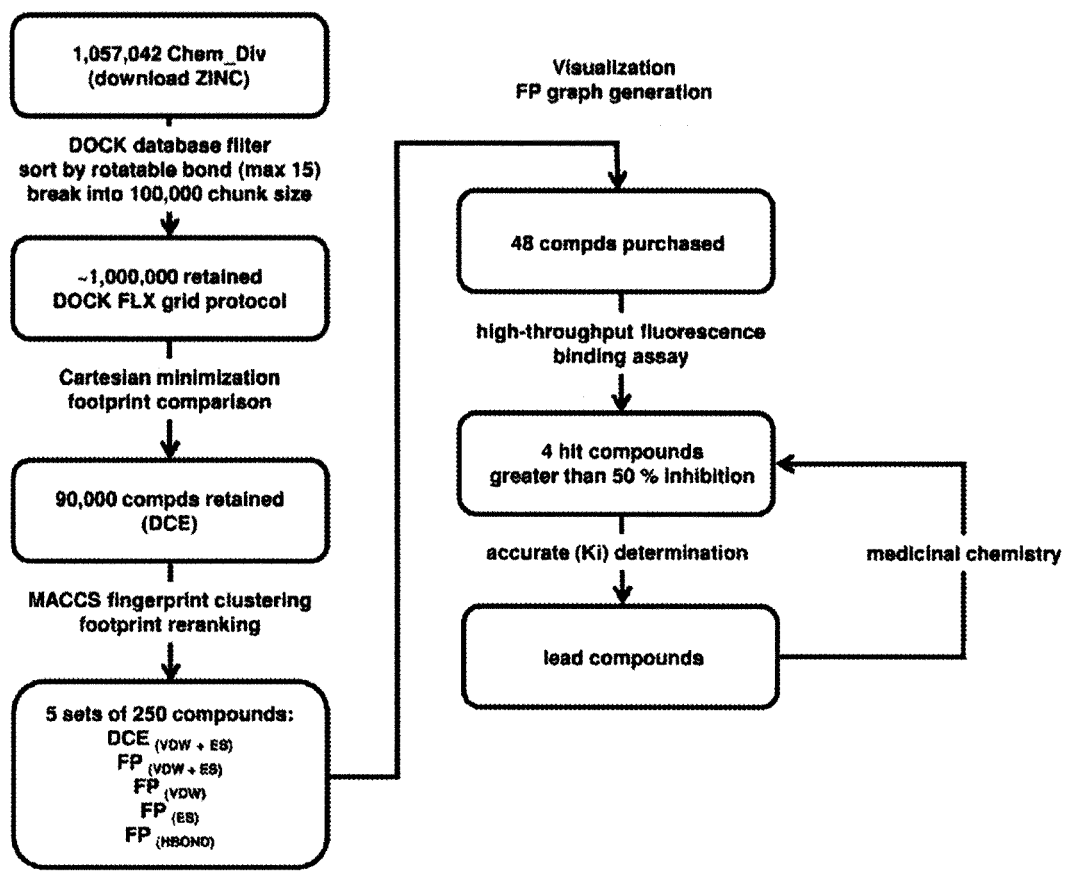
FIG. 4. A flow chart describing the discovery of ligands through virtual screening, biological assay, and medicinal chemistry.

High-throughput virtual screening utilizing the footprint rescoring method was conducted on FABP7 using oleic acid as the reference molecule. This entailed: 1) grid setup and docking 2) minimization of each docked molecule and reference molecule on the receptor Cartesian coordinates, 3) calculating the molecular footprints of all docked molecules and reference, 4) calculation of a footprint similarity score (FPS) for each of the docked molecules versus the reference oleic acid, 5) MACCS fingerprint clustering, 6) rank-ordering based on each scoring criteria, 7) analysis and selection of compounds from each of the 250 cluster heads generated for each of the scoring criteria (FIG. 4) using visual inspection of binding poses and footprints.

First, subsets 1 through 5 and subset 6 through 10 containing ~500,000 molecules were rank-ordered by the DOCK Cartesian energy (DCE) score. The top 45,000 of each combined subset of 500,000 molecules (~10% total 90,000 molecules) were then clustered using MACCS fingerprints, as implemented in the program MOE with the tanimoto coefficient of 0.75. The resulting cluster heads obtained were then further rank-ordered by: (i) standard DOCK score ($DCE_{VDW+ES}$), (ii) van der Waals footprint similarity score ($FPS_{VDW}$), (iii) electrostatic footprint similarity score ($FPS_{ES}$), (iv) H-bond footprint similarity score ($FPS_{HBOND}$), (V) the sum or van der Waals and electrostatic footprint similarity score ($FPS_{VDW+ES}$).

Figures 5D, 5E:
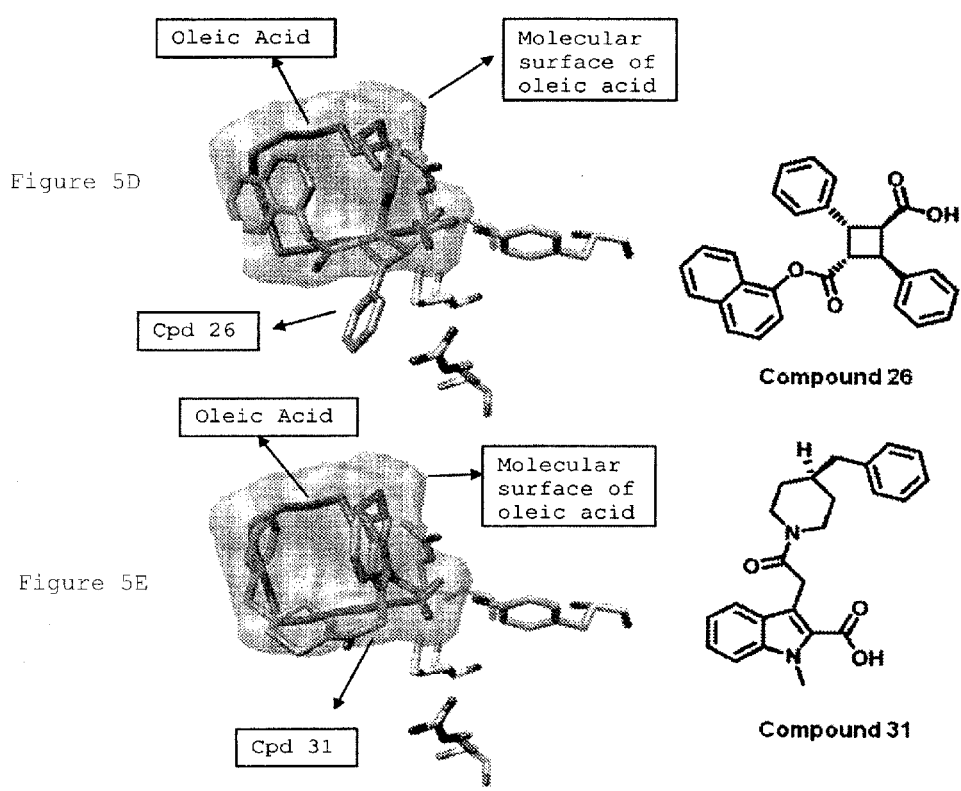
Figure 6:
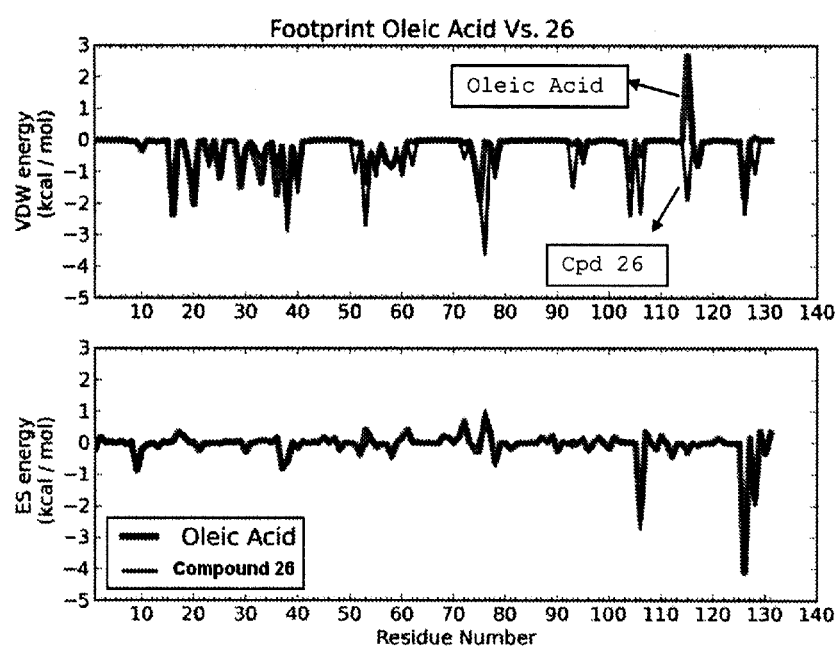
FIG. 6. The VDW and ES footprint overlay of oleic acid and Compound 26. A significant VDW clash between the reference oleic acid and MET115 can be seen in the VDW footprint. This steric clash is seen to be offset by the strong ES interactions at ARG 106, ARG126, and TYR 128 seen in the ES footprint. Energetically DOCK selected ligands from the ChemDiv library that did not have unfavorable interaction, both VDW and ES, intrinsically selecting inhibitors with a good ES footprint match while mitigating the VDW clash at MET115.

As a result of the virtual screening, 48 compounds were selected and assayed in-vitro against FABP5. Of the 48 compounds tested, 23 showed at least 25% inhibition and 4 compounds, 19, 26, 27 and 31 (ChemDiv library ID#: 5511-0235, 8009-2334, 8009-7646, and C075-0064), showed approximately 50% inhibition or greater (FIG. 5). As seen in Table 1, Compound 26 had the highest correlation among all the leads to the electrostatic footprint of oleic acid with favorable interaction at ARG106, ARG126, TYR128 (FIG. 6). Furthermore, Compound 26 also had good VDW overlap contributing to its low footprint score ($FPS_{VDW+ES}$=−56.76, −68.27) despite a significant clash seen in the crystal structure for oleic acid at MET 115. Critical to the binding of Compound 26, one free carboxylate similar to that observed in oleic acid was essential, specifically for the binding to ARG106, ARG126, TYR128 sequence.

TABLE 1

Dock energy scores for FABP7 and FABP5 and experimental values for FABP5

| ID | Method | $DCE_{FABP7}$ | $FP_{VDW+ES}$ | $FP_{VDW}$ | $FP_{ES}$ | $DCE_{FABP5}$ | % I CDiv ID | $K_i$ (μM) |
|---|---|---|---|---|---|---|---|---|
| 19 | $FPS_{VDW+ES}$ | −56.56 | 1.09 | 0.81 | 0.28 | −64.38 | 67.5 5511-0235 | ND |
| 26 | $FPS_{VDW+ES}$ | −56.76 | 1.01 | 0.87 | 0.14 | −68.27 | 78.12 N/A | 1.19 |
| 27 | $FPS_{ES}$ | −53.34 | 1.21 | 1.00 | 0.21 | −65.91 | 49.57 8009-7646 | ND |
| 31 | $FPS_{VDW+ES}$ | −53.77 | 1.12 | 0.73 | 0.39 | −71.20 | 49.93 C075-0064 | ND |
| Avg. | | −55.11 | 1.11 | 0.85 | 0.26 | −67.44 | 61.28 | — |

Example 2. Synthesis of α-Truxillic Acid Monoesters

As shown below (Scheme 1), starting from E-(trans)-cinnamic acid irradiation in the solid state promotes the [2+2] cycloaddition to afford the head to tail dimer α-truxillic acid in good yields and excellent purity. Further modification of the α-truxillic acid to yield α-2,4-diphenyl-cyclobutane-1,3-dicarboxylic acid mono esters proceeds through the di-acyl chloride intermediate followed by addition of an alcohol or amine substituent to form the ester and amide products respectively. Mono and di substitution products are seen for substitution with 1-naphthol at a ratio of 2.5 in favor of the mono substitution. Workup with 1N HCl converts the remaining acyl chloride to the corresponding free carboxylic acid.

Scheme 1.

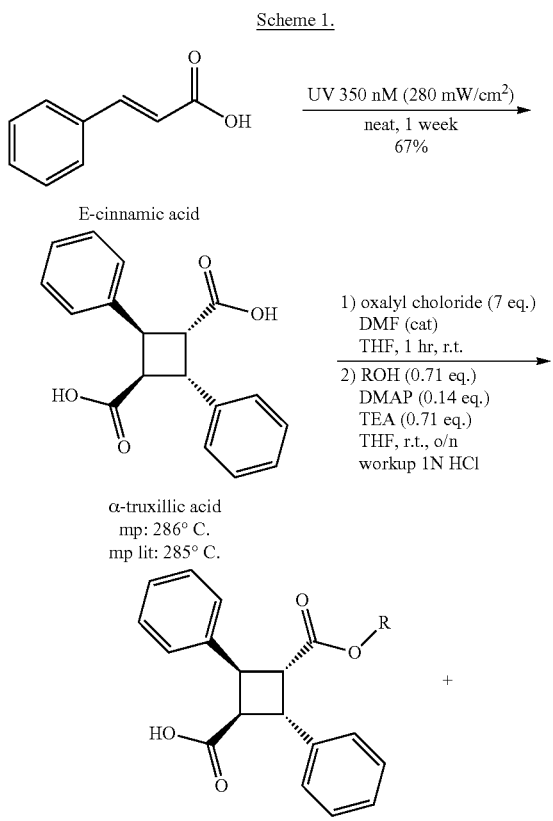

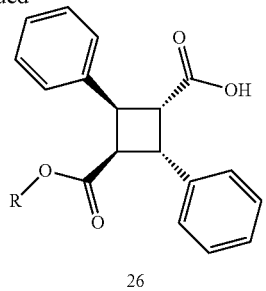

26

R = 1-napthol, 46% in two steps
mp: 195° C.

α-2,4-diphenyl-cyclobutane-1,3-dicarboxylic Acid (α-truxillic Acid)

E-cinnamic acid, 1.272 g (8.59 mmol) was placed into a pyrex dish and exposed to light at 350 nM and an intensity of 280 mW/cm² for 1 week with periodic shaking. This process was performed in the solid state and could be monitored by $^1$H NMR. After completion the white solid was washed with diethylether (200 mL) and allowed to dry. The solid was then recrystallized from pure ethanol to give alpha-truxillic acid 1.006 g (3.39 mmol), 79% yield as a white solid. mp 276-277° C. (lit. 274-278° C.) $^1$H NMR (300 MHz, DMSO-$d_6$): δ 12.12 (s, 2H), 7.32 (m, 8H), 7.24 (m, 2H), 4.28 (dd, J=7.2 Hz, 10.1 Hz, 2H) 3.81 (dd, J=7.2 Hz, 10.1 Hz, 2H). $^{13}$C NMR (75 MHz, DMSO-$d_6$): δ 173.00, 139.47, =7.2 Hz, 10.1 Hz, 2H). $^{13}$C NMR (75 MHz, DMSO-$d_6$): δ 173.00, 139.47, 128.19, 127.67, 126.69, 46.17, 41.06. Data is consistent with literature values (Yang, J. L. et al. 2007)

α-2,4-diphenyl-cyclobutane-1,3-dicarboxylic Acid mono-(1-naphthol) Ester (Compound 26)

To 500 mg (1.69 mmol) of pure alpha-truxillic acid, 20 mL of tetrahydrofuran was added along with 1.01 mL (11.81 mmol) of oxalyl chloride. While stirring 1 drop of DMF was added and the solution was allowed to stir at room temperature for 1 hour. After completion, the reaction was concentrated in-vacuo to remove all volatiles. To the crude yellow solid made previously, 20 mL of tetrahydrofuran was added followed by the addition of 0.19 mL (1.34 mmol) of triethylamine and 84 mg (0.69 mmol) of DMAP. While stirring 173 mg (1.20 mmol) of 1-naphthol previously dissolved in 10 mL of tetrahydrofuran was added dropwise. The reaction was allowed to stir overnight at room temperature and quenched with 1 N HCl upon completion. The reaction mixture was then extracted using 100 mL of dichloromethane and washed with 100 mL of brine. The resulting organic layer was dried with MgSO$_4$ and concentrated in-vacuo to give a brownish oil which was then subsequently purified using flash chromatography with 20% ethyl acetate in hexanes followed by 30% ethyl acetate hexanes to give the α-2,4-diphenyl-cyclobutane-1,3-dicarboxylic acid mono-(1-naphthol) ester 210 mg (0.50 mmol), 42% yield as a white solid. mp 195° C. $^1$H NMR (500 MHz, DMSO-d$_6$): δ 12.24 (s, 1H), 7.88 (d, J=8.5 Hz, 1H), 7.73 (d, J=8.5 Hz, 1H), 7.57 (d, J=7.0 Hz, 2H), 7.52 (d, J=7.5 Hz, 2H), 7.48-7.37 (m, 6H), 7.34-7.27 (m, 3H), 7.06 (d, J=8.0 Hz, 1H), 6.38 (d, J=7.5 Hz, 1H) 4.61-4.49 (m, 3H), 3.98 (dd, J=7.0 Hz J=10.0 Hz, 1H). $^{13}$C NMR (75 MHz, DMSO-d$_6$): δ 172.73, 170.93, 146.17, 139.23, 139.03, 133.92, 128.74, 128.25, 128.19, 127.89, 127.67, 127.40, 126.90, 126.47, 126.22, 125.85, 125.45, 121.13, 117.86, 46.17, 41.54, 41.11. HRMS (ESI) m/e calculated for C$_{28}$H$_{23}$O$_4$H+:423.1589. Found: 423.1596 (Δ=1.7 ppm).

Example 3. Synthesis of γ-Truxillic Acid Monoesters

As shown below (Scheme 2), starting from α-truxillic acid isomerization at high temperature and formation of the anhydride by addition of acetic anhydride provides the glutaric anhydride γ-truxillic acid precursor. This anhydride intermediate can then afford any γ-2,4-diphenyl-cyclobutane-1,3-dicarboxylic acid mono esters or mono amides by activation with DMAP at room temperature and addition of an alkyl or aromatic alcohol or amine.

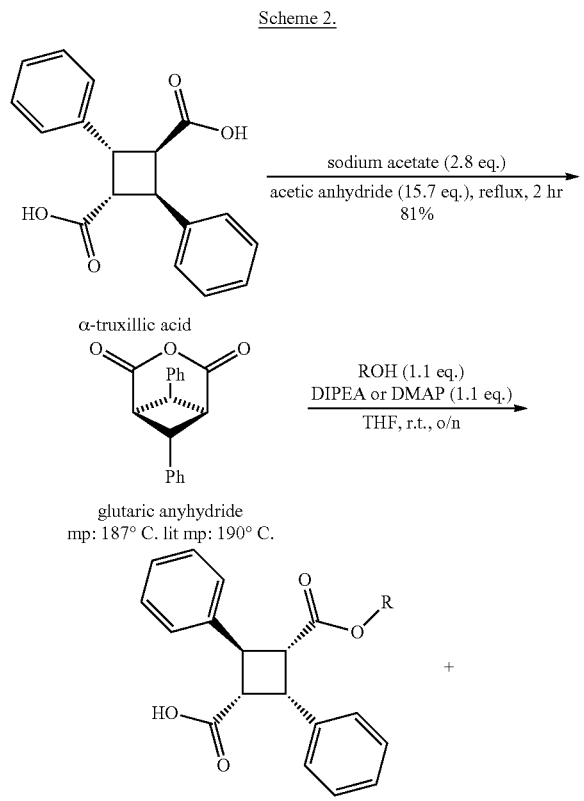

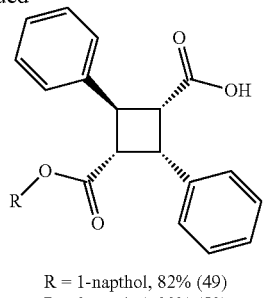

R = 1-napthol, 82% (49)
R = 2-napthol, 92% (50)

3-Oxabicyclo[3.1.1]heptane-2,4-dione, 6,7-diphenyl (γ-Truxillic Anhydride)

To 600 mg (2.02 mmol) of pure α-truxillic acid, 775 mg of anhydrous sodium acetate and 5 mL of acetic anhydride was added to a 20 mL round bottom flask. The solution was refluxed at 150° C. for 24 hours. After completion the solution was allowed to cool to room temperature. The white solid was washed and filtered with 100 mL of water. The resulting solid was dried and then first dissolved in chloroform (10 mL) and then upon addition of 100 mL of ethanol white crystals formed. The white crystals were dried and yielded 398 mg (1.43 mmol), 71% of the desired compound. mp 187° C. (lit. 190° C.) $^1$H NMR (300 MHz, CDCl$_3$): δ 7.51-7.39 (m, 4H), 7.37-26 (m, 4H), 7.09-7.06 (m, 2H), 4.34 (t, J=5.7 Hz, 1H) 4.07 (d, J=5.1 Hz, 2H), 3.99 (s, 1H).

γ-2,4-diphenyl-cyclobutane-1,3-dicarboxylic acid mono-(1-napthyl) Ester (Compound 49)

To 50 mg (0.18 mmol) of pure 3-Oxabicyclo[3.1.1]heptane-2,4-dione, 6,7-diphenyl, 1 mL of tetrahydrofuran was added along with 29 mg (0.20 mmol) of 1-naphthol. While stirring 0.03 mL (0.20 mmol) of diisopropylethylamine was added and the solution was allowed to stir at room temperature for 15 hours. After completion, the reaction was concentrated in-vacuo to remove all volatiles. The reaction mixture was then extracted using 100 mL of dichloromethane and washed with 100 mL of brine. The resulting organic layer was dried with MgSO$_4$ and concentrated in-vacuo to give a brownish solid which was then subsequently purified using flash chromatography with 20% ethyl acetate in hexanes followed by 30% ethyl acetate hexanes to give the γ-2,4-diphenyl-cyclobutane-1,3-dicarboxylic acid mono-(1-naphthol) ester 61 mg (0.14 mmol), 80% yield as a white solid. $^1$H NMR (500 MHz, DMSO-d$_6$): δ 12.27 (b, 1H), 7.87 (d, J=8.5 Hz, 1H), 7.73 (d, J=8.0 Hz, 1H), 7.48-7.24 (m, 13H), 6.88 (d, J=8.0 Hz, 1H), 6.46 (d, J=7.5 Hz, 1H), 4.59 (t, J=10.5 Hz, 1H), 4.47 (t, J=10.0 Hz, 1H), 4.37 (t, J=10.5 Hz, 1H), 3.85 (t, J=10.5 Hz, 1H).

γ-2,4-diphenyl-cyclobutane-1,3-dicarboxylic Acid mono-(2-napthyl) Ester (Compound 50)

To 50 mg (0.18 mmol) of pure 3-Oxabicyclo[3.1.1]heptane-2,4-dione, 6,7-diphenyl, 1 mL of tetrahydrofuran was added along with 29 mg (0.20 mmol) of 2-naphthol. While stirring 0.03 mL (0.20 mmol) of diisopropylethylamine was added and the solution was allowed to stir at room temperature for 15 hours. After completion, the reaction was concentrated in-vacuo to remove all volatiles. The reaction mixture was then extracted using 100 mL of dichloromethane and washed with 100 mL of brine. The resulting organic layer was dried with MgSO$_4$ and concentrated in-vacuo to give a brownish solid which was then subsequently purified using flash chromatography with 20% ethyl acetate in hexanes followed by 30% ethyl acetate hexanes to give the γ-2,4-diphenyl-cyclobutane-1,3-dicarboxylic acid mono-(2-napthyl) ester 70 mg (0.17 mmol), 92% yield as a white solid. $^1$H NMR (300 MHz, DMSO-d$_6$): δ 7.85 (d, J=7.2 Hz, 1H), 7.76 (d, J=9.0 Hz, 1H), 7.66 (d, J=7.2 Hz, 1H), 7.51-7.24 (m, 12H), 6.77 (s, 1H), 6.43 (d, J=8.7 Hz, 1H), 4.55 (t, J=10.8 Hz, 1H), 4.40 (t, J=10.0 Hz, 1H), 4.16 (t, J=10.5 Hz, 1H), 3.84 (t, J=10.2 Hz, 1H).

Example 4. Compound 26 Bound to FABP7

Figure 7:
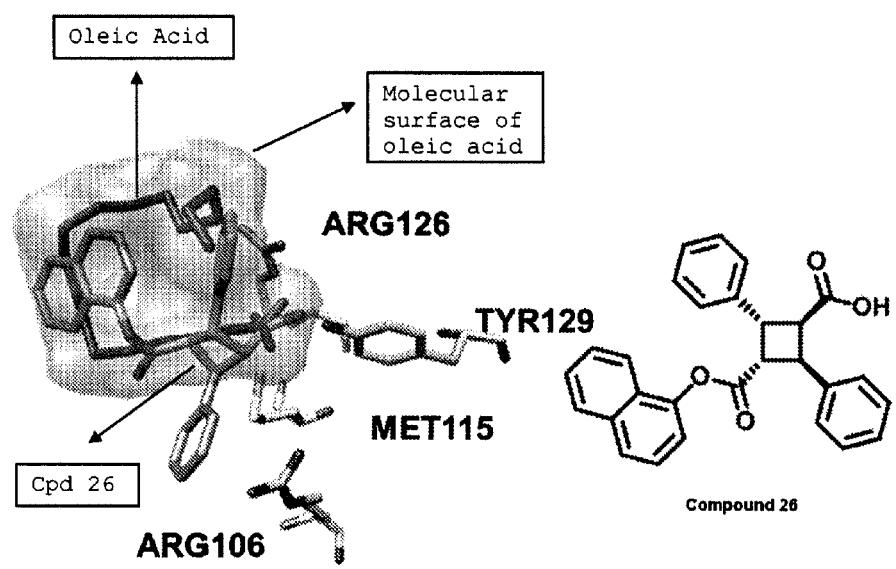
FIG. 7. Compound 26 docked to FABP7 with key interactions seen with amino acid residues ARG126, TYR129, and ARG106. MET115 provides some selectivity by showing VDW clashing with the substrate Oleic Acid which is a known FABP7 substrate.

The free carboxylate of Compound 1 binds primarily to TYR129 and ARG126 similarly to fatty acid substrates (FIG. 7). Furthermore, ARG106 has some interaction as seen in the electrostatic (ES) foot print. However, the long distance between the carboxylate and ARG106 lowers this interaction and suggests possible water mediated hydrogen bonding. Lastly, MET115 provides steric hindrance with the natural substrate oleic acid (Ki 0.35 μM±0.04 FABP7) and provides selectivity for the truxillic acid core.

Example 5. Determination of K$_i$

Figure 8A:
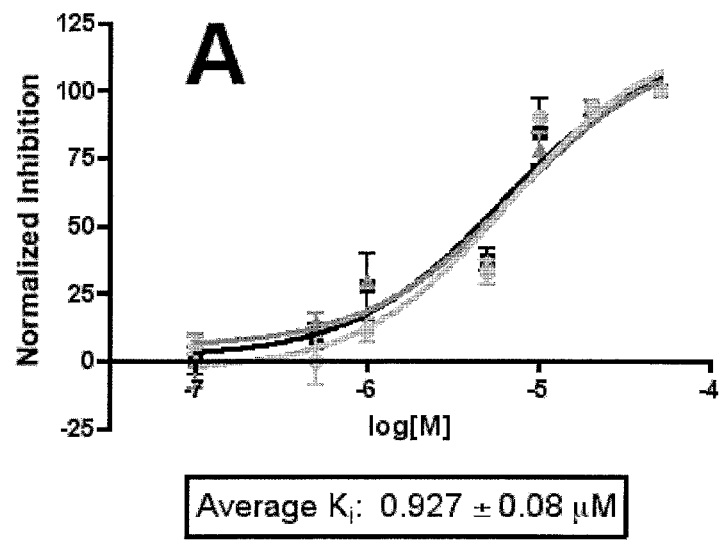
FIGS. 8A-8C. Binding analysis of Compound 26 (α-truxillic acid 1-naphthyl ester), Compound 49 (γ-truxillic acid 1-naphthyl ester), and BMS309403.
Figure 8B:
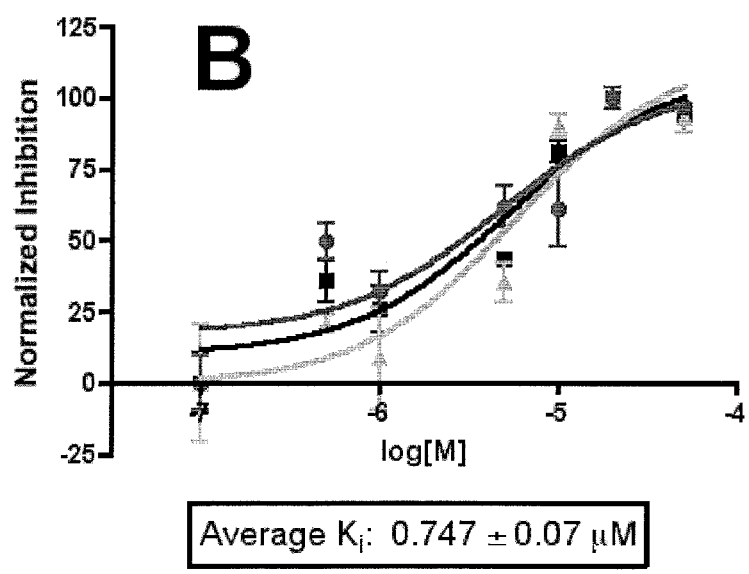
Figure 8C:
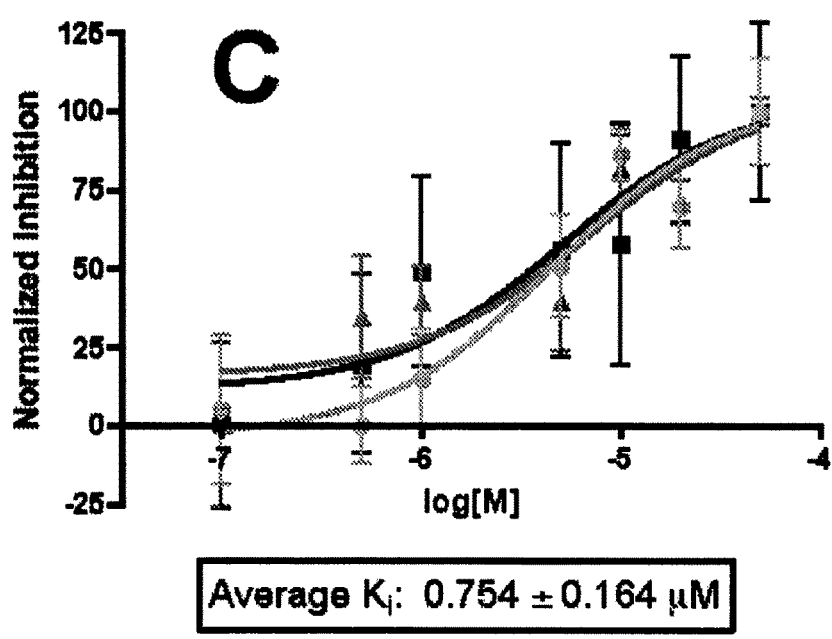

Determination of Ki was derived from calculation using the K$_d$ of stearic acid (Scheme 1). BMS309403 which has been assayed previously utilizing this assay was determined to have a K$_i$ of 0.89 μM±0.31 against FABP5. In comparison, both the α-2,4-diphenyl-cyclobutane-1,3-dicarboxylic acid mono-(1-naphthol) ester (Compound 26) and γ-2,4-diphenyl-cyclobutane-1,3-dicarboxylic acid mono-(1-naphthol) ester (Compound 49), each isolated as a mixture of enantiomers, were tested in triplicate and yielded inhibitory dose dependent K$_i$ values of 0.93 μM±0.07 and 0.75 μM±0.07 against FABP5, respectively (FIGS. 8A and 8B). Thus the γ-2,4-diphenyl-cyclobutane-1,3-dicarboxylic acid mono-(1-naphthol) ester was the better inhibitor. The inhibitory dose dependent K$_i$ values of BMS309403 was 0.75 μM±0.164 against FABP5 (FIG. 8C).

Scheme 3.

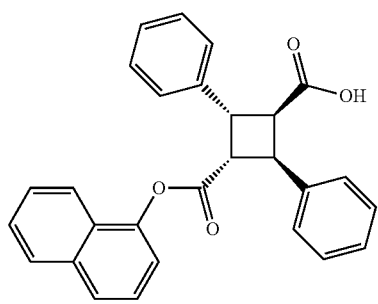

Compound 26

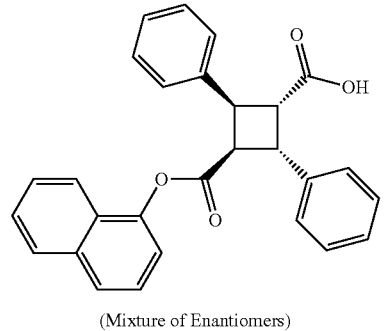

(Mixture of Enantiomers)
K$_i$ = 0.93 ± 0.07 μM

Compound 49

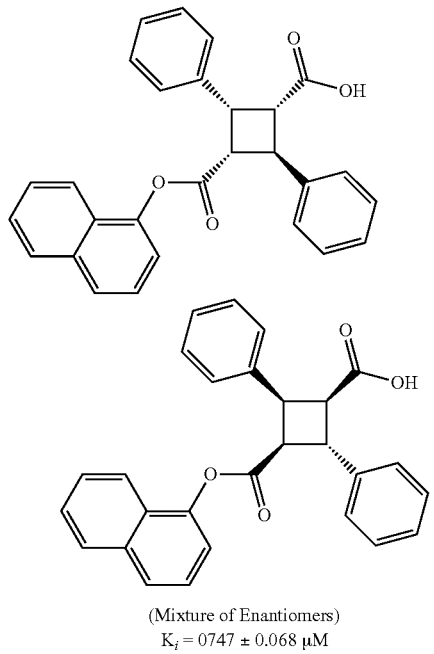

(Mixture of Enantiomers)
K$_i$ = 0747 ± 0.068 μM

Example 6. Effects of Compound 26 on Glutamate-Mediated Synaptic Transmission

Activation of cannabinoid CB1 receptors inhibits glutamatergic synaptic transmission in numerous brain areas, including the dorsal root ganglion DR (Haj-Dahmane, S et al. 2009). Therefore, to test whether Compound 26 exhibits agonist properties at CB1 receptors, we examined its effects on the amplitude of glutamate-mediated excitatory postsynaptic currents (EPSCs) recorded from DR 5-HT neurons. We found that bath application of Compound 26 (10 μM) did not inhibit the amplitude of EPSCs (107±6.7% of baseline, n=8 (FIG. 8A-B). Such a finding suggests that Compound 26 is not a CB1 receptor agonist.

Example 7. Effect of Compound 26 Upon AEA Uptake in Cells

Figure 9A:
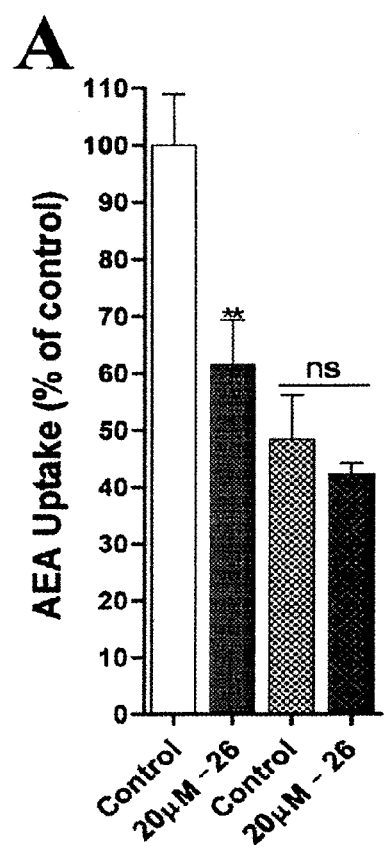
FIGS. 9A-9B. Compound 26 inhibits the cellular uptake of AEA.
Figure 9B:
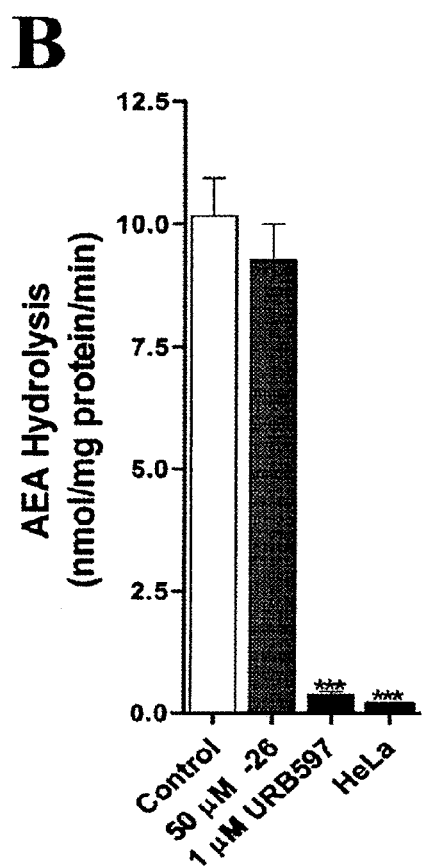

We have previously shown that FABPs are intracellular carriers that shuttle endocannabinoids and related N-acylethanolamines to intracellular sites, such as FAAH for hydrolysis (Kaczocha, M. et al. 2209; Kaczocha, M. et al. 2012). Pharmacological or genetic inhibition of FABPs reduces AEA catabolism in cells, confirming an essential role for these proteins in endocannabinoid inactivation. Therefore, we examined whether the novel FABP inhibitor Compound 26 reduces FABP-mediated AEA uptake in cells. Indeed, Compound 26 significantly inhibited cellular AEA accumulation. Confirming its selectivity for FABPs, Compound 26 failed to reduce AEA uptake in cells bearing a knockdown of FABP5 (FIG. 9A), the main FABP expressed in HeLa cells. Additionally, Compound 26 does not inhibit FAAH (FIG. 9B). Collectively, these results indicate that Compound 26 is a selective FABP inhibitor.

Figure 10A:
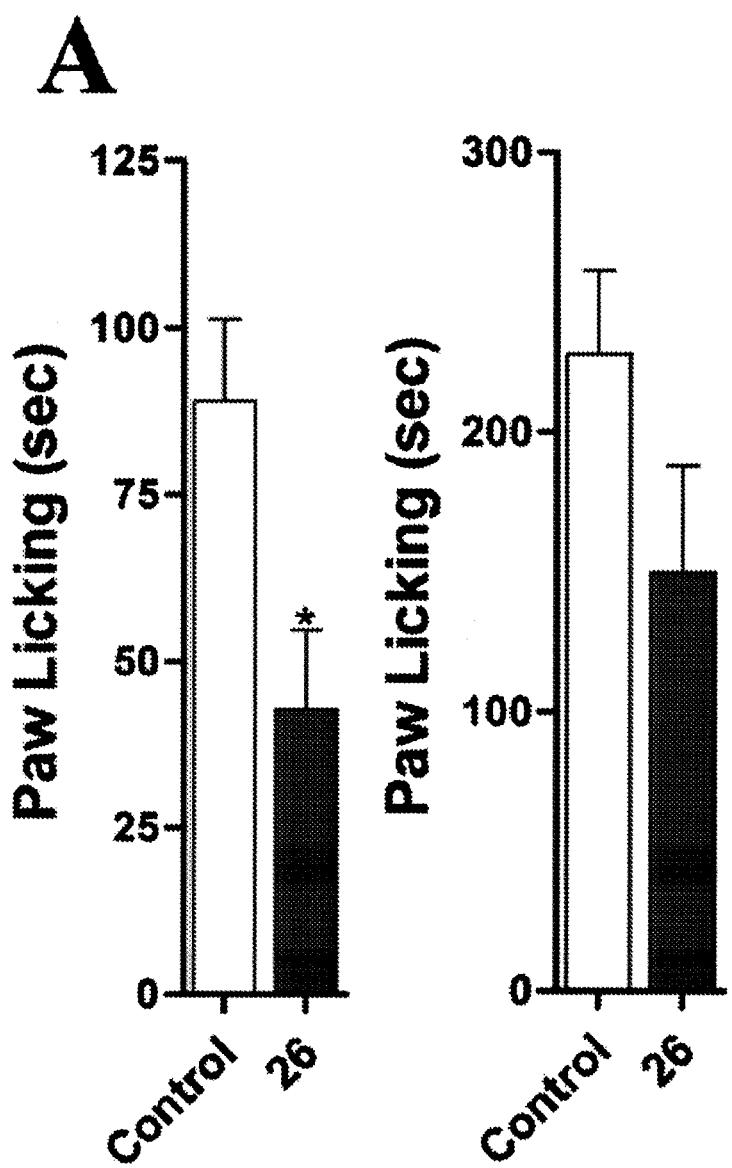

Example 8. Compound 26 Produces Antinociceptive and Anti-Inflammatory Effects in Mice Similar to cannabinoid receptor agonists, inhibitors of endocannabinoid inactivation produce anti-inflammatory and antinociceptive effects (Cravatt, B. F. et al. 2001; Lichtman, A. H. 1990). Importantly, FAAH inhibitors lack the untoward psychotropic effects of cannabinoid receptor agonists (Cravatt, B. F. et al. 2004), highlighting the therapeutic advantage of pharmacologically targeting endocannabinoid inactivation. Because inhibition of AEA transport to FAAH reduces AEA inactivation, we hypothesized that FABP inhibitors may likewise possess antinociceptive and anti-inflammatory properties. Therefore, we examined the effects of Compound 26 using two nociceptive models: the formalin test and carrageenan-induced thermal hyperalgesia. In the formalin test, injection of formalin results in the induction of two temporally distinct phases of pain with the first phase (0-5 min) representing nociceptor activation and the second phase (15-45 min) representing inflammatory pain and central sensitization. As shown in FIG. 10A, Compound 26 significantly reduced nocifensive behavior only during the first phase of the formalin test.

Figures 11A, 11B:
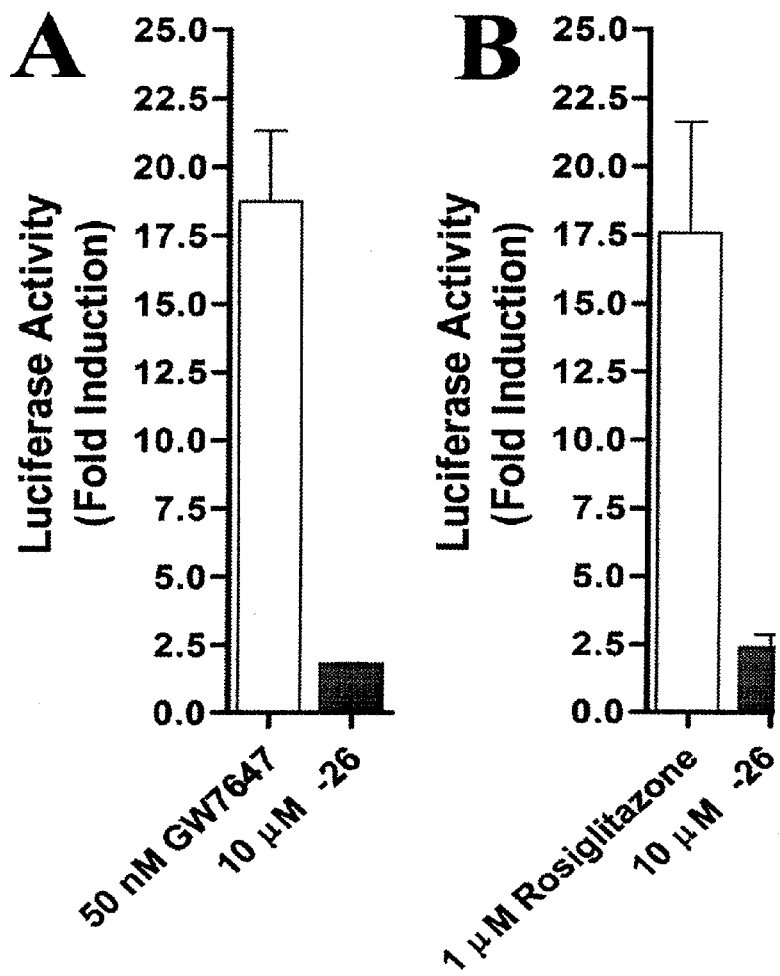
FIGS. 11A-11B. Compound 26 is a weak agonist at PPARα and PPARγ receptors.

We next explored whether Compound 26 alleviates inflammatory pain induced by intraplantar injection of A-carrageenan. Indeed, Compound 26 (20 mg/kg, i.p.) significantly reduced carrageenan-induced thermal hyperalgesia (FIG. 10B) and paw edema (FIG. 10C). To establish a cannabinoid receptor-mediated mechanism of action, mice were pretreated with a combination of the cannabinoid receptor 1 and 2 antagonists, rimonabant and SR144528, respectively. The antinociceptive and anti-edematous effects of Compound 26 were completely reversed by rimonabant and SR144528 (FIGS. 10B and 10C). Previous reports indicate that α-truxillic acid derivatives activate peroxisome proliferator-activated receptor γ (PPARγ), which alongside PPARα, modulate nociception (Steri, R. et al. 2010; Loverme, J, et al. 2006; Churi, S. B. et al. 2008). In our hands, Compound 26 served as a weak agonist at both receptors, displaying ~2-fold activation of PPARα and ~3-fold activation of PPARγ (FIG. 11).

Example 10. Additional Derivatives

An additional aspect of the invention provides analogues of Compounds 1, 2, and 3 that are active as FABP inhibitors. The analogs of Compounds 1, 2, and 3 described below in Schemes 4-10 have analogous activity to Compound 26.

The [2+2] cycloaddition of the derivatives of trans-cinammic acid are known to proceed through light induced photocyclization. Thus the corresponding substituted phenyl analogues of α-truxillic acid can be synthesized and alternatively converted to γ-truxillic analogues by isomerization. $R_n$ can include any alkyl, aryl, heteroaryl, hydroxyl, thiol, amine, amide, carbamate, urea, halogen, hydrazide, etc. (Scheme 4).

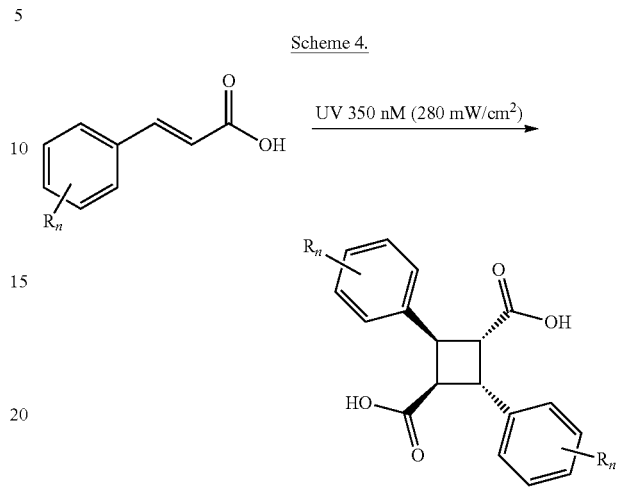

Scheme 4.

Both α and γ truxillic acids are symmetrical molecules and thus are inherently enantiopure by symmetry. Upon functionalization however, desymmetrization creates chirality induced by the equal chance for nucleophllic acyl substitution to occur at either carbonyl. Thus by the use an enantiopure nucleophile, two distereomers can be formed as opposed to two enantiomers facilitating separation of the corresponding distereomers by either flash chromatography or preparative HPLC. (S)-(−)-1-phenylethanol can serve both as a good chiral auxiliary and protection group with selective removal by Pd/C.

For γ-truxillic acids, specifically the glutaric anhydride intermediate, addition of (S)-(−)-1-phenylethanol can be accomplished at room temperature by addition of DMAP (Scheme 5).

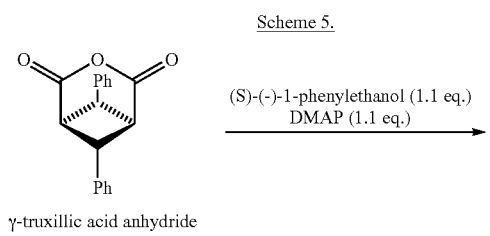

Scheme 5.

γ-truxillic acid anhydride

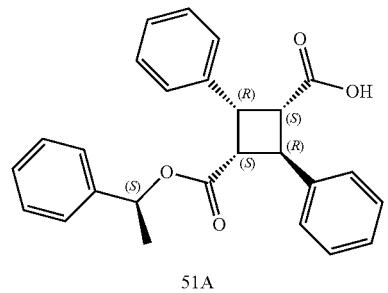

51A

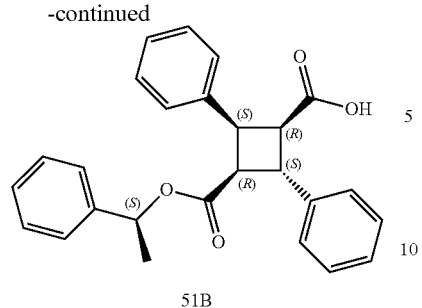

51B

For α-truxillic acids, addition of (S)-(−)-1-phenylethanol to produce the mono-ester is accomplished by first forming the di-acyl chloride intermediate with oxalyl chloride and then subsequent nucleophilic acyl substitution in the presence of TEA (Scheme 6).

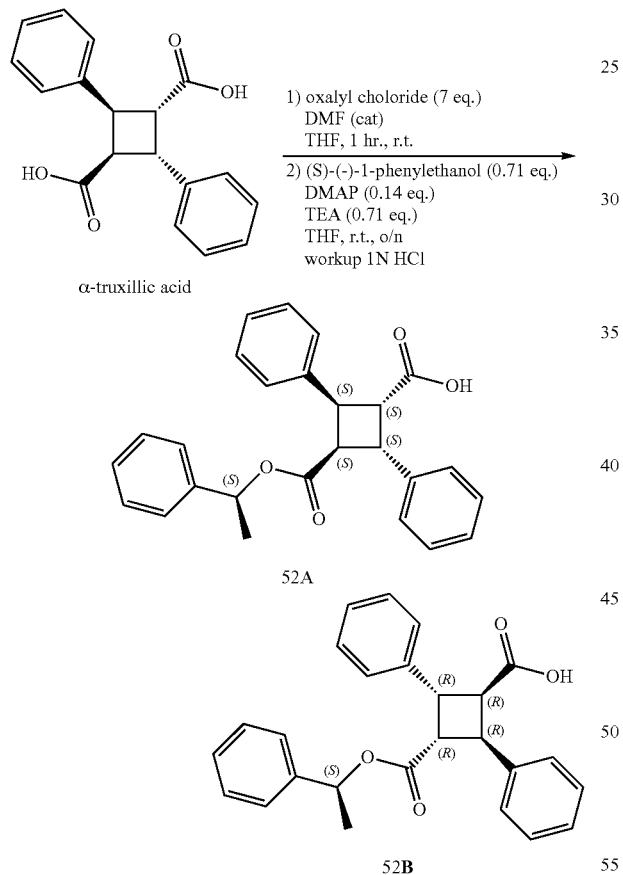

Any of compounds 51A, 51B, 52A or 52B, once separated from their corresponding diastereomer, are used as intermediates en route to a variety of enantiopure analogs that have analogous activity to Compound 26. Compounds 51A, 51B, 52A or 52B may be reacted with oxalyl chloride in the presence of naphthalen-1-ol to form both enantiomers, separable, of Compound 26 or Compound 49.

For example, upon the separation of enantiopure truxillic acid 51A, further modification is performed by first generating the acyl chloride followed by the addition of an amine or alcohol with TEA to afford the hetero di-substituted compound. Selective deprotection of the benzylic group by Pd/C thereby affords enantiopure mono esters or amides (Scheme 7).

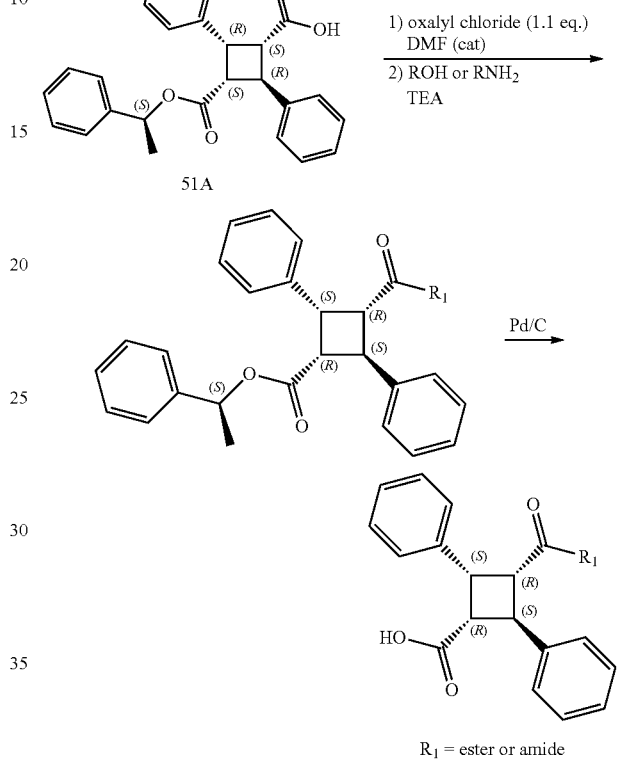

$R_1$ = ester or amide

Further diversification of the truxillic acid leads is investigated by selective reduction of the free carboxylic acid with borane dimethyl sulfide which affords the corresponding primary alcohol of, for example, 51A (Scheme 8). To the alcohol, commercial available acyl chlorides is added in the presence of TEA followed by Pd/C deprotection to afford "reversed ester" analogues. In addition, any aryl alcohol is coupled via the Mitsunobu reaction to form the corresponding ether analogues after deprotection by Pd/C.

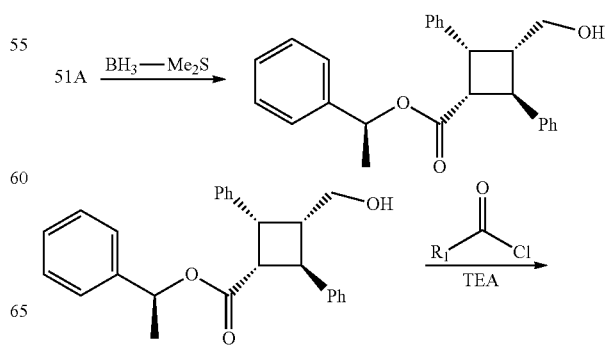

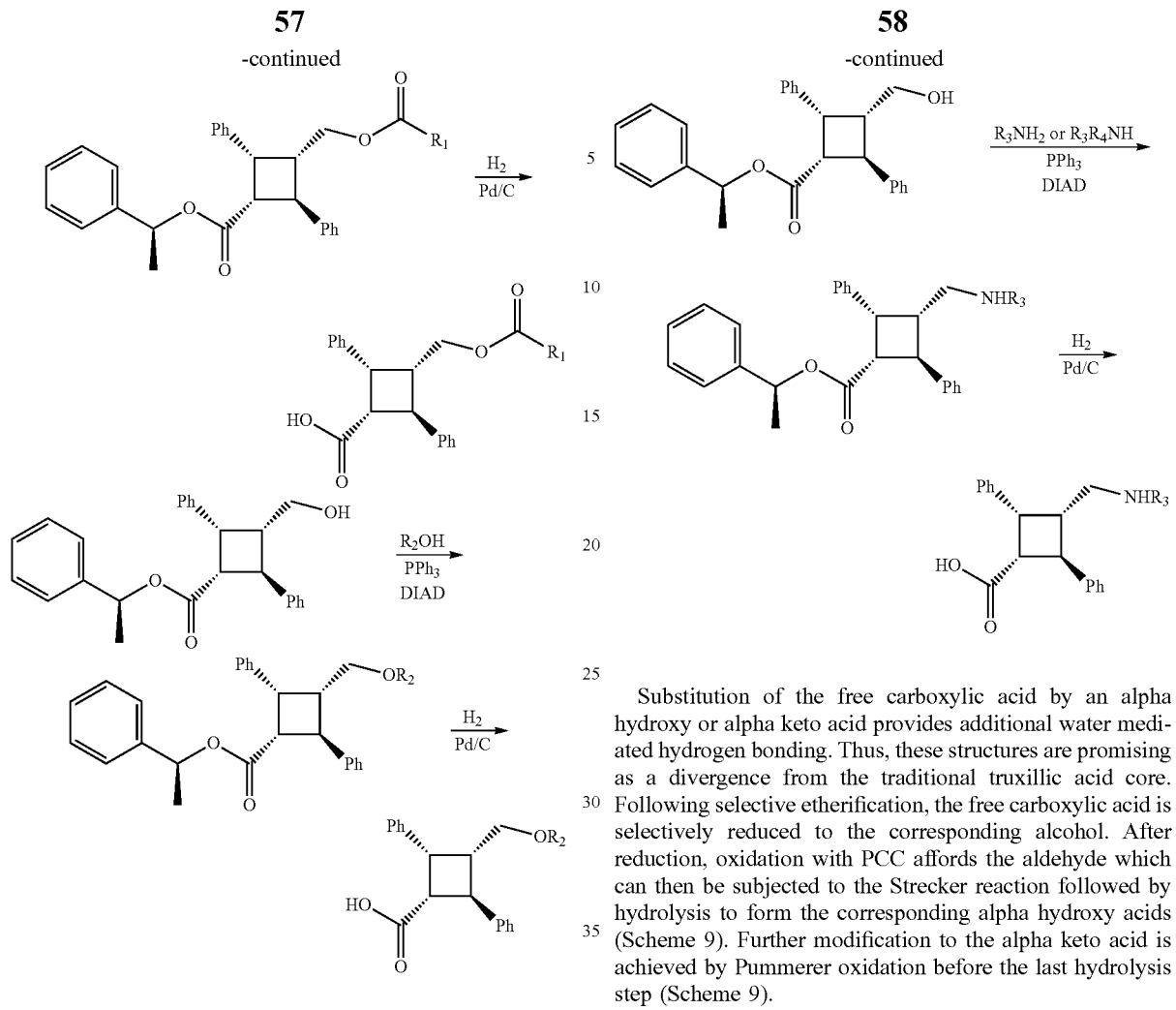

Substitution of the free carboxylic acid by an alpha hydroxy or alpha keto acid provides additional water mediated hydrogen bonding. Thus, these structures are promising as a divergence from the traditional truxillic acid core. Following selective etherification, the free carboxylic acid is selectively reduced to the corresponding alcohol. After reduction, oxidation with PCC affords the aldehyde which can then be subjected to the Strecker reaction followed by hydrolysis to form the corresponding alpha hydroxy acids (Scheme 9). Further modification to the alpha keto acid is achieved by Pummerer oxidation before the last hydrolysis step (Scheme 9).

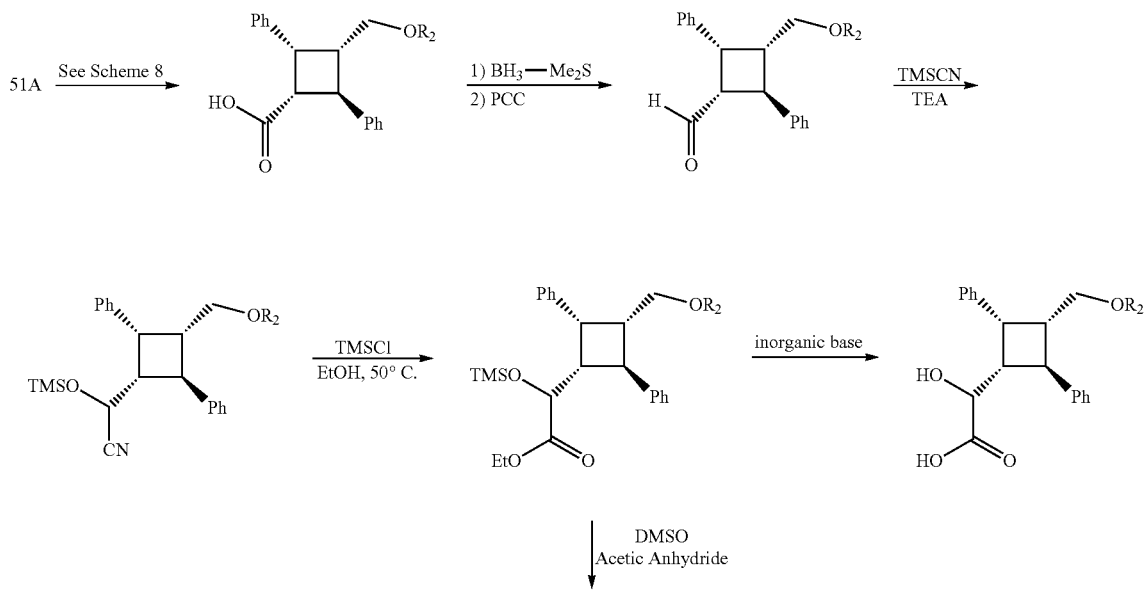

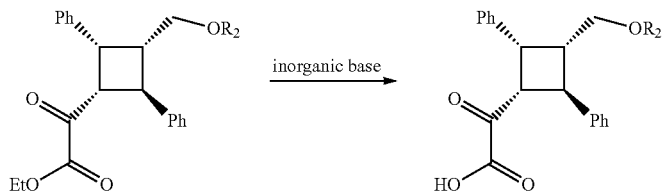
Additional analogs are synthesized according to the protocols in Scheme 10. Enantiopure compound 51 is reduced with borane dimethyl sulfide which affords the corresponding primary alcohol. Treatment with sodium azide results in the alkyl azide, which is reduced to the primary amine. The primary amine is converted to a variety of analogs (Scheme 10).
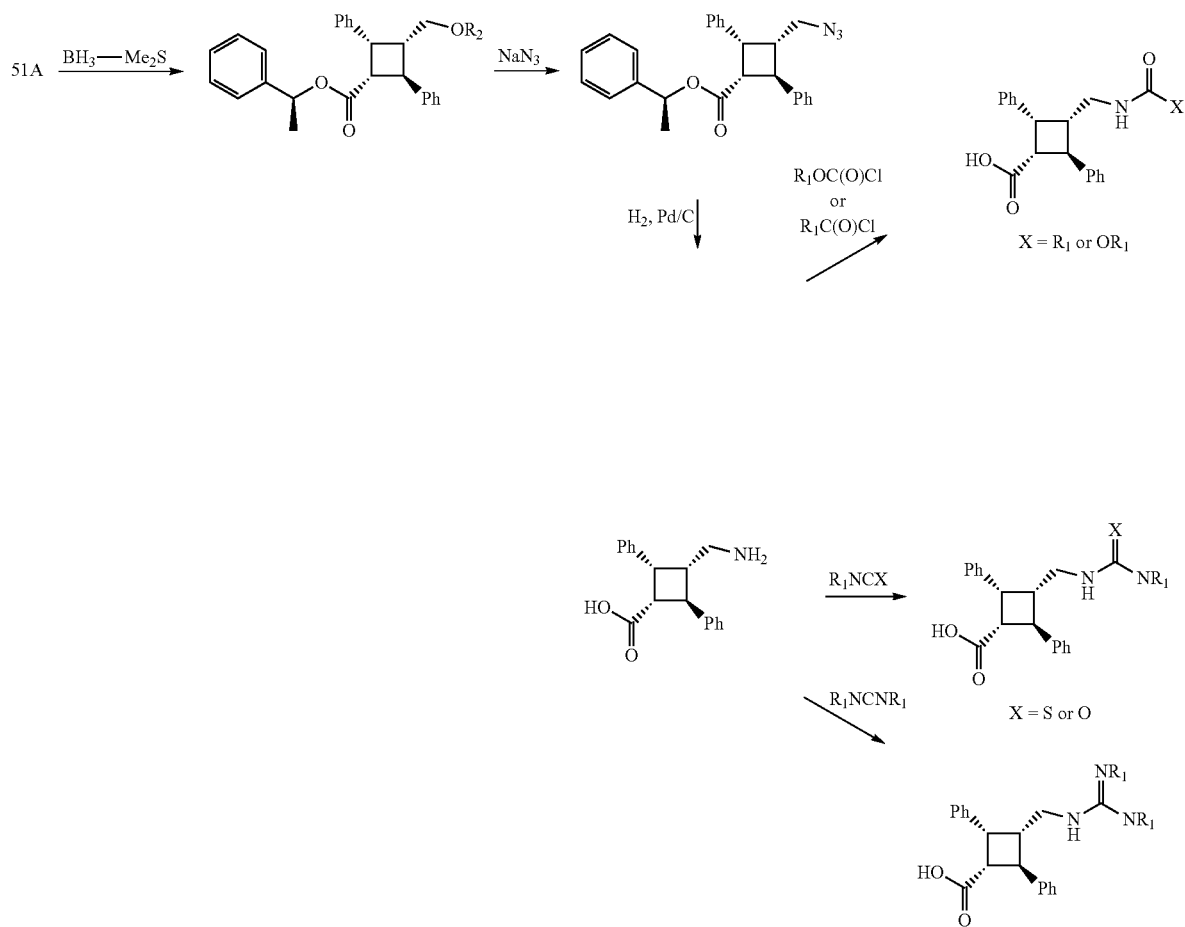

Additional analogs are synthesized according to the protocols in Scheme 11. The enantiopure aldehyde (synthesized by methods shown in Scheme 9) is converted to a variety of analogs (Scheme 11).

Scheme 11.

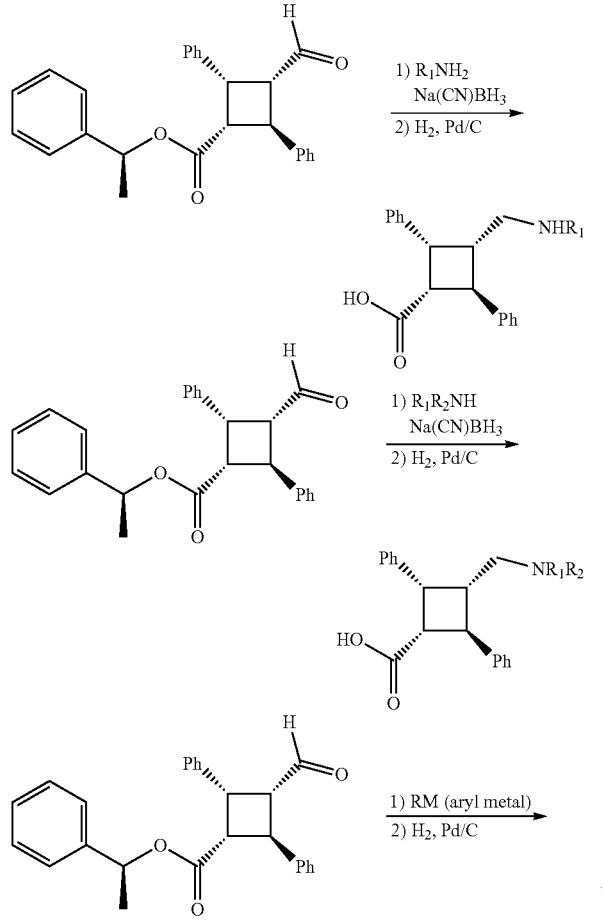

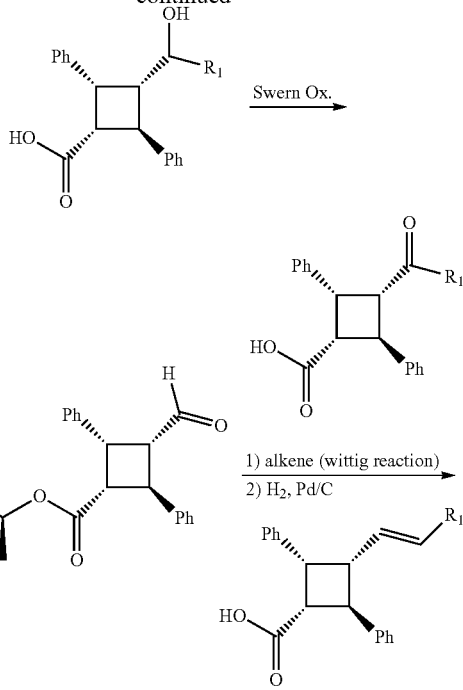

Example 11. Additional Route to Enantiopure Analogs

One way of resolving enantiomers is to convert them into their corresponding diastereomers and separate them by known purification techniques (as shown in Schemes 5 and 6). An additional method is to convert the two enantiomers of, for example, Compound 26 into the corresponding glucamine salts (Scheme 12), which are separable based on their difference solubility. Crystallization and neutralization allows for the isolated of either pure enantiomer (Harrington, P. J. et al 1997).

Scheme 12.

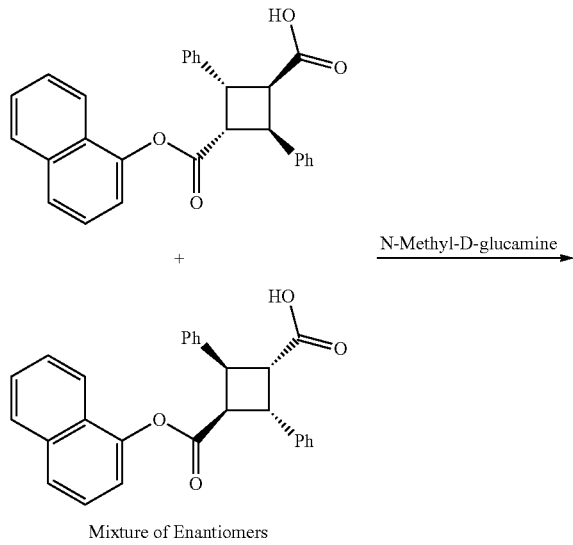

Mixture of Enantiomers

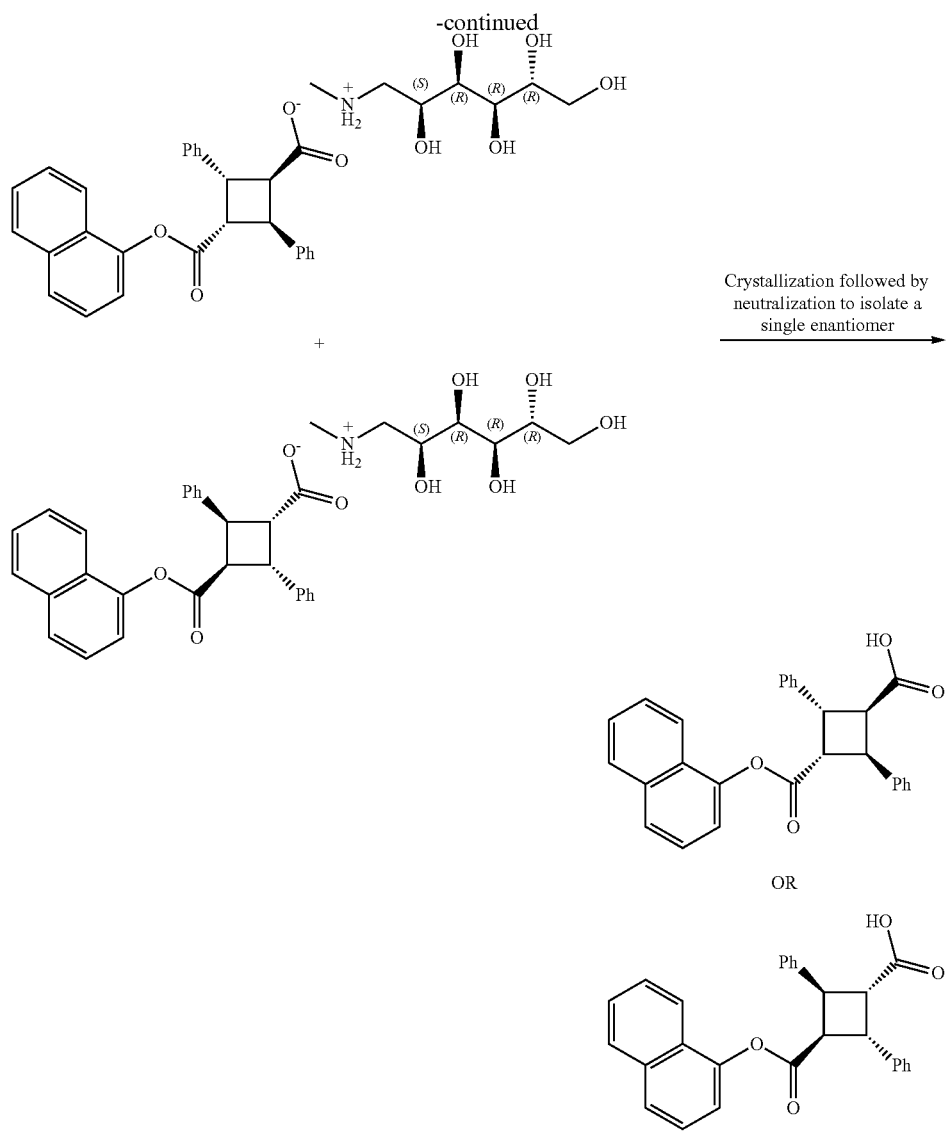
Example 12. Compounds 53 and 54
Compounds 53 and 54 were synthesized according to the synthetic methods described hereinabove and have analogous FABP inhibition activity to Compound 26.
3-(naphthalen-1-ylcarbamoyl)-2,4-diphenylcyclobutanecarboxylic acid (Compound 53)
$^1$H NMR (300 MHz, DMSO-d$_6$) δ 12.12 (b, 1H), 9.87 (s, 1H), 7.83 (d, J=7.8 Hz, 1H), 7.66 (d, J=8.1 Hz, 1H), 7.53 (d, J=7.2 Hz, 2H), 7.27-7.47 (m, 12H), 7.08 (d, J=7.2 Hz, 1H), 4.64 (dd, J=2.7 Hz, J=7.5, 1H), 4.32 (dd, J=3.0 Hz J=7.5 Hz, 1H), 3.59, (t, J=6.3, 1H), 1.74 (m, 1H).
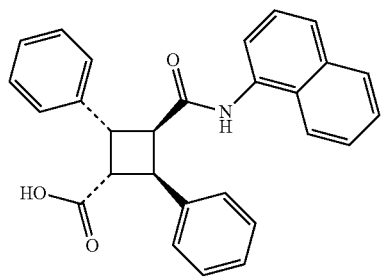 [SMILES: O=C(O)[C@H]1[C@H](c2ccccc2)[C@H](C(=O)Nc2cccc3ccccc23)[C@H]1c1ccccc1]
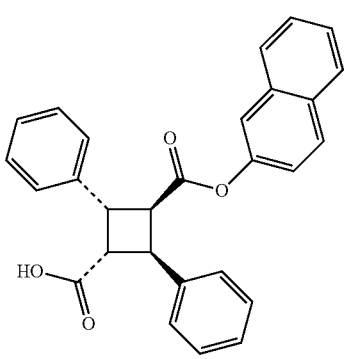 [SMILES: O=C(O)[C@H]1[C@H](c2ccccc2)[C@H](C(=O)Oc2ccc3ccccc3c2)[C@H]1c1ccccc1]

3-((naphthalen-2-yloxy) carbonyl)-2,4-diphenylcyclobutanecarboxylic Acid (Compound 54)

$^1$H NMR (300 MHz, DMSO-d$_6$) δ 12.14 (b, 1H), 7.86 (d, J=8.1 Hz, 1H), 7.77 (d, J=8.7 Hz, 1H), 7.67 (d, J=7.2 Hz, 1H), 7.27-7.54 (m, 10H), 7.23 (d, J=6.6 Hz, 2H), 6.77 (s, 1H), 6.48 (d, J=9.0 Hz, 1H), 4.56 (t, J=10.5 Hz, 1H), 4.47 (t, J=10.8 Hz, 1H), 4.28 (t, J=10.2 Hz, 1H), 3.98 (t, J=10.2 Hz, 1H); MS/MS (ESI-negative mode) m/e calculated for $C_{28}H_{23}O_4$—H: 421.1439. Found: 421.1.

Example 13. Additional In Vivo Mouse Studies and Pharmacokinetic Data

Figures 16A, 16B:
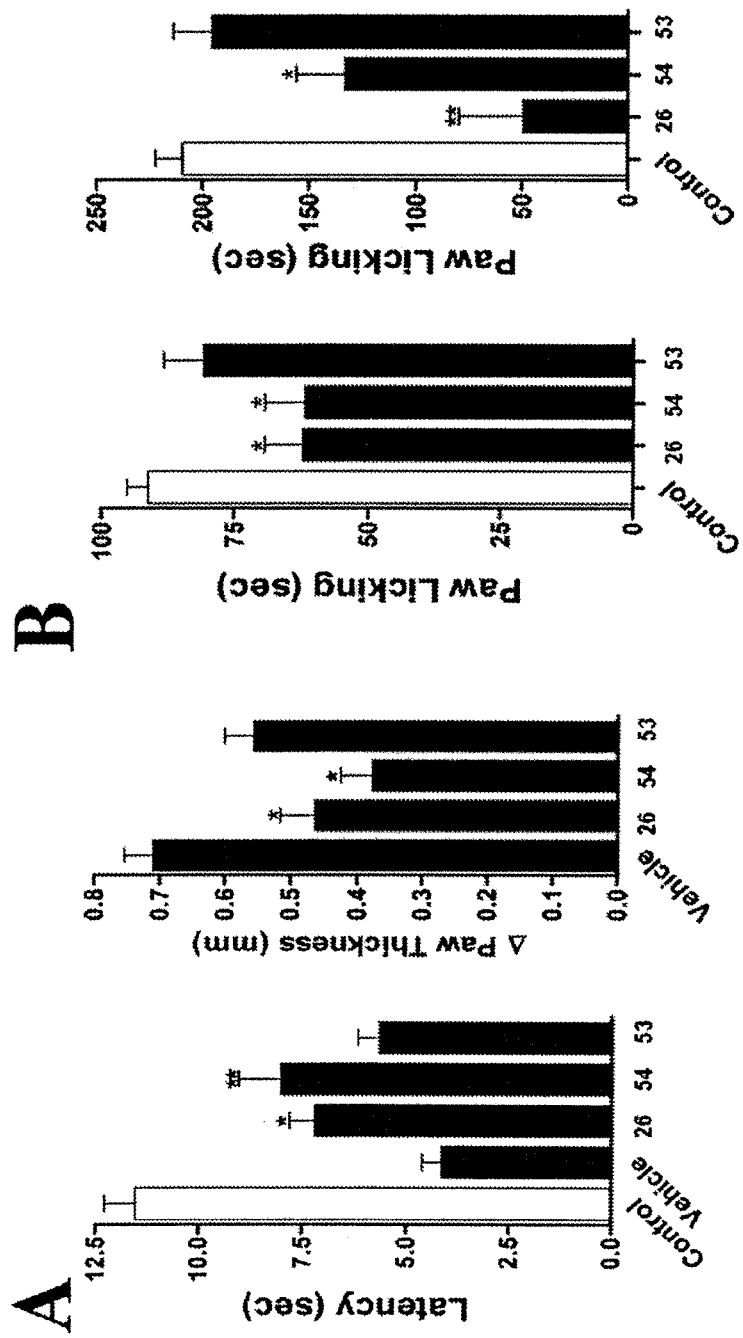
FIGS. 16A-16E. Effects of FABP inhibitors upon nociception in mice.
Figures 16C, 16D, 16E:
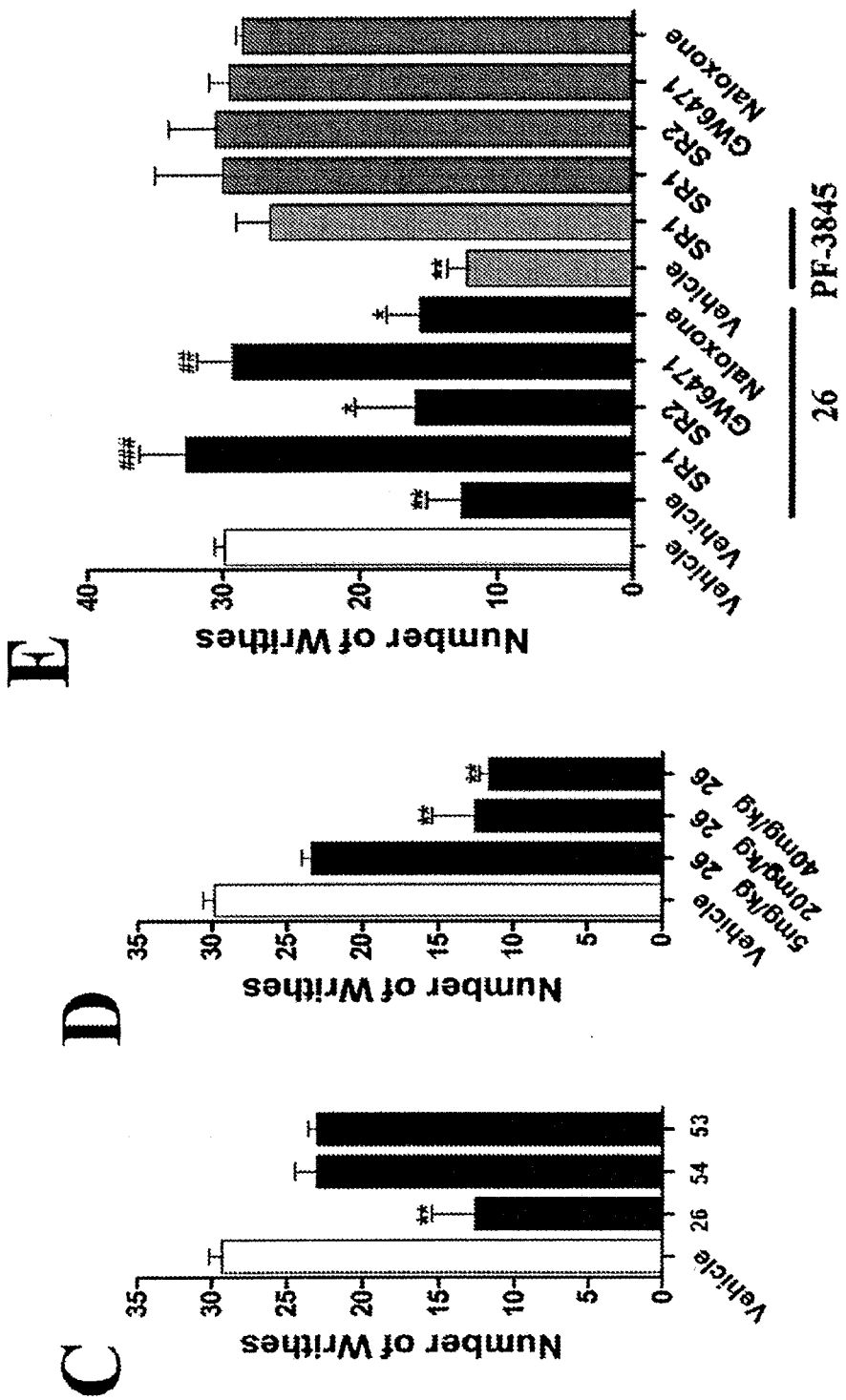
Figure 17:
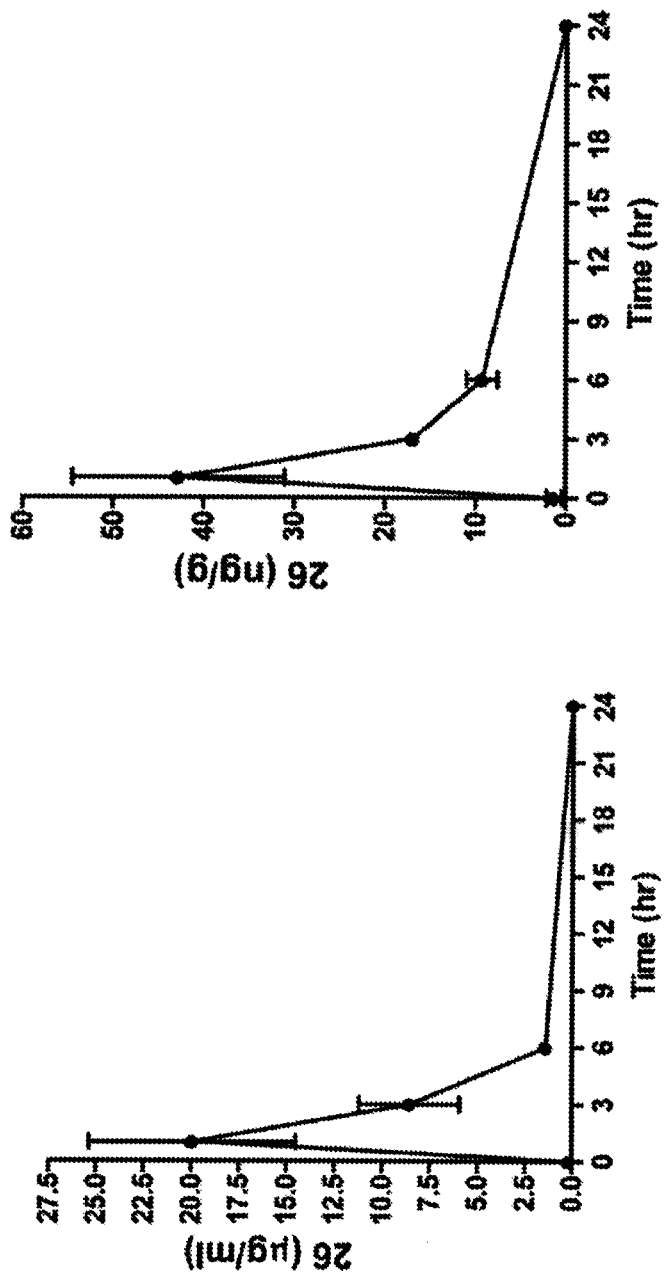
FIG. 17. Pharmacokinetic properties. Compound 26 elevates brain levels of the endocannabinoid anandamide (AEA). *, $p<0.05$.
Figure 18:
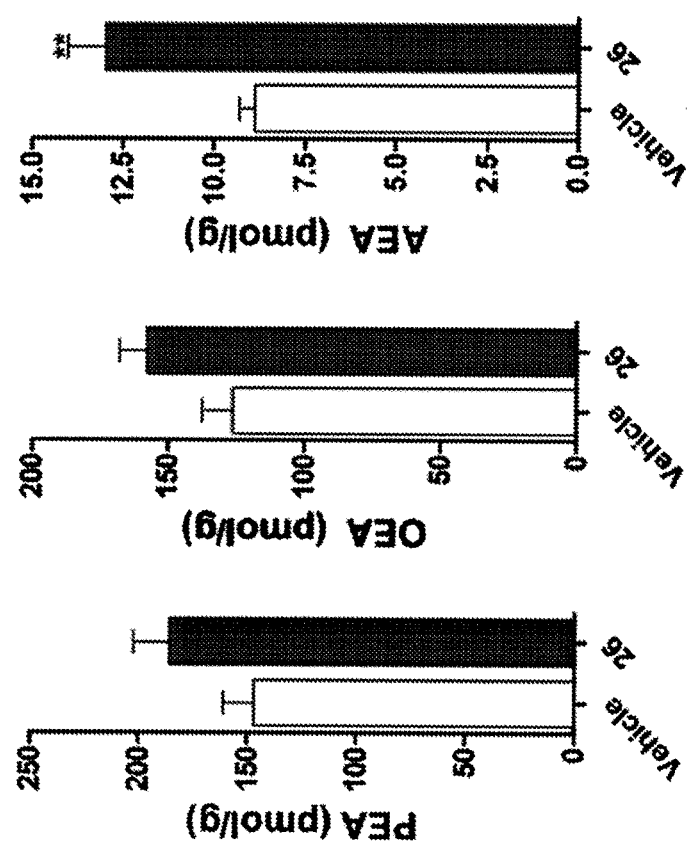
FIG. 18. Pharmacokinetic properties. Time course of Compound 26 in plasma (left panel) and brain (right panel) following a single injection (20 mg/kg, i.p.).

Compounds 26 and 54 (20 mg/kg, i.p.) reduced carrageenan-induced thermal hyperalgesia and paw edema in mice (FIG. 16A). Compounds 26 and 54 also reduced the first and second phases of formalin-induced nociception in mice (FIG. 16B). Compound 26 reduced acetic acid-induced writhing in mice (FIGS. 16C-D). Compound 26 also elevated brain levels of the endocannabinoid anandamide (AEA) (FIG. 17). Compound 26 was administered by a single injection and plasma and brain concentrations were analyzed over 24 hours.

Discussion

Virtual Screening and Initial Testing

High-throughput virtual screening in drug discovery has increasingly become a powerful and practical approach for pre-screening ligand libraries for biologically relevant molecules. Traditionally, docking programs attempt to approximate the intermolecular binding energy between a ligand and a receptor. To save computational time, often grid-based approaches provide the best compromise between accuracy and sampling time. Despite having moderate success rates, traditional docking typically favors larger molecules due to direct correlation between increasing van deer Walls energy and the number of atoms in a molecule. Often, only a small consideration of specific binding orientation is accounted for, mostly translated through favorable electrostatic interactions. A method of rescoring compounds based on their molecular footprints has been implemented into the program DOCK 6.5. Molecular footprints are two-dimensional representation of the ligand-receptor as a per-residue decomposition of the standard DOCK energy score. Thus, a virtual screening was carried out based on the hypothesis that molecular footprint matching between a docked library and a reference molecule would translate into a greater DOCK success rate based on the unique ability to enrich for true positives.

Before starting the virtual screening process, consideration was taken to select the most relevant biological target. The CB-1 receptor is predominately expressed in the brain and thus both FABP5 and FABP7 were considered relevant targets. FABP5 or epidermal fatty acid binding protein (E-FABP) is typical dispersed throughout the body (tongue, adipose tissue, dendritic cell, mammary gland, brain neurons, kidney, liver, lung and testis) and found abundantly in the epidermal cells of the skin. FABP7 or brain fatty acid binding protein (B-FABP) is typically expressed in high levels during mid-term embryonic development but not present in neurons. A structural comparison reveals that FABP7 (PDB: 1FE3, 2.8 Å) and FABP5 (PDB: 1B56, 2.05 Å) share 45% sequence identity and 63% similarity. Furthermore, both FABP7 and FABP5 bind fatty acid substrates with high affinity: although FABP7 typically shows higher binding affinity in-vitro. Interestingly, cross docking shows that DCE scores for FABP5 tend to be on average lower than those obtained for FABP7. Thus, FABP7 was selected as our target for virtual screening. High-throughput virtual screening utilizing the footprint rescoring method was conducted on FABP7 using oleic acid as the reference molecule. This entailed: 1) grid setup and docking, 2) minimization of each docked molecule and reference molecule on the receptor Cartesian coordinates, 3) calculating the molecular footprints of all docked molecules and reference, 4) calculation of a footprint similarity score (FPS) for each of the docked molecules versus the reference oleic acid, 5) MACCS fingerprint clustering, 6) rank-ordering based on each scoring criteria, 7) analysis and selection of compounds from each of the 250 cluster heads generated for each of the scoring criteria. As a result of the virtual screening, 48 compounds were selected by scoring criteria for in-vitro assay.

A sample footprint analysis of the reference compound oleic acid and a test compound called ZINC00695558 from the ChemDiv library. Footprint similarity scoring involved van der Waal, Coulombic, and hydrogen bonding forces. The methods employed for Footprint (FPS) scoring eliminated approximately 1,057,000 compounds with tile identification of 48 compounds selected for binding assay.

Figure 12:
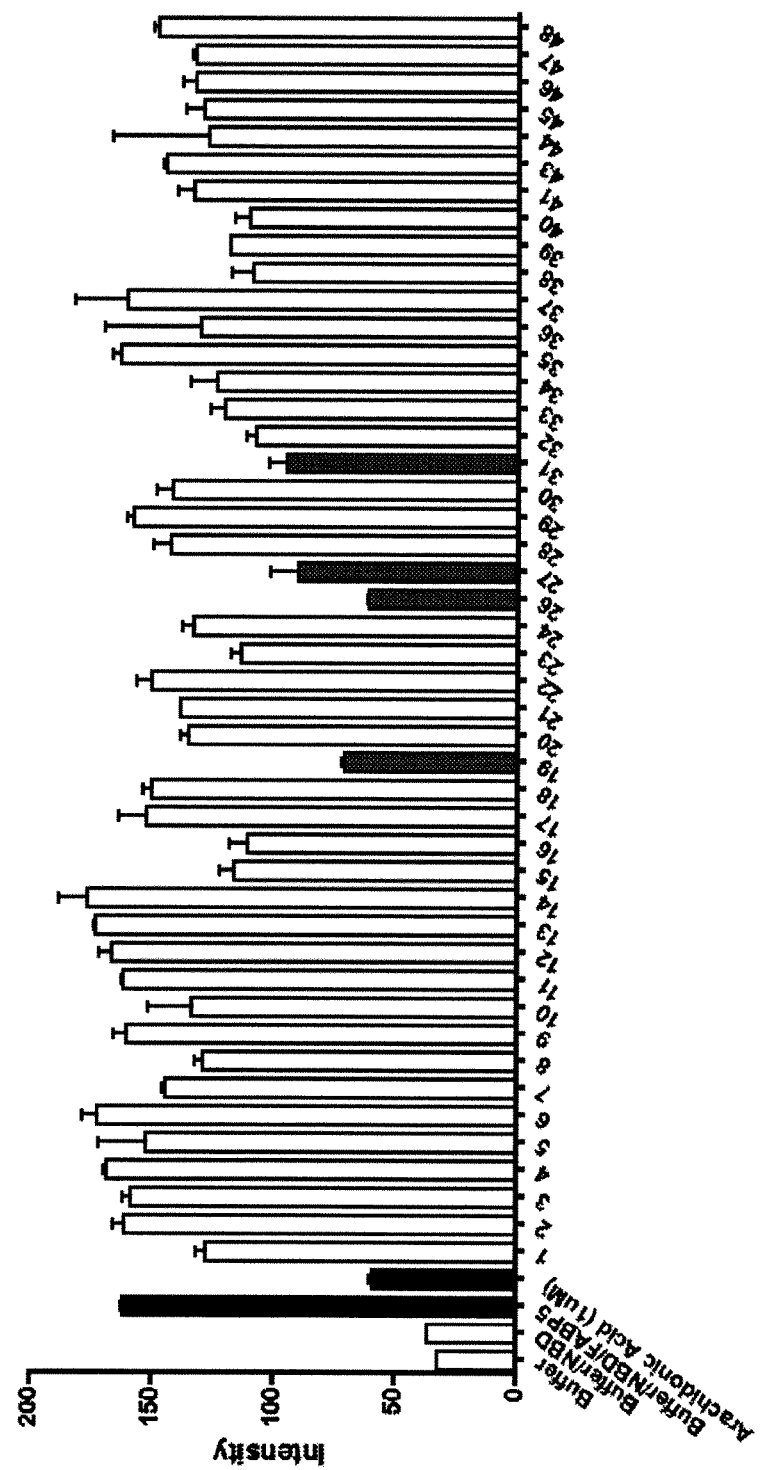
FIG. 12. High throughput fluorescence displacement assay with NBD-stearate. Shown in blue is the NBD-stearate FABP5 complex with no inhibitor, in black is arachidonic acid a potent inhibitor of FABP5, and in red are the four lead compounds.

The binding assay utilized an established fluorescence displacement assay. The degree to which the test compounds displaced NBD-stearate (1 µM) from FABPs is shown in FIG. 12. The first two samples, the buffer and NBD-stearate do not give appreciable fluorescence while the NBD-stearate plus purified FABP5 gives an appreciable fluorescence signal. The fourth sample is the positive control where arachidonic acid (1 µM), a fatty acid that binds strongly to FABP5 ($K_i$ 0.13 µM) decreases the signal. Each sample in this screen was measured in duplicate and approximately ⅓ of the test compounds appeared to cause displacement of NBD-stearate with a concomitant decrease in fluorescence. Four of the most potent (Compounds 19, 26, 27, and 31) were selected for further evaluation (FIGS. 16 and 17) and statistical analysis.

Figure 13A:
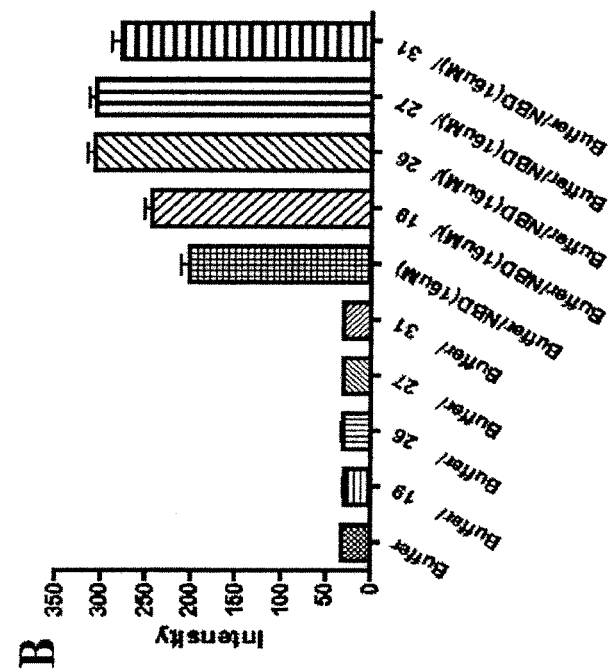
FIGS. 13A-13B. Verification of high throughput fluorescent displacement assay results.
Figure 13B:
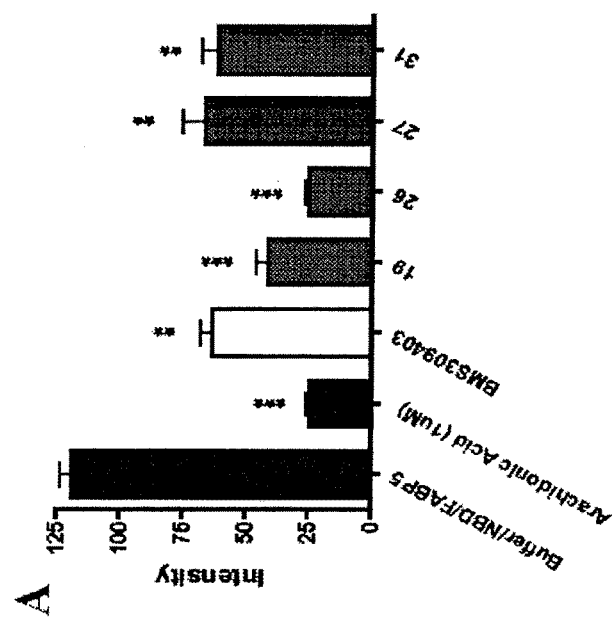

The best four FABP5 inhibitors discerned by the initial screen where then rerun in the NBD-fluorescent assay with replicate measurements at 10 µM. Inhibition of NBD-stearate binding to FABP5 by these compounds was highly significant with the naphthol truxillic derivative the most potent (Compound 26). In control experiments it was observed that the four test compounds (19, 26, 27, or 31) did not fluoresce under the assay conditions at 10 µM, nor did 10 µM concentrations of these compounds quench the fluorescence of 16 µM NBD-stearate, that is 16 times the concentration used in the routine assay (FIG. 13). The most potent inhibitor (compound 26) was synthesized to confirm the structure of the sample provided from ChemDiv. This α-naphthol truxillic acid derivative was tested over a wide concentration range and a $K_i$ of 0.93±0.08 µM (FIG. 8A) while γ-naphthol triuxillic derivative (Compound 49) was more potent with a $K_i$ of 0.75±0.07 µM (FIG. 8B), however Compound 49 was less soluble than Compound 26. The BMS compound had a $K_i$ of 0.75±0.164 µM (FIG. 8C).

The two most potent compounds, 26 and 49 (the α- and γ-truxillic acid 1-naphthyl esters), discerned from our in silico and biological screening, belong to a class of compounds that have been found to have anti-inflammatory and anti-nociceptive (Chi, Y. et al. 2005; Chi, Y. et al. 2006). Heretofore, the mechanism by which these effects were mediated was unknown. However, we can speculate that these compounds inhibit the transport of anandamide and other fatty acid ethanolamides, such as palmitoylethanolamide and oleoylethanolamide. These increased NAE levels would lead to greater signaling at the cannabinoid and potentiate NAE-mediated hypoalgesic and anti-inflammatory effects, indicating that modulation of NAE signaling may represent a therapeutic avenue for the treatment of pain.

Truxillic Acid Analogues

The design of truxillic acid based compounds targeting early stage (neurogenic pain response) and late stage (inflammatory pain response) has coincidently been studied recently based on the structure of the natural product (−)-incarvillateine. This natural product was first isolated from the plant species *Incarvillea sinensis*, which has been known in traditional Chinese medicine to treat rheumatism and pain. Interestingly, the isolated (−)-incarvillateine was found to possess antinociceptive properties on the same level as morphine.

Recently research (Chi, Y. et al. 2005) was carried out to identify potential leads for commercialization purposes focusing on di-esters and di-carboxylic acid derivatives. Despite the lack of target identification, α and β-truxillic acid di-ester and di-carboxylic acid derivatives were designed, synthesized and tested against early and late stage pain in formalin induced mouse models to study the effects of each analogue in-vivo. The results of the SAR study clearly showed that α-truxillic acid alone provided the best antinociceptive agent in both early and late stage pain. Although the para-hydroxyl functionalization on the phenyl rings slightly improved late stage pain relief it drastically reduced early stage pain relief.

As described herein, both α-2,4-diphenyl-cyclobutane-1, 3-dicarboxylic acid mono-esters and γ-2,4-diphenyl-cyclobutane-1,3-dicarboxylic acid mono-esters are reversible inhibitors of FABPs. These compounds bind to FABPs and block the shuttling of endocannabinoids within the cell and thereby increase the endogenous levels of the endocannabinoid anandamide by circumventing degradation by FAAH. Increased levels of anandamide result in the activation of the CB1 pathway leading to antinociceptive pain relief and reduction of inflammation which has been shown in a formalin induced mouse model (in-vivo results))

Figure 14:
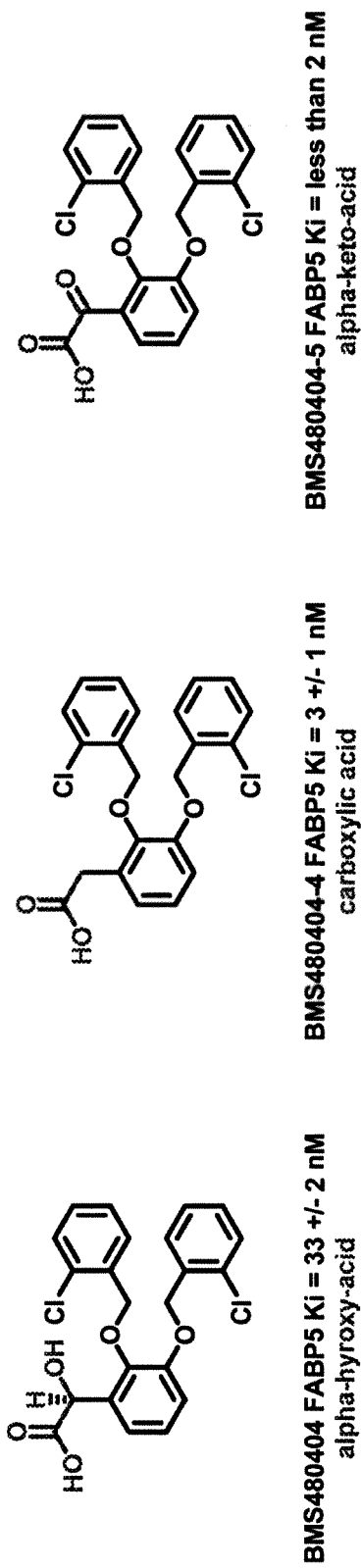
FIG. 14. Published in-vitro results of BMS480404. Highlighted in red is the essential functional group require for binding. The trend appears to be alpha keto acid>carboxylic acid>alpha hydroxy acid.
Figure 15:
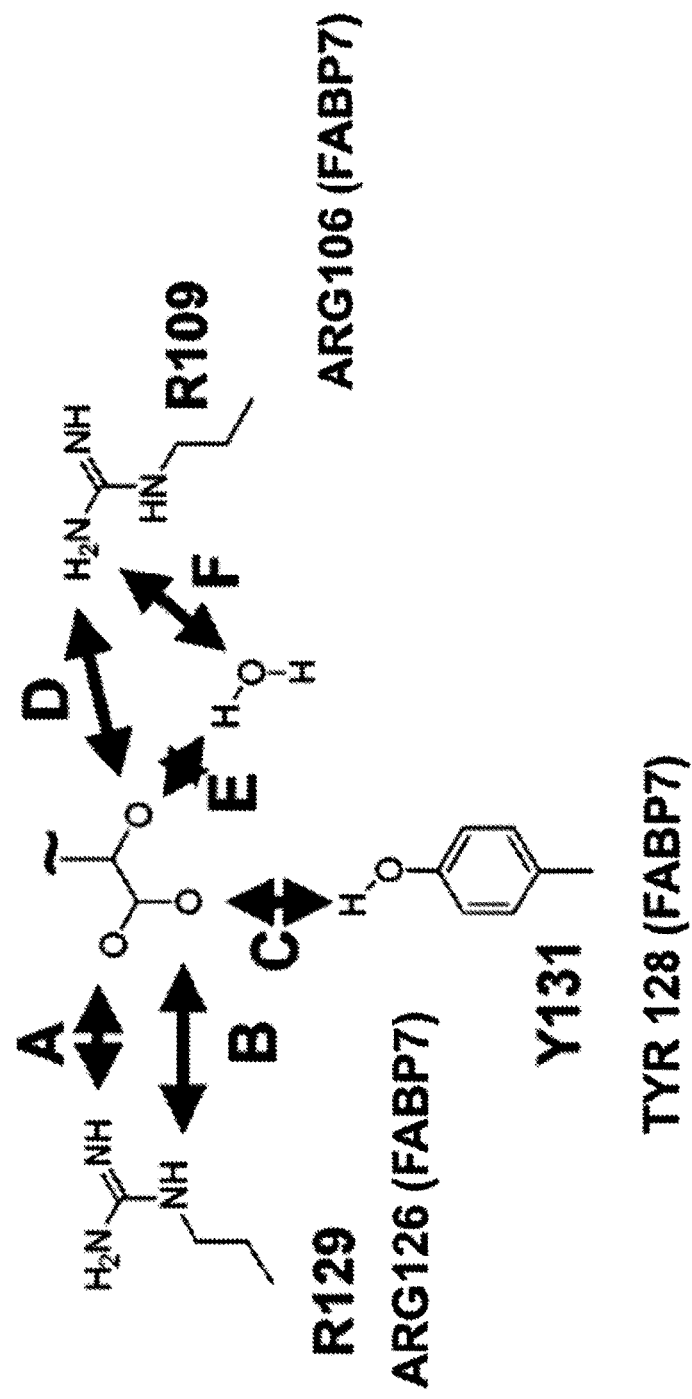
FIG. 15. Proposed binding of BMS480404-5 with water mediated hydrogen bonding between the alpha oxygen and ARG106 through water mediated hydrogen bonding.

To further our library of truxillic acid based FABP inhibitors, other known FABP5 inhibitors was studied. BMS480404 is reported to have a Ki of 33 nM±2 nM against FABP5 and a $K_i$ of 2.5 nM±0.1 nM against FABP4 determined by a 1-anilinonaphthalene-8-sulfonic acid (1,8-ANS) displacement assay (FIG. 14) (McDonnell, P. et al. 2006). Note that the assays are different and thus the $K_i$ determined may not be comparable to that obtained with the NBD-stearate assay. Interestingly, the carboxylic acid derivative of BMS480404 is shown to possess an improved Ki of 3 nM±1 nM and the alpha keto acid produced a $K_i$ of less than 2 nM. Thus incorporation of the alpha keto acid functionality, as in BMS480404-5, into the truxillic acid core may provide addition binding through water mediated hydrogen bonding to ARG 106 (FIG. 15). The interaction of the carboxylate of Compound 1 with ARG106 can be seen below with an electrostatic energy between −2 to −3 kcal/mol (FIG. 6). In addition, the compound BMS480404 contains two ethers and thus seemed a good alternative to the ester which could potentially be cleaved by esterases. Lastly, chirality may play an important role in binding and thus synthesis of enatiopure ligands may provide useful, as can already be seen by differences in $K_i$ for the α and γ 2,4-diphenyl-cyclobutane-1,3-dicarboxylic acid mono-esters, respectively.

As described herein, α-2,4-diphenyl-cyclobutane-1,3-dicarboxylic acid mono-(1-naphthol) ester (Compound 1) and γ-2,4-diphenyl-cyclobutane-1,3-dicarboxylic acid mono-(1-naphthol) ester (Compound 2) were selected based on a virtual screening. These leads provided excellent activity in-vitro against FABP5 with dose dependent Ki values of 0.93 μM±0.08 and 0.75 μM±0.07 respectively. In addition, α-2,4-diphenyl-cyclobutane-1,3-dicarboxylic acid mono-(1-naphthol) ester (Compound 2) provided excellent results in formalin induced mice models. Building upon these results, other α and γ truxillic acid based analogues targeting FABP's have analogous activity to Compound 2.

Summary

The current study identifies novel small molecule inhibitors of FABP5 and FABP7 by virtual screening employing DOCK and FPS. Despite having dissimilar distributions within the body, the structural similarity between FABP5 and FABP7 was shown to be as high as 66% with key binding residues fully conserved. We therefore choose to use FABP7 to identify potential lead compounds using DOCK and FPS, and performed similarity matching between the VDW and ES footprints of oleic acid our reference substrate, and over one million docked small molecules. Forty-eight molecules were identified in the virtual screen and subsequently assayed against FABP5 using a high-throughput fluorescent displacement assay. Overall, four compounds were identified as potential competitive inhibitors of FABP5. The most potent compound, Compound 26, was found to possess a diphenyl-cyclobutane core characteristic of the known natural product (−)-incarvillateine.

A novel α-truxillic acid 1-naphthyl mono-ester, Compound 26, was synthesized and the FABP5 NBD-stearate displacement assay of this compound showed a sub-micro molar Ki value. The resynthesized γ-form of truxillic acid 1-naphthyl mono-ester (Compound 49) also showed sub-micro molar efficacy against FABP5, which was considerably more potent than Compound 26, probably due to the difference in purity. Compound 26 (α-form) and Compound 49 (γ-form) were found to be as potent as BMS309403, a well known FABP inhibitor. Thus with both our virtual and biological screening, truxillic acid mono-esters were identified as a unique class of compounds that target FABPs.

Following biological screening and binding analyses of these inhibitors, we have shown that the novel FABP inhibitor Compound 26 produces antinociceptive and anti-inflammatory effects in mice. These findings are in agreement with a previous study demonstrating that some α-truxillic acid derivatives exhibited antinociceptive properties, although the mechanism of action was not identified (Chi, T. M. et a. 2006). It was subsequently reported that certain derivatives of α-truxillic acid activate PPARγ (Steri, R. et al. 2010). Although our work demonstrates that Compound 26 behaves as a weak agonist at PPARα and PPARγ, its antinociceptive effects were abolished by cannabinoid receptor antagonists. Therefore, the antinociceptive effects of Compound 26 likely resulted from potentiation of endocannabinoid signaling rather than activation of PPAR receptors. Taken together, our results establish FABPs as novel targets for antinociceptive drug development. In addition to the FABP transporters described here, heat shock protein 70, albumin, and a truncated fatty acid amide hydrolase protein have also been reported as intracellular shuttles for AEA (Fu, J. et al. 2011; Maccarrone, M. et al. 2010) and this area has been recently review (Fowler, C. J. 2012). These studies show the potential for the design of even more potent inhibitors that will be selective for individual FABPs.

REFERENCES

Arendaruk A P S A, Kharkevich D A (1967) Studies on Cyclobutanedicarboxylic Acids V. Sythesis of Bisquarternary Salts of Alkylamine Esters and Amides of the Stereoisomeric Truxillic Acids. Khimiko-Farmatsevticheskii Zhurnal: 18-21.

Ahn, K., Johnson, D. S., Mileni, M., Beidler, D., Long, J. Z., McKinney, M. K., Weerapana, E., Sadagopan, N., Liimatta, M., Smith, S. E., Lazerwith, S., Stiff, C., Kamtekar, S., Bhattacharya, K., Zhang, Y., Swaney, S., Van Beceiaere, K., Stevens, R. C., and Cravatt, B. F. (2009) Discovery and characterization of a highly selective FAAH inhibitor 1bat reduces inflammatory pain. Chem Biol 16, 411-420.

Balius T E, Mukherjee S, Rizzo R C (2011) Implementation and evaluation of a docking-rescoring method using molecular footprint comparisons. Journal of computational chemistry.

10. Holden P M, Kaur H, Gochin M, Rizzo R C (2012) Footprint-based identification of HIVgp41 inhibitors. Bioorg Med Chem Lett ss: 3011-3016.

Barf, T., Lehmann, F., Hammer, K., Haile, S., Axen, E., Medina, C., Uppenberg, J., Svensson, S., Rondahl, L., and Lundback, T. (2009) N-Benzyl-indolocarboxylic acids: Design and synthesis of potent and selective adipocyte fatty-acid binding protein (A-F ABP) inhibitors. Bioorg Med Chem Lett, 19, 1745-1748.

Chi, Y. M., Nakamura, M., Yoshizawa, T., Zhao, X. Y., Yan, W. M., Hashimoto, F., Kinjo, J., Nohara, T., and Sakurada, S. (2005) Anti-inflammatory activities of alpha-truxillic acid derivatives and their monomer components. Biol Pharm Bull 28, 1776-1778.

Chi, Y. M., Nakamura, M., Zhao, X. Y., Yoshizawa, T., Yan, W. M., Hashimoto, F., Kinjo, l, Nohara, T., and Sakurada, S. (2006) Antinociceptive activities of alpha-truxillic acid and beta-truxinic acid derivatives. Biol Pharm Bull 29, 580-584.

Chmurzynska, A. et al. (2006) Chmurzynska A (2006) The multigene family of fatty acid-binding proteins (FABPs): function, structure and polymorphism. J Appl Genet 47, 39-48.

Churi S B, Abdel-Aleem O S, Tumber K K, Scuderi-Porter H, Taylor B K (2008) Intrathecal rosiglitazone acts at peroxisome proliferator-activated receptor-gamma to rapidly inhibit neuropathic pain in rats. J Pain 9, 639-649.

Cravatt B F, Demarest K, Patricelli M P, Bracey M H, Giang D K, et al. (2001) Supersensitivity to anandamide and enhanced endogenous cannabinoid signaling in mice lacking fatty acid amide hydrolase. Proceedings of the National Academy of Sciences of the United States of America 98: 9371-9376.

Cravatt B F, Lichtman A H (2004) The endogenous cannabinoid system and its role in nociceptive behavior. Journal of neurobiology 61, 149-160.

Fowler C J (2012) Anandamide uptake explained? Trends Pharmacol Sci 33, 181-185.

Fu J, Bottegoni G, Sasso O, Bertorelli R, Rocchia W, et al. (2011) A catalytically silent FAAH-1 variant drives anandamide transport in neurons. Nature neuroscience 15: 64-69.

Furuhashi, M. and Hotamisligil, G. S. (2008) Fatty acid-binding proteins: role in metabolic diseases and potential as drug targets. Nat Rev Drug Discov 7, 489-503.

Haj-Dahmane S, Shen R Y (2009) Endocannabinoids suppress excitatory synaptic transmission to dorsal raphe serotonin neurons through the activation of presynaptic CB1 receptors. The Journal of pharmacology and experimental therapeutics 331: 186-196.

Haj-Dahmane S, Shen R Y (2005) The wake-promoting peptide orexin-B inhibits glutamatergic transmission to dorsal raphe nucleus serotonin neurons through retrograde endocannabinoid signaling. J Neurosci 25, 896-905.

Harringto, P. J.; Lodewijk, E. (1997) Twenty years of Naproxen Technology. Organic Process Research & Development, 1, 72-76.

Howlett, A. C., Reggio, P. H., Childers, S. R., Hampson, R. E., Ulloa, N. M., and Deutsch, D. G. (2011) Endocannabinoid tone versus constitutive activity of cannabinoid receptors. Br J Pharmacol 163, 1329-1343.

Irwin J J, Shoichet B K (2005) ZINC—A Free Database of Commercially Available Compounds for Virtual Screening. J Chem Inf Model 45: 177-182.

Jorgensen W L (2004) The many roles of computation in drug discovery. Science 303: 1813-1818.

Kaczocha, M., Glaser, S. T., and Deutsch, D. G. (2009) Identification of intracellular carriers for the endocannabinoid anandamide. Proc Natl Acad Sci USA 106, 6375-6380.

Kaczocha, M., Vivieca, S., Sun, J., Glaser, S. T., and Deutsch, D. G. (2012) Fatty Acid-binding Proteins Transport N-Acylethanolamines to Nuclear Receptors and Are Targets of Endocannabinoid Transport Inhibitors. J Biol Chem 287, 3415-3424.

Kuntz I D (1992) Structure-based strategies for drug design and discovery. Science 257: 1078-1082.

Lichtman A H, Martin B R (1990) Spinal action of cannabinoid-induced antinociception. NIDA Res Monogr 105: 422-424.

LoVerme J, Russo R, La Rana G, Fu J, Farthing J, et al. (2006) Rapid broad-spectrum analgesia through activation of peroxisome proliferator-activated receptor-alpha. J Pharmacol Exp Ther 319: 1051-1061.

Maccarrone M, Dainese E, Oddi S (2010) Intracellular trafficking of anandamide: new concepts for signaling. Trends in biochemical sciences 35: 601-608.

McDonnell, P. et al. (2006) NMR Structure of a Potent Small Molecule Inhibitor Bound to Human Keratinocyte Fatty Acid-Binding Protein. 49, 5013-5017.

Meng E C, Shoichet B K, Kuntz I D (1992) Automated docking with grid-based energy evaluation. J Comput Chem 13: 505-524.

Nakamura M, Chi Y M, Yan W M, Nakasugi Y, Yoshizawa T, et al. (1999) Strong Antinociceptive Effect of Incarvillateine, a Novel Monoterpene Alkaloid from *Incarvillea sinensis*. J Nat Prod 62: 1293-1294.

Shoichet B K (2004) Virtual screening of chemical libraries. Nature 432: 862-865.

Steri R, Rupp M, Proschak E, Schroeter T, Zettl H, et al. (2010) Truxillic acid derivatives act as peroxisome proliferator-activated receptor gamma activators. Bioorg Med Chem Lett 20: 2920-2923.

Sulsky, R. et al. (2007) Potent and selective biphenyl azole inhibitors of adipocyte fatty acid binding protein (aFABP). Bioorg Med Chem Lett 17, 3511-3515.

Yang H J L, Wang Z, Di-Cicco A, Levy D, et al. (2011) Novel Photolabile Diblock Copolymers Bearing Truxillic Acid Derivative Junctions. Macromolecules: 159-165.

What is claimed is:

1. A method of inhibiting the activity of a Fatty Acid Binding Protein (FABP) comprising contacting the FABP with a compound having the structure:

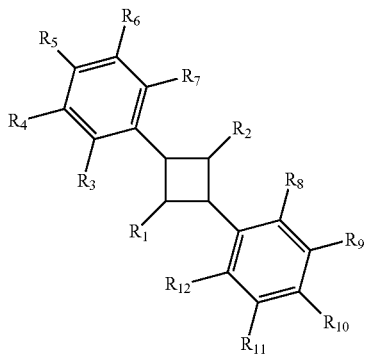

wherein
one of $R_1$ or $R_2$ is $-C(=O)R_{13}$, $-C(=O)OR_{13}$, $-C(=O)NR_{13}R_{14}$, -alkyl-OC(=O)OR$_{13}$, -alkyl-OC(=O)R$_{13}$, -alkyl-OR$_{13}$, -alkyl-NR$_{13}$R$_{14}$, -alkyl-NHC(=O)R$_{13}$, -alkyl-NHC(=O)OR$_{13}$, -alkyl-NHC(=O)NR$_{13}$R$_{14}$, -alkyl-NHC(=S)NR$_{13}$R$_{14}$, or -alkyl-NHC(=NR$_{13}$)NR$_{13}$R$_{14}$,
wherein $R_{13}$ and $R_{14}$ are each, independently, H, CF$_3$, C$_{1-10}$ alkyl, C$_{2-10}$ alkenyl, C$_{2-10}$ alkynyl, heteroalkyl, cycloalkyl, aryl, heteroaryl, heterocyclyl or combine to form a cycloalkyl or heterocyclyl; and
the other of $R_1$ or $R_2$ is $-C(=O)OR_{13}$, wherein $R_{13}$ is H; $R_3$, $R_4$, $R_5$, $R_6$, $R_7$, $R_8$, $R_9$, $R_{10}$, $R_{11}$ and $R_{12}$ are each independently, H, halogen, $-NO_2$, $-CN$, $-NHR_{15}$, $-NR_{15}R_{16}$, $-SR_{15}$, $-SO_2R_{15}$, $-OR_{15}$, $-CO_2R_{15}$, CF$_3$, -alkyl-NHR$_{15}$, -alkyl-NHR$_{15}$R$_{16}$, -alkyl-OR$_{15}$, C$_{1-10}$ alkyl, C$_{2-10}$ alkenyl, C$_{2-10}$ alkynyl, aryl, heteroaryl, or heterocyclyl,
wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl,
or a pharmaceutically acceptable salt thereof.

2. The method of claim 1, wherein the compound has the structure:

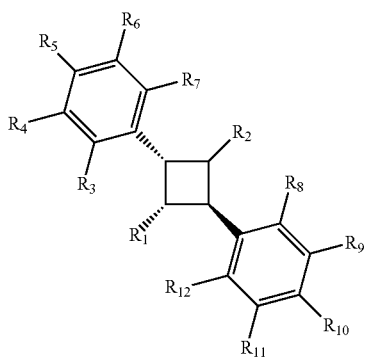

wherein
one of $R_1$ or $R_2$ is $-C(=O)R_{13}$, $-C(=O)OR_{13}$, $-C(=O)NR_{13}R_{14}$, -alkyl-OC(=O)OR$_{13}$, -alkyl-OC(=O)R$_{13}$, -alkyl-OR$_{13}$, -alkyl-NR$_{13}$R$_{14}$, -alkyl-NHC(=O)R$_{13}$, -alkyl-NHC(=O)OR$_{13}$, -alkyl-NHC(=O)NR$_{13}$R$_{14}$, -alkyl-NHC(=S)NR$_{13}$R$_{14}$, or -alkyl-NHC(=NR$_{13}$)NR$_{13}$R$_{14}$,
wherein $R_{13}$ and $R_{14}$ are each, independently, H, CF$_3$, C$_{1-10}$ alkyl, C$_{2-10}$ alkenyl, C$_{2-10}$ alkynyl, heteroalkyl, cycloalkyl, aryl, heteroaryl, heterocyclyl or combine to form a cycloalkyl or heterocyclyl; and
the other of $R_1$ or $R_2$ is $-C(=O)OR_{13}$, wherein $R_{13}$ is H; $R_3$, $R_4$, $R_5$, $R_6$, $R_7$, $R_8$, $R_9$, $R_{10}$, $R_{11}$ and $R_{12}$ are each independently, H, halogen, $-NO_2$, $-CN$, $-NHR_{15}$, $-NR_{15}R_{16}$, $-SR_{15}$, $-SO_2R_{15}$, $-OR_{15}$, $-CO_2R_{15}$, CF$_3$, -alkyl-NHR$_{15}$, -alkyl-NHR$_{15}$R$_{16}$, C$_{1-10}$ alkyl, C$_{2-10}$ alkenyl, C$_{2-10}$ alkynyl, aryl, heteroaryl, or heterocyclyl,
wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl,
wherein when one of $R_1$ or $R_2$ is $-C(=O)OH$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$, is other than $-C(=O)OR_{13}$ where $R_{13}$ is $-CH_3$, $-CH_2CH_3$, tolyl or propyl 1-bromo-1-methylpropanoyloxybutyl ester, or $-C(=O)NR_{13}R_{14}$ where one of $R_{13}$ or $R_{14}$ is phenyl and the other is $-H$, or both of $R_{13}$ and $R_{14}$ are $-H$, and
or an enantiomer or pharmaceutically acceptable salt thereof.

3. The method of claim 1, wherein the compound has the structure:

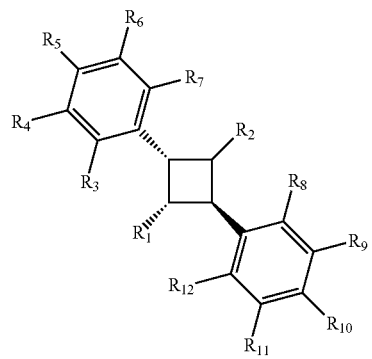

wherein
one of $R_1$ or $R_2$ is $-C(=O)R_{13}$, $-C(=O)OR_{13}$, $-C(=O)NR_{13}R_{14}$, -alkyl-OC(=O)OR$_{13}$, -alkyl-OC(=O)R$_{13}$, -alkyl-OR$_{13}$, -alkyl-NR$_{13}$R$_{14}$, -alkyl-NHC(=O)R$_{13}$, -alkyl-NHC(=O)OR$_{13}$, -alkyl-NHC(=O)NR$_{13}$R$_{14}$, -alkyl-NHC(=S)NR$_{13}$R$_{14}$, or -alkyl-NHC(=NR$_{13}$)NR$_{13}$R$_{14}$,
wherein $R_{13}$ and $R_{14}$ are each, independently, H, CF$_3$, C$_{1-10}$ alkyl, C$_{2-10}$ alkenyl, C$_{2-10}$ alkynyl, heteroalkyl, cycloalkyl, aryl, heteroaryl, heterocyclyl or combine to form a cycloalkyl or heterocyclyl; and
the other of $R_1$ or $R_2$ is $-C(=O)OR_{13}$, wherein $R_{13}$ is H; $R_3$, $R_4$, $R_5$, $R_6$, $R_7$, $R_8$, $R_9$, $R_{10}$, $R_{11}$ and $R_{12}$ are each independently, H, halogen, $-NO_2$, $-CN$, $-NHR_{15}$, $-NR_{15}R_{16}$, $-SR_{15}$, $-SO_2R_{15}$, $-OR_{15}$, $-CO_2R_{15}$, CF$_3$, -alkyl-NR$_{15}$R$_{16}$, C$_{1-10}$ alkyl, C$_{2-10}$ alkenyl, C$_{2-10}$ alkynyl, aryl, heteroaryl, or heterocyclyl,
wherein $R_{15}$ and $R_{16}$ are each, independently, H, CF$_3$, C$_{1-10}$ alkyl, C$_{2-10}$ alkenyl, C$_{2-10}$ alkynyl, heteroalkyl, cycloheteroalkyl, aryl, heteroaryl, or heterocyclyl,
wherein when one of $R_1$ or $R_2$ is $-C(=O)OH$ and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than $-C(=O)OR_{13}$ where $R_{13}$ is $-CH_3$, $-CH_2CH_3$, $-(CH_2)_4CH_3$, $-(CH_2)_7CH_3$, $-CH(CH_3)_2$, $-CH_2C(O)CH_3$, tolyl, 1-Naphthol or propyl 1-bromo-1-methylpropanoyloxybutyl ester, or $-C(=O)NR_{13}R_{14}$ where one of $R_{13}$ or $R_{14}$ is phenyl and the other is $-H$, or both of $R_{13}$ and $R_{14}$ are $-H$, and or an enantiomer or pharmaceutically acceptable salt thereof.

4. The method of claim 1, wherein the compound has the structure:

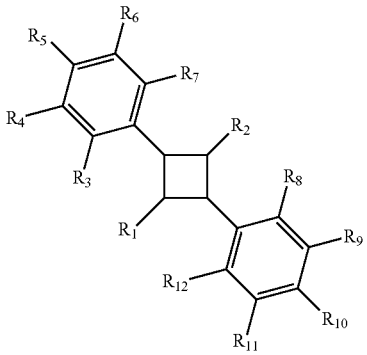

wherein
one of $R_1$ or $R_2$ is —C(=O)$R_{13}$, —C(=O)C$R_{13}$, —C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)Rn, -alkyl-NHC(=O)O$R_{13}$, -alkyl-NHC(=O)N$R_{13}R_{14}$, -alkyl-NHC(=S)N$R_{13}R_{14}$, or -alkyl-NHC(=N$R_{13}$)N$R_{13}R_{14}$, wherein $R_{13}$ and $R_{14}$ are each, independently, H, CF$_3$, $C_{1-10}$ alkyl, $C_{2-10}$ alkenyl, $C_{2-10}$ alkynyl, heteroalkyl, cycloalkyl, aryl, heteroaryl, heterocyclyl or combine to form a cycloalkyl or heterocyclyl; and the other of $R_1$ or $R_2$ is —C(=O)O$R_{13}$, wherein $R_{13}$ is H; $R_3$, $R_4$, $R_5$, $R_6$, $R_7$, $R_8$, $R_9$, $R_{10}$, $R_{11}$ and $R_{12}$ are each independently, H, halogen, —NO$_2$, —CN, —NH$R_{15}$, —N$R_{15}R_{16}$, —S$R_{15}$, —SO$_2R_{15}$, —O$R_{15}$, —CO$_2R_{15}$, CF$_3$, -alkyl-NH$R_{15}$, -alkyl-N$R_{15}R_{16}$, -alkyl-O$R_{15}$, $C_{1-10}$ alkyl, $C_{2-10}$ alkenyl, $C_{2-10}$ alkynyl, aryl, heteroaryl, or heterocyclyl, wherein $R_{15}$ and $R_{16}$ are each, independently, H, CF$_3$, $C_{1-10}$ alkyl, $C_{2-10}$ alkenyl, $C_{2-10}$ alkynyl, heteroalkyl, cycloheteroalkyl, aryl, heteroaryl, or heterocyclyl, wherein when one of $R_1$ or $R_2$ is —C(αO)OH, then the other of $R_1$ or $R_2$ is other than —C(=O)O$R_{13}$ where $R_{13}$ is alkyl, heteroalkyl, substituted phenyl or benzyl, —C(=O)NH$R_{13}R_{14}$ where one of $R_{13}$ or $R_{14}$ is —H, phenyl or substituted phenyl and the other is —H, or —C(=O)N$R_{13}R_{14}$ where $R_{13}$ and $R_{14}$ combine to form a piperidine or morpholine, or a pharmaceutically acceptable salt thereof.

5. The method of claim 4,
wherein
when one of $R_1$ or $R_2$ is —C(=O)OH and $R_3$, $R_4$, $R_5$, $R_6$, $R_7$, $R_8$, $R_9$, $R_{10}$, $R_{11}$ and $R_{12}$ are each H, then the other of $R_1$ or $R_2$ is other than —C(=O)O$R_{13}$ where $R_{13}$ is alkyl, heteroalkyl, substituted phenyl or benzyl, —C(=O)NH$R_{13}R_{14}$ where one of $R_{13}$ or $R_{14}$ is —H, phenyl or substituted phenyl and the other is —H, or —C(=O)N$R_{13}R_{14}$ where $R_{13}$ and $R_{14}$ combine to form a piperidine or morpholine.

6. The method of claim 1, wherein the compound has the structure:

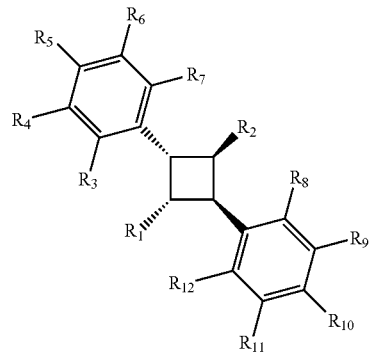

wherein
one of $R_1$ or $R_2$ is —C(=O)$R_{13}$, —C(=O)O$R_{13}$, —C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)N$R_{13}R_{14}$, -alkyl-NHC(=S)N$R_{13}R_{14}$, or -alkyl-NHC(=N$R_{13}$)N$R_{13}R_{14}$, wherein $R_{13}$ and $R_{14}$ are each, independently, H, CF$_3$, $C_{1-10}$ alkyl, $C_{2-10}$ alkenyl, $C_{2-10}$ alkynyl, heteroalkyl, cycloalkyl, aryl, heteroaryl, heterocyclyl or combine to form a cycloalkyl or heterocyclyl; and the other of $R_1$ or $R_2$ is —C(=O)O$R_{13}$, wherein $R_{13}$ is H; $R_3$, $R_4$, $R_5$, $R_6$, $R_7$, $R_8$, $R_9$, $R_{10}$, $R_{11}$ and $R_{12}$ are each independently, H, halogen, —NO$_2$, —CN, —NH$R_{15}$, —N$R_{15}R_{16}$, —S$R_{15}$, —SO$_2R_{15}$, —O$R_{15}$, —CO$_2R_{15}$, CF$_3$, -alkyl-NH$R_{15}$, -alkyl-N$R_{15}R_{16}$, -alkyl-O$R_{15}$, $C_{1-10}$ alkyl, $C_{2-10}$ alkenyl, $C_{2-10}$ alkynyl, aryl, heteroaryl, or heterocyclyl, wherein $R_{15}$ and $R_{16}$ are each, independently, H, CF$_3$, $C_{1-10}$ alkyl, $C_{2-10}$ alkenyl, $C_{2-10}$ alkynyl, heteroalkyl, cycloheteroalkyl, aryl, heteroaryl, or heterocyclyl, or a pharmaceutically acceptable salt thereof.

7. The method of claim 1, wherein the compound has the structure:

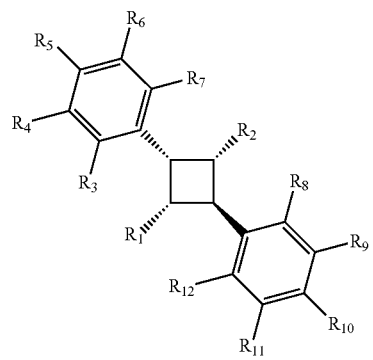

wherein
one of $R_1$ or $R_2$ is —C(=O)$R_{13}$, —C(=O)O$R_{13}$, —C(=O)N$R_{13}R_{14}$, -alkyl-OC(=O)O$R_{13}$, -alkyl-OC(=O)$R_{13}$, -alkyl-O$R_{13}$, -alkyl-N$R_{13}R_{14}$, -alkyl-NHC(=O)$R_{13}$, -alkyl-NHC(=O)O$R_{13}$, -alkyl-NHC(=O)N$R_{13}R_{14}$, -alkyl-NHC(=S)N$R_{13}R_{14}$, or -alkyl-NHC(=N$R_{13}$)N$R_{13}R_{14}$, wherein $R_{13}$ and $R_{14}$ are each, independently, H, CF$_3$, $C_{1-10}$ alkyl, $C_{2-10}$ alkenyl, $C_{2-10}$ alkynyl, heteroalkyl, cycloalkyl, aryl, heteroaryl, heterocyclyl or combine to form a cycloalkyl or heterocyclyl; and the other of $R_1$ or $R_2$ is —C(=O)$OR_{13}$, wherein $R_{13}$ is H; $R_3$, $R_4$, $R_5$, $R_6$, $R_7$, $R_8$, $R_9$, $R_{10}$, $R_{11}$ and $R_{12}$ are each independently, H, halogen, —$NO_2$, —CN, —$NHR_{15}$, —$NR_{15}R_{16}$, —$SR_{15}$, —$SO_2R_{15}$, —$OR_{15}$, —$CO_2R_{15}$, $CF_3$, -alkyl-$NHR_{15}$, -alkyl-$NHR_{15}R_{16}$, -alkyl-$OR_{15}$, $C_{1-10}$ alkyl, $C_{2-10}$ alkenyl, $C_{2-10}$ alkynyl, aryl, heteroaryl, or heterocyclyl, wherein $R_{15}$ and $R_{16}$ are each, independently, H, $CF_3$, $C_{1-10}$ alkyl, $C_{2-10}$ alkenyl, $C_{2-10}$ alkynyl, heteroalkyl, cycloheteroalkyl, aryl, heteroaryl, or heterocyclyl, or a pharmaceutically acceptable salt thereof.

8. The method of claim 1, wherein the compound has the structure:

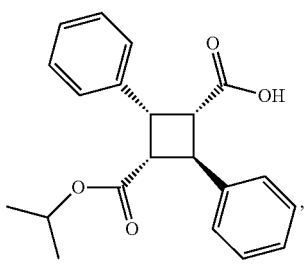 [SMILES: CC(C)OC(=O)[C@H]1[C@H](c2ccccc2)[C@@H](C(=O)O)[C@H]1c1ccccc1]

or a pharmaceutically acceptable salt thereof.

9. The method of claim 1, wherein the compound has the structure:

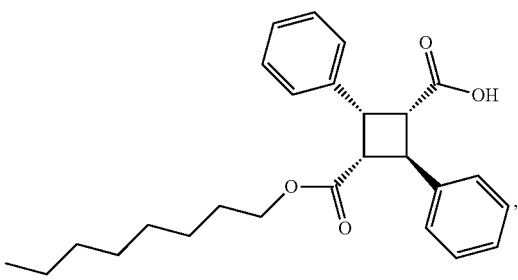 [SMILES: CCCCCCCCOC(=O)[C@H]1[C@H](c2ccccc2)[C@@H](C(=O)O)[C@H]1c1ccccc1]

or a pharmaceutically acceptable salt thereof.

10. The method of claim 1, wherein the compound has the structure:

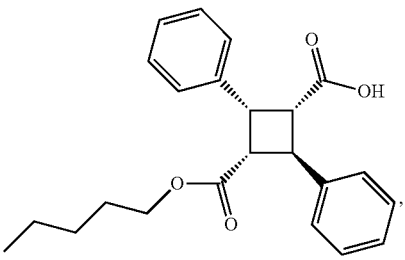 [SMILES: CCCCCOC(=O)[C@H]1[C@H](c2ccccc2)[C@@H](C(=O)O)[C@H]1c1ccccc1]

or a pharmaceutically acceptable salt thereof.

11. The method of claim 1, wherein the compound has the structure:

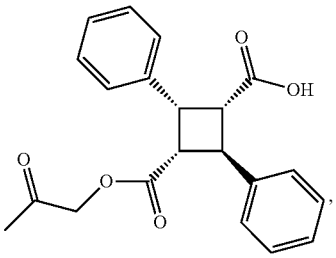 [SMILES: CC(=O)COC(=O)[C@H]1[C@H](c2ccccc2)[C@@H](C(=O)O)[C@H]1c1ccccc1]

or a pharmaceutically acceptable salt thereof.

12. The method of claim 1, wherein the compound inhibits binding of an FABP ligand to the FABP.

13. The method of claim 1, wherein the FABP ligand is an endocannabinoid ligand.

14. The method of claim 1, wherein the FABP ligand is anandamide (AEA) or 2-arachidonoylglycerol (2-AG).

* * * * *